(12) United States Patent
Bourke et al.

(10) Patent No.: US 8,354,408 B2
(45) Date of Patent: Jan. 15, 2013

(54) N-CONTAINING HETEROCYCLIC COMPOUNDS

(75) Inventors: David Gerard Bourke, Melbourne (AU); Christopher John Burns, Melbourne (AU); Anthony Nicholas Cuzzupe, Melbourne (AU); John Thomas Feutrill, Melbourne (AU); Marcel Robert Kling, Melbourne (AU); Tracy Leah Nero, Melbourne (AU)

(73) Assignee: YM Biosciences Australia Pty Ltd, Melbourne (AU)

( * ) Notice: Subject to any disclaimer, the term of this patent is extended or adjusted under 35 U.S.C. 154(b) by 0 days.

(21) Appl. No.: 12/739,704

(22) PCT Filed: Nov. 14, 2008

(86) PCT No.: PCT/AU2008/001699
§ 371 (c)(1),
(2), (4) Date: Nov. 30, 2010

(87) PCT Pub. No.: WO2009/062258
PCT Pub. Date: May 22, 2009

(65) Prior Publication Data
US 2011/0092499 A1    Apr. 21, 2011

Related U.S. Application Data

(60) Provisional application No. 60/988,357, filed on Nov. 15, 2007.

(51) Int. Cl.
| | |
|---|---|
| A61K 31/52 | (2006.01) |
| A61K 31/519 | (2006.01) |
| A61P 31/18 | (2006.01) |
| C07D 473/30 | (2006.01) |
| C07D 487/04 | (2006.01) |

(52) U.S. Cl. ........ 514/247; 514/256; 514/438; 544/242; 544/244; 549/29; 549/59

(58) Field of Classification Search .................. 514/247, 514/256, 438; 544/242, 244; 549/29, 59
See application file for complete search history.

(56) References Cited

U.S. PATENT DOCUMENTS
7,648,986 B2 * 1/2010 Nagarathnam et al. .... 514/234.2

FOREIGN PATENT DOCUMENTS
| | | | |
|---|---|---|---|
| JP | 2004/307440 | * | 11/2004 |
| WO | WO 91/18887 | * | 12/1991 |
| WO | WO 00/15645 | * | 3/2000 |
| WO | WO 03/055890 | * | 7/2003 |
| WO | WO 03/059913 | * | 7/2003 |
| WO | WO-2008/011560 | | 1/2008 |

OTHER PUBLICATIONS

Ife, et al., J. Med. Chem., 1995, vol. 38(14), pp. 2763-2773.*
Patani, et al., J. Med. Chem., 1996, vol. 98(8), pp. 3147-3176.*
Ide, et al., J. Med. Chem., 1995, vol. 38(14), pp. 2763-2773.*
Filla et al., J. Med. Chem. (2003) 46:3060-3071.
Thompson et al., ASSAY and Drug Development Technologies (2008) 6:69-81.
International Search Report for PCT/AU2008/001699, mailed on Mar. 2, 2009, 2 pages.
International Preliminary Report on Patentability for PCT/AU2008/001699, issued on May 18, 2010, 9 pages.

* cited by examiner

Primary Examiner — Susannah Chung
(74) Attorney, Agent, or Firm — Morrison & Foerster LLP

(57) ABSTRACT

The present invention relates to N-containing heterocyclic compounds that are inhibitors of protein kinases including JAK kinases. In particular, the compounds are selective for JAK1, JAK2, JAK3 or TYK2 kinases and combinations thereof such as JAK1 and JAK2. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

11 Claims, No Drawings

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:

-continued

<223> OTHER INFORMATION: XHOI J1 primer

<400> SEQUENCE: 1
ccgctcgaga ctgaagtgga ccccacacat                                         30

<210> SEQ ID NO 2
<211> LENGTH: 30
<212> TYPE: DNA
<213> ORGANISM: Artificial Sequence
<220> FEATURE:
<223> OTHER INFORMATION: J1 KPNI primer

<400> SEQUENCE: 2
cggggtacct tattttaaaa gtgcttcaaa                                         30

<210> SEQ ID NO 3
<211> LENGTH: 31
<212> TYPE: DNA
<213> ORGANISM: Artificial Sequence
<220> FEATURE:
<223> OTHER INFORMATION: SALI jk2 primer

<400> SEQUENCE: 3
acgcgtcgac ggtgcctttg aagaccggga t                                       31

<210> SEQ ID NO 4
<211> LENGTH: 34
<212> TYPE: DNA
<213> ORGANISM: Artificial Sequence
<220> FEATURE:
<223> OTHER INFORMATION: jk2 NOTI primer

<400> SEQUENCE: 4
atagtttagc ggccgctcag aatgaaggtc attt                                    34

<210> SEQ ID NO 5
<211> LENGTH: 30
<212> TYPE: DNA
<213> ORGANISM: Artificial Sequence
<220> FEATURE:
<223> OTHER INFORMATION: XHOI J3 primer

<400> SEQUENCE: 5
ccgctcgagt atgcctgcca agaccccacg                                         30

<210> SEQ ID NO 6
<211> LENGTH: 30
<212> TYPE: DNA
<213> ORGANISM: Artificial Sequence
<220> FEATURE:
<223> OTHER INFORMATION: J3 KPNI primer

<400> SEQUENCE: 6
cggggtaccc tatgaaaagg acagggagtg                                         30

<210> SEQ ID NO 7
<211> LENGTH: 17
<212> TYPE: PRT
<213> ORGANISM: Artificial Sequence
<220> FEATURE:
<223> OTHER INFORMATION: synthetically constructed peptide substrate
<220> FEATURE:
<221> NAME/KEY: misc_feature
<222> LOCATION: 1
<223> OTHER INFORMATION: Xaa = biotinylated glutamic acid
<220> FEATURE:
<221> NAME/KEY: misc_feature
<222> LOCATION: 17

<223> OTHER INFORMATION: Xaa = amide modified phenylalanine

<400> SEQUENCE: 7

Xaa Gly Pro Trp Leu Glu Glu Glu Glu Ala Tyr Gly Trp Met Asp
 1               5                  10                  15

Xaa

<210> SEQ ID NO 8
<211> LENGTH: 17
<212> TYPE: PRT
<213> ORGANISM: Artificial Sequence
<220> FEATURE:
<223> OTHER INFORMATION: synthetically constructed peptide substrate
<220> FEATURE:
<221> NAME/KEY: misc_feature
<222> LOCATION: 1
<223> OTHER INFORMATION: Xaa = biotinylated glutamic acid

<400> SEQUENCE: 8

Xaa Gln Glu Asp Glu Pro Glu Gly Asp Tyr Phe Glu Trp Leu Glu Pro
 1               5                  10                  15

Glu

<210> SEQ ID NO 9
<211> LENGTH: 30
<212> TYPE: DNA
<213> ORGANISM: Artificial Sequence
<220> FEATURE:
<223> OTHER INFORMATION: 5TEL primer

<400> SEQUENCE: 9
ggaggatcct gatctctctc gctgtgagac                                    30

<210> SEQ ID NO 10
<211> LENGTH: 28
<212> TYPE: DNA
<213> ORGANISM: Artificial Sequence
<220> FEATURE:
<223> OTHER INFORMATION: 3TEL primer

<400> SEQUENCE: 10
aggcgtcgac ttcttcttca tggttctg                                      28

<210> SEQ ID NO 11
<211> LENGTH: 31
<212> TYPE: DNA
<213> ORGANISM: Artificial Sequence
<220> FEATURE:
<223> OTHER INFORMATION: JAK2F primer

<400> SEQUENCE: 11
acgcgtcgac ggtgcctttg aagaccggga t                                  31

<210> SEQ ID NO 12
<211> LENGTH: 34
<212> TYPE: DNA
<213> ORGANISM: Artificial Sequence
<220> FEATURE:
<223> OTHER INFORMATION: JAK2R primer

<400> SEQUENCE: 12
atagtttagc ggccgctcag aatgaaggtc attt                               34

<210> SEQ ID NO 13
<211> LENGTH: 35
<212> TYPE: DNA

```
<213> ORGANISM: Artificial Sequence
<220> FEATURE:
<223> OTHER INFORMATION: JAK3F primer

<400> SEQUENCE: 13
gaagtcgact atgcctgcca agacccacg atctt                        35
```

N-CONTAINING HETEROCYCLIC COMPOUNDS

CROSS-REFERENCE TO RELATED APPLICATIONS

This application is the national phase of PCT application PCT/AU2008/001699 having an international filing date of 14 Nov. 2008, which claims benefit of US provisional application No. 60/988,357 filed 15 Nov. 2007. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 415852003200Seqlist.txt | Oct. 11, 2010 | 3,172 bytes |

FIELD OF THE INVENTION

The present invention relates to N-containing heterocyclic compounds that are inhibitors of protein kinases including JAK kinases. In particular, the compounds are selective for JAK1, JAK2, JAK3 or TYK2 kinases and combinations thereof such as JAK1 and JAK2. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

BACKGROUND OF THE INVENTION

JAKs are kinases which phosphorylate a group of proteins called Signal Transduction and Activators of Transcription or STATs. When phosphorylated, STATs dimerize, translocate to the nucleus and activate expression of genes which lead to, amongst other things, cellular proliferation such as proliferation of endothelial cells and smooth muscle cells, and cause hypertrophy of cardiac myocytes.

A review of the JAK/STAT literature offers strong support to the hypothesis that this pathway is important for the recruitment and marshalling of the host immune response to environmental insults, such as viral and bacterial infection. Information accumulated from gene knock-out experiments have underlined the importance of members of the JAK family to the intracellular signalling triggered by a number of important immune regulatory cytokines. The therapeutic possibilities stemming from inhibition of the JAK/STAT pathway are thus in the sphere of immune modulation, and as such are likely to be promising drugs for the treatment of a range of pathologies in this area. In addition inhibitors of JAKs could be used for immunological and inflammatory diseases including organ transplants, asthma and chronic obstructive pulmonary disease (COPD) as well as autoimmune diseases such as systemic lupus erythematosus, mixed connective tissue disease, scleroderma, autoimmune vasculitides, multiple sclerosis, rheumatoid arthritis, Crohn's disease, Type I diabetes and autoimmune thyroid disorders.

The central role played by the JAK family of protein tyrosine kinases in the cytokine dependent regulation of both proliferation and end function of several important cell types indicates that agents capable of inhibiting the JAK kinases are useful in the prevention and chemotherapeutic treatment of disease states dependent on these enzymes. Potent and specific inhibitors of each of the currently known four JAK family members will provide a means of inhibiting the action of the cytokines that drive immunological and inflammatory diseases, such as those discussed above. Additionally, treatment of hyperproliferative disorders such as cancers including multiple myeloma; prostate, breast and lung cancer; gastric cancer; Hodgkin's Lymphoma; B-cell Chronic Lymphocytic Leukemia; metastatic melanoma; glioma; and hepatoma, by JAK inhibitors is indicated. Additionally the use of JAK kinase inhibitors for the treatment of viral diseases and metabolic diseases is indicated.

Potent inhibitors of JAK2, in addition to the above, will also be useful in vascular disease such as hypertension, hypertrophy, cardiac ischemia, heart failure (including systolic heart failure and diastolic heart failure), migraine and related cerebrovascular disorders, stroke, Raynaud's phenomenon, POEMS syndrome, Prinzmetal's angina, vasculitides, such as Takayasu's arteritis and Wegener's granulomatosis, peripheral arterial disease, heart disease and pulmonary arterial hypertension. JAK2 inhibitors will also be useful in myeloproliferatve disorders (MPDs) such as polycythemia vera (PV).

Potent and specific inhibitors of both JAK1 and JAK2 will be useful in the treatment of cancers including multiple myeloma; prostate, breast and lung cancer; Hodgkin's Lymphoma; B-cell Chronic Lymphocytic Leukemia; metastatic melanoma; multiple myeloma; gastric cancer; glioma; and hepatoma.

Potent and specific inhibitors of JAK3 will be useful as immunosuppressive agents for, amongst others, organ transplants, and immunological and inflammatory diseases such as asthma and chronic obstructive pulmonary disease as well as autoimmune diseases such as systemic lupus erythematosus, mixed connective tissue disease, scleroderma, autoimmune vasculitides, multiple sclerosis, rheumatoid arthritis, Crohn's disease, Type I diabetes and complications from diabetes, metabolic diseases, and other indications where immunosuppression may be desirable. Furthermore specific inhibitors of JAK3 may find application for therapeutic treatments for proliferative diseases such as leukaemia and lymphoma where JAK3 is hyperactivated.

Although the other members of the JAK family are expressed by essentially all tissues, JAK3 expression appears to be limited to hematopoetic cells. This is consistent with its essential role in signalling through the receptors for IL-2, IL4, IL-7, IL-9 and IL-15 by non-covalent association of JAK3 with the gamma chain common to these multichain receptors. Males with X-linked severe combined immunodeficiency (XSCID) have defects in the common cytokine receptor gamma chain (gamma c) gene that encodes a shared, essential component of the receptors of interleukin-2 (IL-2), IL-4, IL-7, IL-9, and IL-15. An XSCID syndrome in which patients with either mutated or severely reduced levels of JAK3 protein has been identified, suggesting that immunosuppression should result from blocking signalling through the JAK3 pathway. Gene Knock out studies in mice have suggested that JAK3 not only plays a critical role in B and T lymphocyte maturation, but that JAK3 is constitutively required to maintain T cell function. Taken together with the biochemical evidence for the involvement of JAK3 in signalling events downstream of the IL-2 and IL-4 receptor, these human and mouse mutation studies suggest that modulation of immune activity through the inhibition of JAK3 could prove useful in the treatment of T-cell and B-cell proliferative disorders such as transplant rejection and autoimmune diseases.

Prolonged immunomodulation through inhibition of JAK3 signalling should have great therapeutic potential for chronic diseases as long as JAK3 inhibition was achieved selectively and not accompanied by inhibition of other kinase-dependent signalling processes. In particular, the high degree of sequence identity held in common by members of the JAK family of kinases raises the possibility that a compound which inhibits JAK3 would also inhibit other members of the family with detrimental long term consequences. For example, prolonged inhibition of JAK2 is likely to lead to erythropenia and thrombocytopenia, since the receptors for both erythropoietin and thrombopoietin use only JAK2 for intracellular transmission of signals.

Compounds of the present invention may also be useful in targeting other kinases of therapeutic relevance, such as the Aurora kinases. The Aurora family of serine/threonine protein kinases are critical for the proper regulation of mitosis. Mammals express three Aurora kinase paralogs, and at least two Aurora kinases (Aurora A and B) are commonly overexpressed in human tumours including breast, lung, colon, ovarian, and pancreatic cancers. The Aurora A gene is amplified in many tumours, indicating that overexpression of Aurora A may confer a selective advantage for the growth of these tumours. Overexpression of Aurora B has also been reported to produce multi-nuclearity and induce aggressive metastasis, suggestion that the overexpression of Aurora kinase B has multiple functions in cancer development. Recent clinical experience and subsequent approvals of kinase inhibitors such as Imatinib, Gefitinib and Erlotinib illustrate that this class of enzymes will be useful for anticancer drug development. Aurora A itself has been identified as a particularly attractive drug target through observations that it can act as an oncogene and transform cells when ectopically expressed. VX-680, a potent inhibitor of Aurora A and B kinases, has been shown to suppress tumour growth in vivo. These findings highlight the desirability of identifying Aurora kinase inhibitors for use in cancer treatment.

Other kinases which may be useful therapeutic targets include CK2, TBK1, NEK9, LCK, ACK1, p38 kinase, FAK, CAK, CDK1, 2 and 4, GSK-3β, Abl, PDGF-R, PLK1, PLK2, PLK3, PYK2, c-Kit, NPM-ALK, Flt-3, c-Met, KDR, EGFR, TIE-2, VEGFR-1, VEGFR-3, c-SRC, LCK, HCK, LYN, FYN and YES.

Although the inhibition of various types of protein kinases, targeting a range of disease states, is clearly beneficial, it has been to date demonstrated that the identification of a compound which is selective for a protein kinase of interest, and has good "drug like" properties such as high oral bioavailability, is a challenging goal. In addition, it is well established that the predictability of inhibition, or selectivity, in the development of kinase inhibitors is quite low, regardless of the level sequence similarity between the enzymes being targeted.

The challenges in developing a therapeutically appropriate JAK1, JAK2, JAK3 or TYK2 inhibitors or combinations thereof, and aurora kinase inhibitors for use in treatment of kinase associated diseases such as immunological and inflammatory diseases including organ transplants; hyperproliferative diseases including cancer and myeloproliferative diseases; viral diseases; metabolic diseases; and vascular diseases, include designing a compound with appropriate specificity which also has good drug likeness properties.

There is therefore a continuing need to design and/or identify compounds which specifically inhibit the JAK and aurora family of kinases, and particularly compounds which may preferentially inhibit one or more of the JAK kinases relative to the other JAK kinases. There is a need for such compounds for the treatment of a range of disease states.

SUMMARY OF THE INVENTION

In a first aspect, there is provided a compound of formula I

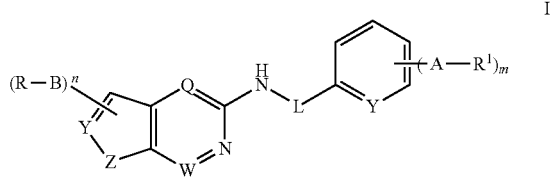

wherein
Q, W and Y are independently selected from N and $CR^2$;
Z is $NR^2$ or S;
L is absent, CO, $SO_2$ or substituted or unsubstituted $C_{1-6}$alkylene;
A and B are independently absent or substituted or unsubstituted $C_{1-6}$alkylene wherein one or more carbon atoms can be optionally replaced with O, CO, $NR^2$, $NR^2CO$, $CONR^2$, $NR^2SO_2$, $SO_2NR^2$, S and/or $S(O)_n$;
$R^1$ is independently selected from H, substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, OH, halogen, CN, $NO_2$, $NR^2R^3$, $SO_2R^3$, $SO_2NR^2R^3$, $CF_3$, $OCF_3$, $NR^2SO_2R^3$, $CO_2R^3$, $COSR^3$, $CSR^3$, $COR^3$, $NR^2$, $CSR^3$, $NR^2CSR^3$, $CONR^2R^3$, $NR^2COR^3$, $NR^2CONR^2R^3$, $SO_3R^3$, substituted or unsubstituted $C_{3-8}$cycloalkyl, substituted or unsubstituted aryl and substituted or unsubstituted heterocyclyl having up to 3 heteroatoms selected from N, O, S and $SO_2$;
R is selected from H, substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, OH, halogen, CN, $NO_2$, $CO_2R^3$, $CONR^2R^3$, $NR^2COR^3$, $SO_3R^3$, $C_{3-8}$cycloalkyl, aryl and heterocyclyl having up to 3 heteroatoms selected from N, O, S and $SO_2$, each of which may be substituted with up to 3 substituents independently selected from substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, OH, $OCF_3$, halogen, CN, $NO_2$, $NR^2R^3$, $SO_2R^3$, $SO_2NR^2R^3$, $NR^2SO_2R^3$, $CO_2R^3$, $COR^3$, $NR^2COR^3$, $R^2NHCO_2R^3$, $CONR^2R^3$, $NR^2CONR^2R^3$ and substituted or unsubstituted heterocyclyl having up to 3 heteroatoms selected from N, O, S and $SO_2$;
$R^2$ and $R^3$ are independently selected from H, substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, CN, substituted or unsubstituted $C_{3-8}$cycloalkyl, substituted or unsubstituted aryl and substituted or unsubstituted heterocyclyl having up to 3 heteroatoms selected from N, O, S and $SO_2$;
m is 1 to 3; and
n is 1 or 2;
salts, isomers and/or prodrugs thereof.

In a second aspect, there is provided a process for the preparation of the compound of formula I defined above which comprises the step of coupling a compound of formula II

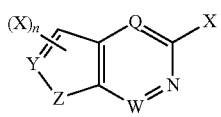

Formula II wherein,
Q, W, Y, Z and n are as defined in formula I above; and
X is a leaving group
with R as defined in formula I above and a compound of formula III

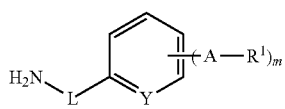

Formula III wherein L, A, Y, $R^1$ and m are as defined in formula I above.

The compounds of formula I are kinase inhibitors, preferably JAK inhibitors, more preferably JAK1, JAK2, JAK3 or TYK2 inhibitors. These compounds are useful in the treatment of a kinase associated disease, preferably a JAK kinase or aurora kinase associated disease such as immunological and inflammatory diseases; hyperproliferative diseases including myeloproliferative diseases; vascular diseases; viral diseases and metabolic diseases.

In a third aspect, there is provided a kinase inhibitor comprising the compound formula I defined above.

There is also provided use of the compound of formula I defined above as a kinase inhibitor.

There is further provided the compound of formula I defined above for use as a kinase inhibitor.

The compounds of formula I preferably act as selective JAK2 inhibitors, selective JAK3 inhibitors or selective JAK1 and JAK2 inhibitors.

The compound of formula I may also be administered in the form of a pharmaceutical composition together with a pharmaceutically acceptable carrier.

In a fourth aspect, there is provided a pharmaceutical composition comprising the compound of formula I defined above and a pharmaceutically acceptable carrier.

In one embodiment, the pharmaceutical composition also comprises one or more additional therapeutic agents.

The compound of formula I may be contained within or attached to an implant, such as a drug eluting stent. For example, when the compound is used for the treatment of pulmonary arterial hypertension (PAH), the compound may be contained within or attached to a pulmonary artery stent, which may act locally, or be released from the stent into the pulmonary circulation where the compound exerts its therapeutic activity in the pulmonary vasculature.

In a fifth aspect, there is provided an implant which comprises the compound of formula I defined above.

In a sixth aspect, there is provided a method for the treatment of a kinase associated disease such as immunological and inflammatory diseases including organ transplants; hyperproliferative diseases including cancer and myeloproliferative diseases; viral diseases; metabolic diseases; and vascular diseases which comprises administering a therapeutically effective amount of the compound of formula I or a pharmaceutical composition defined above to a subject in need thereof.

There is also provided use of the compound of formula I or a pharmaceutical composition as defined above in the manufacture of a medicament for the treatment of a kinase associated disease such as immunological and inflammatory diseases including organ transplants; hyperproliferative diseases including cancer and myeloproliferative diseases; viral diseases; metabolic diseases; and vascular diseases.

There is further provided use of the compound of formula I or a pharmaceutical composition as defined above in the treatment of a kinase associated disease such as immunological and inflammatory diseases including organ transplants; hyperproliferative diseases including cancer and myeloproliferative diseases; viral diseases; metabolic diseases; and vascular diseases.

There is still further provided the compound of formula I or a pharmaceutical composition defined above for use in the treatment of a kinase associated disease such as immunological and inflammatory diseases including organ transplants; hyperproliferative diseases including cancer and myeloproliferative diseases; viral diseases; metabolic diseases; and vascular diseases.

In a seventh aspect, there is provided a method of inhibiting a kinase in a cell comprising contacting the cell with the compound of formula I defined above.

DETAILED DESCRIPTION

The present invention relates to compounds of formula I that inhibit kinases, in particular JAK kinases such as JAK1, JAK2, JAK3 or TYK2 kinases or aurora kinases and are useful in the treatment of kinase associated diseases such as immunological and inflammatory diseases including organ transplants; hyperproliferative diseases including cancer and myeloproliferative diseases; viral diseases; metabolic diseases; and vascular diseases.

The present invention further relates salts, isomers and/or prodrugs of a compound of formula I:

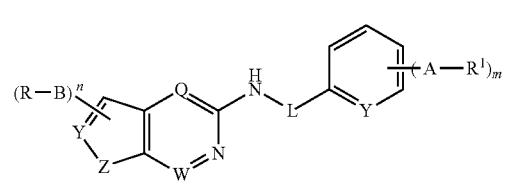

I wherein
Q, W and Y are independently selected from N and $CR^2$;
Z is $NR^2$ or S;
L is absent, CO, $SO_2$ or substituted or unsubstituted $C_{1-6}$alkylene;
A and B are independently absent or substituted or unsubstituted $C_{1-6}$alkylene wherein one or more carbon atoms can be optionally replaced with O, CO, $NR^2$, $NR^2CO$, CONR, $NR^2SO_2$, $SO_2NR^2$, S and/or $S(O)_n$;
$R^1$ is independently selected from H, substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, OH, halogen, CN, $NO_2$, $NR^2R^3$, $SO_2R^3$, $SO_2NR^2R^3$, $CF_3$, $OCF_3$, $NR^2SO_2R^3$, $CO_2R^3$, $COSR^3$, $CSR^3$, $COR^3$, $NR^2$, $CSR^3$, $NR^2CSR^3$, $CONR^2R^3$, NR²COR³, NR²CONR²R³, SO₃R³, substituted or unsubstituted $C_{3-8}$cycloalkyl, substituted or unsubstituted aryl and substituted or unsubstituted heterocyclyl having up to 3 heteroatoms selected from N, O, S and SO₂;

R is selected from H, substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, OH, halogen, CN, NO₂, CO₂R³, CONR²R³, NR²COR³, SO₃R³, $C_{3-8}$cycloalkyl, aryl and heterocyclyl having up to 3 heteroatoms selected from N, O, S and SO₂, each of which may be substituted with up to 3 substituents independently selected from substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, OH, OCF₃, halogen, CN, NO₂, NR²R³, SO₂R³, SO₂NR²R³, NR²SO₂R³, CO₂R³, COR³, NR²COR³, R²NHCO₂R³, CONR²R³, NR²CONR²R³ and substituted or unsubstituted heterocyclyl having up to 3 heteroatoms selected from N, O, S and SO₂;

R² and R³ are independently selected from H, substituted or unsubstituted $C_{1-6}$alkyl, substituted or unsubstituted $C_{2-6}$alkenyl, substituted or unsubstituted $C_{2-6}$alkynyl, substituted or unsubstituted $C_{1-6}$alkoxy, CN, substituted or unsubstituted $C_{3-8}$cycloalkyl, substituted or unsubstituted aryl and substituted or unsubstituted heterocyclyl having up to 3 heteroatoms selected from N, O, S and SO₂;

m is 1 to 3; and n is 1 or 2;

salts, isomers and/or prodrugs thereof.

In one embodiment, the compounds of formula I have the formula Ia

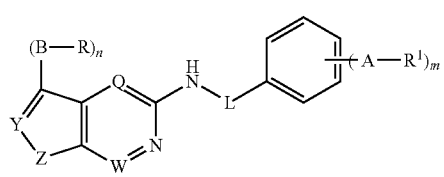

Ia wherein Q, W, Y, Z, L, A, B, R, R¹, m and n are as defined above.

In a preferred embodiment, the compounds of formula I and Ia have the formula Ib

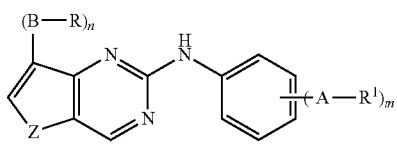

Ib wherein Z, A, B, R, R¹, m and n are as defined above.

A is preferably absent, substituted or unsubstituted $C_{1-6}$alkylene or substituted or unsubstituted divalent $C_{1-6}$alkoxy;

B is preferably absent or S;

R is preferably independently selected from H, halogen, CO₂R³, CONR²R³, $C_{3-8}$cycloalkyl, 5 or 6 membered aryl and 5 to 9 membered heterocyclyls having up to 3 heteroatoms selected from N, O, S and SO₂, each of which may be substituted with up to 3 substituents independently selected from substituted or unsubstituted $C_{1-6}$alkyl, substituted or unsubstituted 5 to 8 membered heterocyclyls having up to 3 heteroatoms selected from N, O, S and SO₂, R²OH, R²NHCO₂R³, OCF₃, substituted or unsubstituted $C_{1-6}$alkoxy, OH, NR²R³, SO₂NR²R³, NR²SO₂R³, NR²COR³, CONR²R³, NR²CoNR²R³, COR³, CO₂R³ and/or SO₂R³ wherein R² and R³ are as defined above.

A preferred substituted or unsubstituted 5 or 6 membered aryl for R is phenyl unsubstituted or substituted with at least one of NR²R³, NR²COR³, substituted or unsubstituted $C_{1-6}$alkoxy, substituted or unsubstituted 5 to 8 membered heterocyclyls having up to 3 heteroatoms selected from N, O, S and SO₂, SO₂NR²R³, NR²CONR²R³, NR²SO₂R³, R²OH, R²NHCO₂R³, OCF₃, CONR²R³ or substituted or unsubstituted $C_{1-6}$alkyl.

Preferred substituted or unsubstituted 5 to 9 membered heterocyclyls having up to 3 heteroatoms selected from N, O, S and SO₂ for R are saturated or unsaturated 5 to 9 membered heterocyclyls having 1 to 2 N atoms such as pyrazolyl, pyridinyl, 1,2,3,6-tetrahydro-pyridinyl and pyrimidinyl or saturated or unsaturated 5 to 9 membered heterocyclyls having 1 to 2 O atoms such as benzoxadiazolyl, each of which may be substituted with at least one of $C_{1-6}$alkoxy, CO₂R³ or NR²R³.

R¹ is preferably independently selected from H, halogen, substituted or unsubstituted $C_{1-6}$alkenyl, substituted or unsubstituted $C_{2-6}$alkyl, substituted or unsubstituted $C_{1-6}$alkoxy, OH, halogen, NO₂, NR²R³, NR²COR³, CO₂R³, SO₂R³, NR²SO₂ R³, substituted or unsubstituted $C_{3-8}$cycloalkyl, substituted or unsubstituted 5 or 6 membered aryl and substituted or unsubstituted 5 to 8 membered saturated or unsaturated heterocyclyl having up to 3 heteroatoms selected from N, O, S and SO₂.

Preferred substituted or unsubstituted 5 to 8 membered heterocyclyls having up to 3 heteroatoms selected from N, O, S and SO₂ for R¹ are 5 or 6 membered saturated or unsaturated heterocyclyls having up to 3 heteroatoms selected from N, O and S such as morpholino, thiomorpholino, thiomorpholino-1-oxide, thiomopholino-1,1-dioxide, NR²-piperazine, 4-hydroxy piperidine, 3-hydroxy pyrrolidine, 3-hydroxypyrrole, piperidine and pyrrolidine.

When the compounds of formulae I and Ia inhibit JAK3 kinases, one of A-R¹ and a substituent of R is preferably selected from groups that can react reversibly or irreversibly with a thiol moiety such as the thiol groups of the Cys963 residue of JAK3. Examples of such groups include Michael acceptors.

Michael acceptors are α,β-unsaturated carbonyl or thiocarbonyl compounds and selected examples are shown below.

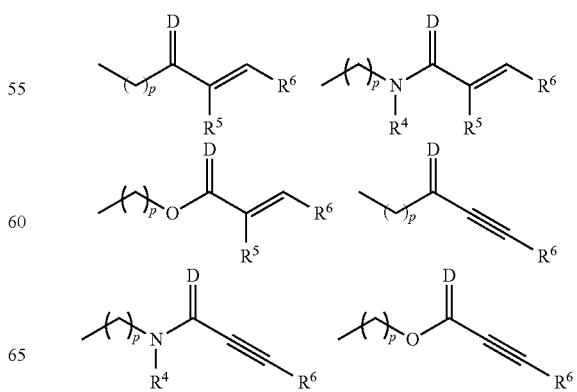

-continued

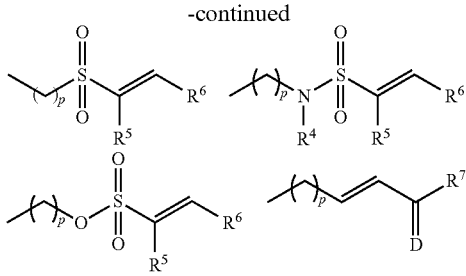

wherein

D is O or N;

R[4] is selected from H and substituted or unsubstituted C$_{1-4}$alkyl;

R[5] and R[6] are independently selected from H, substituted or unsubstituted C$_{1-4}$alkyl, C$_{1-4}$alkylNR[8]R[9], C$_{1-4}$alkylOR[8], substituted or unsubstituted aryl or may be joined to form a substituted or unsubstituted 5 to 8 membered ring optionally containing one or more heteroatoms selected from O, S, SO$_2$ and NR[4];

R[7] is selected from OH, OC$_{1-4}$alkyl, NR[8]R[9];

p is 0 to 4; and

R[8] and R[9] are independently selected from H, substituted or unsubstituted C$_{1-4}$alkyl or may be joined to form a substituted 3-8 membered ring optionally containing one or more heteroatoms selected from O, S, SO$_2$ and NR[4].

Other groups which can undergo reversible or irreversible reaction with thiol moieties include, ketones, aldehydes, α-acyloxy ketones, α-phenoxy ketones, halomethyl ketones, maleimides, nitriles, 1,2,4-thiadiazoles, 2-vinyl oxazoles. 2-alkynyl-oxazoles, keto-oxazoles, cyclic disulfides, epoxides and O-acyl hydroxamates.

Illustrative examples of compounds of the present invention are shown in the following table.

| No | Structure | Mol Weight | Formula | $^1$H NMR data | LC-MS |
|---|---|---|---|---|---|
| 1 | 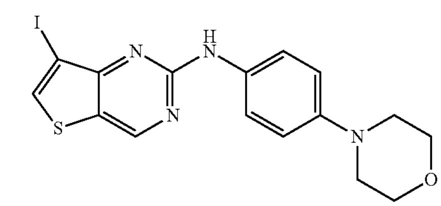 [SMILES: Ic1csc2cnc(Nc3ccc(N4CCOCC4)cc3)nc12] | 438.00 | C$_{16}$H$_{15}$IN$_4$OS | (CDCl$_3$, 300 MHz): δ 8.81 (s, 1H), 8.00 (s, 1H), 773 (d, J = 9.0 Hz, 2H), 7.22 (br s, 1 H), 6.97 (d, J = 9.0 Hz, 2 H), 3.88 (t, J = 4.8 Hz, 4 H), 3.14 (t, J = 4.8 Hz, 4H); | m/z 439.1 [M + H]$^+$ |
| 2 | 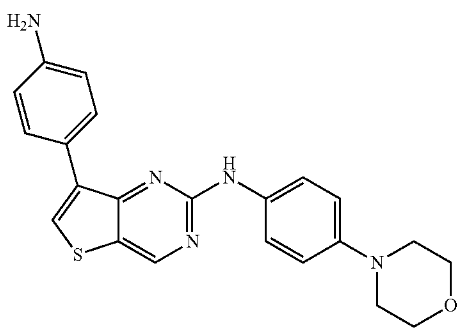 [SMILES: Nc1ccc(-c2csc3cnc(Nc4ccc(N5CCOCC5)cc4)nc23)cc1] | 403.15 | C$_{22}$H$_{21}$N$_5$OS | (CDCl$_3$, 300 MHz): δ 8.88 (s, 1 H), 7.86 (d, J = 8.7 Hz, 2 H), 7.81 (s, 1H), 7.65 (d, J = 9.0 Hz, 2 H), 7.09 (br s, 1 H), 6.93 (d, J = 9.0 Hz, 2 H), 6.80 (d, J = 8.4 Hz, 2 H), 3.89 (t, J = 4.5 Hz, 4 H), 3.80 (br s, 2 H), 3.13 (t, J = 4.5 Hz, 4 H); | m/z 404.3 [M + H]$^+$ |
| 3 | 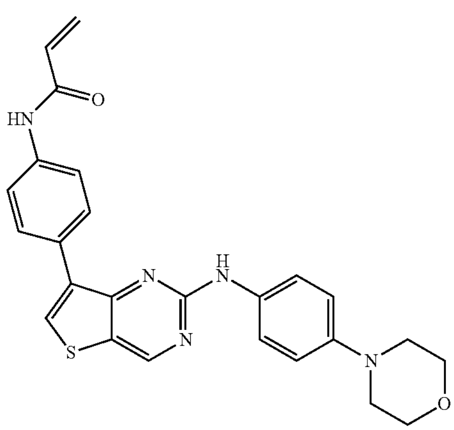 [SMILES: C=CC(=O)Nc1ccc(-c2csc3cnc(Nc4ccc(N5CCOCC5)cc4)nc23)cc1] | 457.16 | C$_{25}$H$_{23}$N$_5$O$_2$S | (DMSO-d$_6$, 300 MHz): δ 10.27 (br s, 1 H), 9.45 (br s, 1 H), 9.16 (s, 1 H), 8.48 (s, 1 H), 8.13 (d, J = 8.4 Hz, 2 H), 7.80 (d, J = 8.4 Hz, 2 H), 7.72 (d, J = 9.0 Hz, 2 H), 6.91 (d, J = 8.7 Hz, 2 H), 6.49 (dd, J = 17.4, 11.1 Hz, 1 H), 6.29 (d, J = 17.4 Hz, 1 H), 5.79 (d, J = 11.1 Hz, 1 H), 3.76 (t, J = 3.9 Hz, 4 H), 3.06 (t, J = 4.2 Hz, 4 H); | m/z 458.2 [M + H]$^+$ m/z 457.3 [M]$^+$ |

-continued

| No | Structure | Mol Weight | Formula | ¹H NMR data | LC-MS |
|---|---|---|---|---|---|
| 4 | 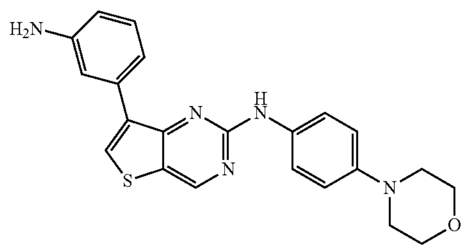 [SMILES: Nc1cccc(-c2csc3cnc(Nc4ccc(N5CCOCC5)cc4)nc23)c1] | 403.15 | $C_{22}H_{21}N_5OS$ | (DMSO-$d_6$, 300 MHz): δ 9.40 (br s, 1 H), 9.13 (s, 1 H), 8.32 (s, 1 H), 7.75 (d, J = 9.0 Hz, 2 H), 7.24-7.12 (m, 3 H), 6.90 (d, J = 9.0 Hz, 2 H), 6.93 (ddd, J = 9.0, 2.1, 1.2 Hz, 1 H), 5.06 (br s, 2 H), 3.74 (t, J = 4.8 Hz, 4 H), 3.03 (t, J = 4.8 Hz, 4 H); | m/z 404.3 [M + H]⁺ |
| 5 | 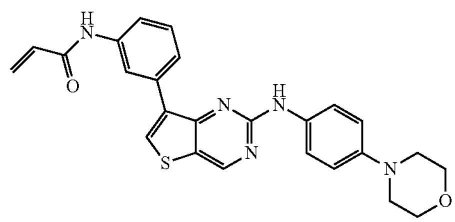 [SMILES: C=CC(=O)Nc1cccc(-c2csc3cnc(Nc4ccc(N5CCOCC5)cc4)nc23)c1] | 457.16 | $C_{25}H_{23}N_5O_2S$ | (DMSO-$d_6$, 300 MHz): δ 10.27 (br s, 1 H), 9.48 (br s, 1 H), 9.17 (s, 1 H), 8.44 (s, 1 H), 8.27 (s, 1 H), 7.80-7.40 (m, 5 H), 6.82 (d, J = 8.1 Hz, 2 H), 6.52 (dd, J = 18.0, 10.5 Hz, 1 H), 6.30 (d, J = 17.4 Hz, 1 H), 5.79 (d, J = 10.2 Hz, 1 H), 3.73 (br s, 4H), 2.99 (br s, 4 H); | m/z 458.2 [M + H]⁺ m/z 457.3 [M]⁺ |
| 7 | 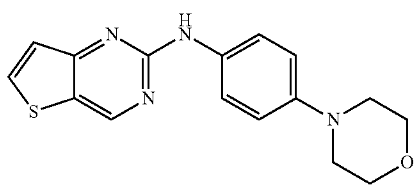 [SMILES: c1cc2nc(Nc3ccc(N4CCOCC4)cc3)ncc2s1] | 312.10 | $C_{16}H_{16}N_4OS$ | (DMSO-$d_6$, 300 MHz): δ 9.36 (s, 1H), 9.10 (s, 1H), 8.27 (d, J = 5.4 Hz, 1H), 7.67 (d, J = 9.3 Hz, 2H), 7.30 (d, J = 5.4 Hz, 1H), 6.90 (d, J = 8.7 Hz, 2H), 3.74 (m, 4H), 3.03 (m, 4H) | m/z 313.2 [M + H]⁺ |
| 8 | 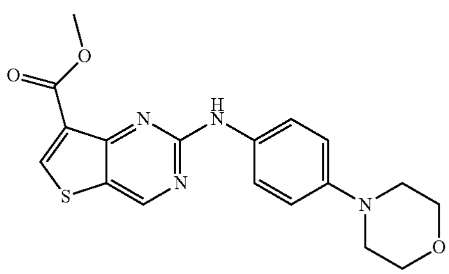 [SMILES: COC(=O)c1csc2cnc(Nc3ccc(N4CCOCC4)cc3)nc12] | 370.11 | $C_{18}H_{18}N_4O_3S$ | (DMSO-$d_6$, 300 MHz): δ 9.60 (s, 1H), 9.17 (s, 1H), 9.03 (s, 1H), 7.96 (d, J = 8.4 Hz, 2H), 6.92 (d, J = 9.0 Hz, 2H), 3.92 (s, 3H), 3.74 (m, 4H), 3.05 (m, 4H); | m/z 371.3 [M + H]⁺ |
| 9 | 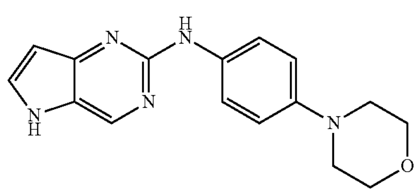 [SMILES: c1cc2nc(Nc3ccc(N4CCOCC4)cc3)ncc2[nH]1] | 295.14 | $C_{16}H_{17}N_5O$ | (DMSO-$d_6$, 300 MHz): δ 11.3 (br. s, 1H), 8.81 (d, J = 0.9 Hz, 1H), 8.58 (d, J = 0.9 Hz, 1H), 7.69 (d, J = 9.3 Hz, 2H), 7.64 (app t, 1H), 6.87 (d, J = 9.3 Hz, 2H), 6.29 (m, 1H), 3.74 (m, 4H), 3.01 (m, 4H); | m/z 296.3 [M + H]⁺ |
| 10 | 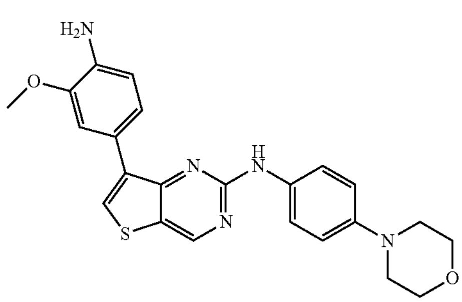 [SMILES: COc1cc(-c2csc3cnc(Nc4ccc(N5CCOCC5)cc4)nc23)ccc1N] | 433.16 | $C_{23}H_{23}N_5O_2S$ | (DMSO-$d_6$, 300 MHz): δ 9.39 (s, 1H), 9.10 (s, 1H), 8.25 (s, 1H), 7.72 (d, J = 9.1 Hz, 2H), 7.53 (d, J = 1.8 Hz, 1H), 7.50 (dd, J = 8.0, 1.8 Hz, 1H), 6.87 (d, J = 9.1 Hz, 2H), 6.73 (d, J = 8.0 Hz, 1H), 4.89 (br, s, 2H), 3.78 (s, 3H), 3.74 (m, 4H), 3.03 (m, 4H); | m/z 434.3 [M + H]⁺ |

-continued

| No | Structure | Mol Weight | Formula | ¹H NMR data | LC-MS |
|---|---|---|---|---|---|
| 11 | 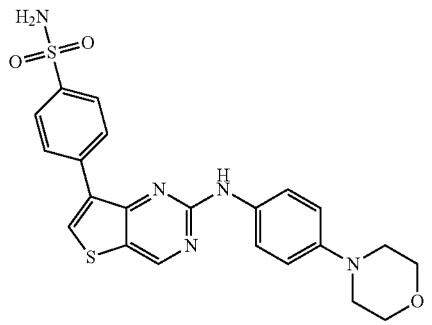 [SMILES: NS(=O)(=O)c1ccc(-c2csc3cnc(Nc4ccc(N5CCOCC5)cc4)nc23)cc1] | 467.11 | $C_{22}H_{21}N_5O_3S_2$ | (DMSO-$d_6$, 300 MHz): δ 9.49 (s, 1H), 9.18 (s, 1H), 8.69 (s, 1H), 8.31 (dt, J = 8.6, 2.0 Hz, 2H), 7.92 (dt, J = 8.6, 2.0 Hz, 2H), 7.68 (m, 2H), 7.41 (br s, 2H), 6.91 (m, 2H), 3.74 (m, 4H), 3.04 (m, 4H); | m/z 468.2 [M + H]⁺ |
| 12 | 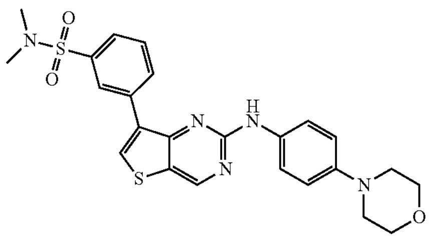 [SMILES: CN(C)S(=O)(=O)c1cccc(-c2csc3cnc(Nc4ccc(N5CCOCC5)cc4)nc23)c1] | 495.14 | $C_{24}H_{25}N_5O_3S_2$ | (DMSO-$d_6$, 300 MHz): δ 9.46 (s, 1H), 9.19 (s, 1H), 8.70 (s, 1H), 8.48 (dt, J = 7.1, 1.8 Hz, 1H), 8.24 (br, m, 1H), 7.80-7.77 (m, 2H), 7.67 (d, J = 9.1 Hz, 2H), 6.92 (d, J = 9.1 Hz, 2H), 3.73 (m, 4H), 3.03 (m, 4H), 2.65 (s, 6H); | m/z 496.3 [M + H]⁺ |
| 13 | 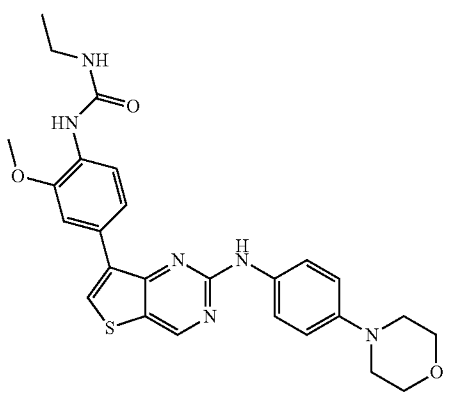 [SMILES: CCNC(=O)Nc1ccc(-c2csc3cnc(Nc4ccc(N5CCOCC5)cc4)nc23)cc1OC] | 504.19 | $C_{26}H_{28}N_6O_3S$ | (DMSO-$d_6$, 300 MHz): δ 9.41 (s, 1H), 9.13 (s, 1H), 8.40 (s, 1H), 8.18 (d, J = 8.5 Hz, 1H), 7.95 (br, s, 1H), 7.71-7.68 (m, 3H), 7.55 (dd, J = 8.4, 1.8 Hz, 1H), 6.87 (m, 3H), 3.83 (s, 3H), 3.74 (m, 4H), 3.09 (m, 2H), 3.03 (m, 4H), 1.06 (t, J = 7.2 Hz, 3H); | m/z 505.3 [M + H]⁺ |
| 14 | 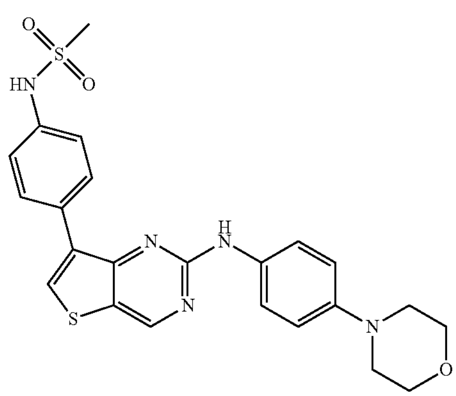 [SMILES: CS(=O)(=O)Nc1ccc(-c2csc3cnc(Nc4ccc(N5CCOCC5)cc4)nc23)cc1] | 481.12 | $C_{23}H_{23}N_5O_3S_2$ | (DMSO-$d_6$, 300 MHz): δ 9.84 (br, s, 1H), 9.43 (br, s, 1H), 9.14 (s, 1H), 8.46 (s, 1H), 8.10 (d, J = 8.8 Hz, 2H), 7.69 (d, J = 9.1 Hz, 2H), 7.32 (d, J = 8.8 Hz, 2H), 6.89 (d, J = 9.1 Hz, 2H), 3.75 (m, 4H), 3.04 (m, 7H); | m/z 482.3 [M + H]⁺ |

-continued

| No | Structure | Mol Weight | Formula | ¹H NMR data | LC-MS |
|---|---|---|---|---|---|
| 15 | 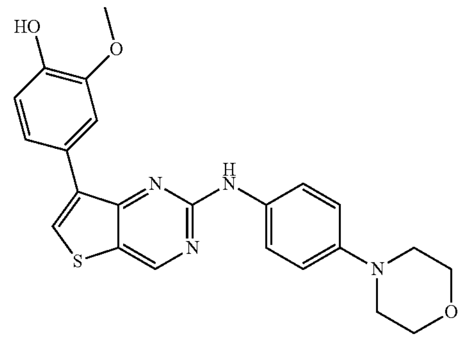 [SMILES: COc1cc(-c2csc3cnc(Nc4ccc(N5CCOCC5)cc4)nc23)ccc1O] | 434.14 | $C_{23}H_{22}N_4O_3S$ | (DMSO-$d_6$, 300 MHz): δ 9.41 (br, s, 1H), 9.12 (s, 1H), 9.11 (s, 1H), 8.35 (s, 1H), 7.71 (d, J = 9.1 Hz, 2H), 7.64 (d, J = 2.0 Hz, 1H), 7.54 (dd, J = 8.2, 2.0 Hz, 1H), 6.88 (d, J = 8.2 Hz, 1H), 6.87 (d, J = 9.1 Hz, 2H), 3.78 (s, 3H), 3.75 (m, 4H), 3.03 (m, 4H); | m/z 435.2 [M + H]⁺ |
| 16 | 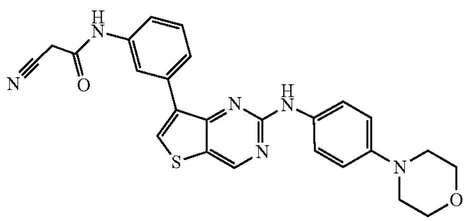 [SMILES: N#CCC(=O)Nc1cccc(-c2csc3cnc(Nc4ccc(N5CCOCC5)cc4)nc23)c1] | 470.15 | $C_{25}H_{22}N_6O_2S$ | (DMSO-$d_6$, 300 MHz): δ 10.42 (s, 1H), 9.46 (s, 1H), 9.17 (s, 1H), 8.43 (s, 1H), 8.09 (s, 1H), 7.81 (d, J = 4.8 Hz, 1H), 7.72 (d, J = 5.1Hz, 2H), 7.59 (d, J = 5.4 Hz, 1H), 7.49 (dd, J = 5.1, 4.8 Hz, 1H), 6.86 (d, J = 5.4 Hz, 2H), 3.93 (s, 2H), 3.74 (m, 4H), 3.03 (m, 4H); | m/z 471.3 [M + H]⁺ |
| 17 | 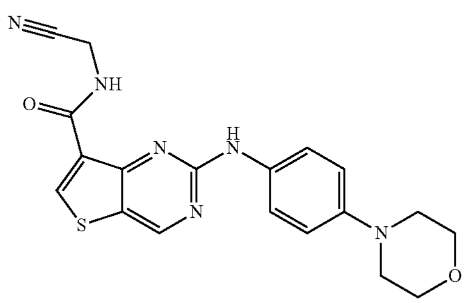 | 394.12 | $C_{19}H_{18}N_6O_2S$ | (DMSO-$d_6$, 300 MHz): δ 9.75 (br s, 1H), 9.62 (s, 1H), 9.22 (s, 1H), 8.98 (s, 1H), 7.50 (d, J = 5.4 Hz, 2H), 7.01 (d, J = 5.4 Hz, 2H), 4.45 (d, J = 3.6 Hz, 2H), 3.75 (m, 4H), 3.08 (m, 4H); | m/z 395.3 [M + H]⁺ |
| 18 | 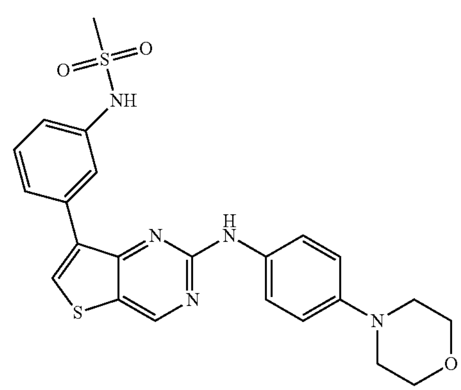 [SMILES: CS(=O)(=O)Nc1cccc(-c2csc3cnc(Nc4ccc(N5CCOCC5)cc4)nc23)c1] | 481.12 | $C_{23}H_{23}N_5O_3S_2$ | (DMSO-$d_6$, 300 MHz): δ 9.83 (br, s, 1H), 9.43 (s, 1H), 9.16 (s, 1H), 8.44 (s, 1H), 7.82 (m, 1H), 7.78 (m, 1H), 7.71 (d, J = 9.1 Hz, 2H), 7.46 (t, J = 7.9 Hz, 1H), 7.25 (m, 1H), 6.92 (d, J = 9.1 Hz, 2H), 3.73 (m, 4H), 3.05 (m, 4H), 3.00 (s, 3H); | m/z 482.3 [M + H]⁺ |

-continued

| No | Structure | Mol Weight | Formula | ¹H NMR data | LC-MS |
|---|---|---|---|---|---|
| 19 | 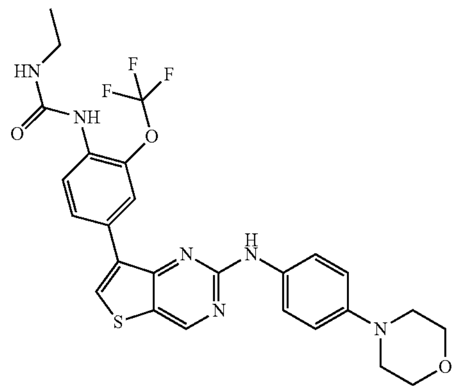 [SMILES: CCNC(=O)Nc1ccc(-c2csc3cnc(Nc4ccc(N5CCOCC5)cc4)nc23)cc1OC(F)(F)F] | 558.17 | $C_{26}H_{25}F_3N_6O_3S$ | (DMSO-d$_6$, 300 MHz): δ 9.47 (br, s, 1H), 9.15 (s, 1H), 8.55 (s, 1H), 8.37 (d, J = 8.8 Hz, 1H), 8.30 (m, 1H), 8.27 (br, s, 1H), 7.97 (dd, J = 8.8, 2.0 Hz, 1H), 7.68 (d, J = 9.1 Hz, 2H), 6.92-6.88 (m, 3H), 3.74 (m, 4H), 3.14 (m, 2H), 3.04 (m, 4H), 1.08 (t, J = 7.2 Hz, 3H); | m/z 559.3 [M + H]$^+$ |
| 20 | 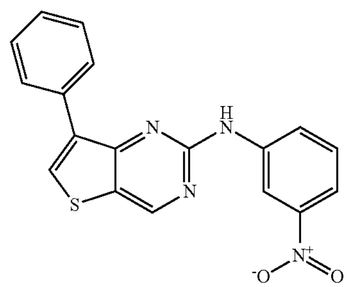 | 348.07 | $C_{18}H_{12}N_4O_2S$ | (DMSO-d$_6$, 300 MHz): δ 10.3 (br s, 1 H), 9.34 (s, 1 H), 8.94 (t, J = 2.4 Hz, 1 H), 8.62 (s, 1 H), 8.15 (m, 1 H), 8.08 (m, 2 H), 7.80 (m, 1 H), 7.60-7.49 (m, 3 H), 7.42 (m, 1 H); | m/z 349.2 [M + H]$^+$ |
| 21 | 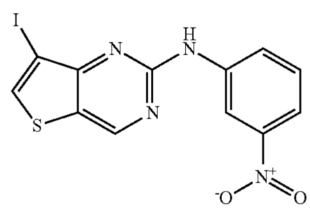 | 397.93 | $C_{12}H_7IN_4O_2S$ | (DMSO-d$_6$, 300 MHz): δ 10.4 (br s, 1 H), 9.26 (s, 1 H), 9.23 (s, 1 H), 8.64 (s, 1 H), 8.26 (d, J = 8.1 Hz, 1 H), 7.81 (d, J = 8.1 Hz, 1 H), 7.59 (t, J = 8.1 Hz, 1 H) | m/z 399.0 [M + H]$^+$ |
| 22 | 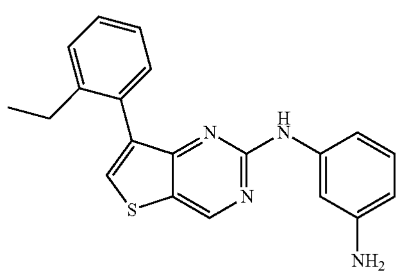 [SMILES: CCc1ccccc1-c1csc2cnc(Nc3cccc(N)c3)nc12] | 346.13 | $C_{20}H_{18}N_4S$ | NMR (DMSO-d$_6$, 300 MHz): δ 9.31 (br s, 1 H), 9.18 (s, 1 H), 8.22 (s, 1 H), 7.39 (m, 2 H), 7.31 (m, 2 H), 7.00 (m, 1 H), 6.94 (m, 1 H), 6.80 (t, J = 7.8 Hz, 1 H), 6.14 (m, 1 H), 4.72 (br s, 2 H), 2.56 (q, J = 7.8 Hz, 2 H), 1.01 (t, J = 7.8 Hz, 3 H); | m/z 347.3 [M + H]$^+$ |
| 25 | 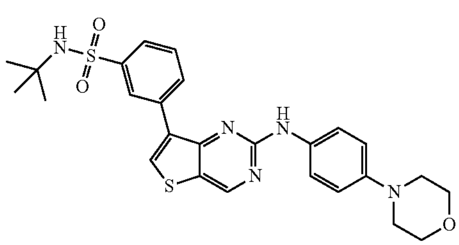 [SMILES: CC(C)(C)NS(=O)(=O)c1cccc(-c2csc3cnc(Nc4ccc(N5CCOCC5)cc4)nc23)c1] | 523.17 | $C_{26}H_{29}N_5O_3S_2$ | (DMSO-d$_6$, 300 MHz): δ 9.47 (s, 1H), 9.19 (s, 1H), 8.61 (s, 1H), 8.48 (br s, 1H), 8.31 (br d, J = 8.4 Hz, 1H), 7.87 (br d, J = 8.1 Hz, 1H), 7.74-7.69 (m, 3H), 7.58 (s, 1H), 6.94 (d, J = 9.0 Hz, 2H), 3.74 (m, 4H), 3.03 (m, 4H), 1.12 (s, 9H); | m/z 524.2 [M + H]$^+$ m/z 522.4 [M + H]$^+$ |
| 26 | 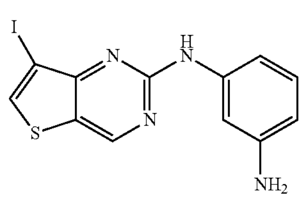 [SMILES: Nc1cccc(Nc2ncc3scc(I)c3n2)c1] | 367.96 | $C_{12}H_9IN_4S$ | (DMSO-d$_6$, 300 MHz): δ 9.53 (br s, 1 H), 9.11 (s, 1 H), 8.54(s, 1 H), 7.28 (m, 1 H), 7.21 (t, J = 2.1 Hz, 1 H), 6.94 (t, J = 8.4 Hz, 1 H), 6.22 (m, 1 H), 4.87 (br s, 2 H); | m/z 369.1 [M + H]$^+$ |

-continued

| No | Structure | Mol Weight | Formula | ¹H NMR data | LC-MS |
|---|---|---|---|---|---|
| 28 | 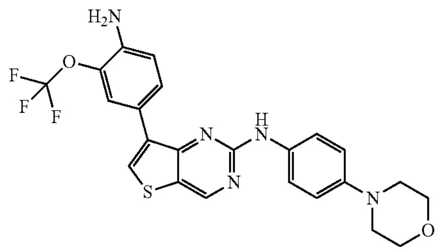 [SMILES: Nc1ccc(-c2csc3cnc(Nc4ccc(N5CCOCC5)cc4)nc23)cc1OC(F)(F)F] | 487.13 | $C_{23}H_{20}F_3N_5O_2S$ | (Acetone-$d_6$, 300 MHz): δ 9.06 (s, 1H), 8.52 (bs, 1H), 8.25 (s, 1H), 8.12 (bs, 1H), 7.92 (dd, J = 8.5, 2.1 Hz, 1H), 7.82 (d, J = 9.1 Hz, 2H), 7.03 (d, J = 8.5 Hz, 1H), 6.97 (d, J = 9.1 Hz, 2H), 3.80 (m, 4H), 3.10 (m, 4H); | m/z 488.2 [M + H]⁺ |
| 29 | 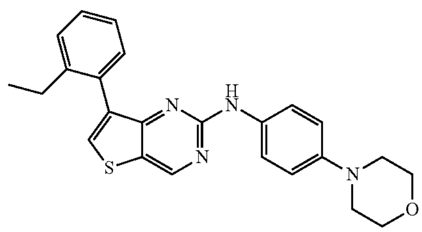 [SMILES: CCc1ccccc1-c1csc2cnc(Nc3ccc(N4CCOCC4)cc3)nc12] | 416.17 | $C_{24}H_{24}N_4OS$ | (Acetone-$d_6$, 300 MHz): δ 9.09 (s, 1H), 8.45 (bs, 1H), 8.05 (s, 1H), 7.73 (d, J = 9.1 Hz, 2H), 7.43-7.40 (m, 2H), 7.38-7.27 (m, 2H), 6.84 (d, J = 9.1 Hz, 2H), 3.76 (m, 4H), 3.04 (m, 4H), 2.64 (q, J = 7.6 Hz, 2H), 1.04 (t, J = 7.6 Hz, 3H): | m/z 417.3 [M + H]⁺ |
| 30 | 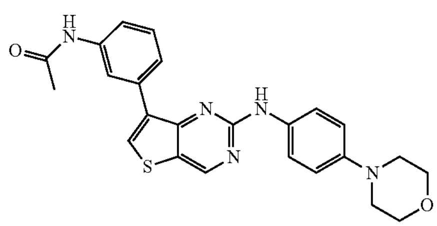 [SMILES: CC(=O)Nc1cccc(-c2csc3cnc(Nc4ccc(N5CCOCC5)cc4)nc23)c1] | 445.16 | $C_{24}H_{23}N_5O_2S$ | (DMSO-$d_6$, 300 MHz): δ 10.0 (bs, 1H), 9.46 (bs, 1H), 9.15 (s, 1H), 8.39 (s, 1H), 8.14 (m, 1H), 7.75-7.70 (m, 3H), 7.60 (m, 1H), 7.42 (t, J = 7.9 Hz, 1H), 6.85 (d, J = 9.1 Hz, 2H), 3.73 (m, 4H), 3.02 (m, 4H), 2.07 (s, 3H); | m/z 446.2 [M + H]⁺ |
| 31 | 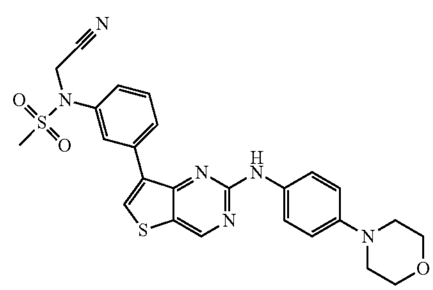 | 520.14 | $C_{25}H_{24}N_6O_3S_2$ | (DMSO-$d_6$, 300 MHz): δ 9.48 (br, s, 1H), 9.17 (s, 1H), 8.60 (s, 1H), 8.19 (d, J = 8.7 Hz, 2H), 7.70 (d, J = 9.1 Hz, 2H), 7.59 (d, J = 8.7 Hz, 2H), 6.90 (d, J = 9.1 Hz, 2H), 4.95 (s, 2H), 3.73 (m, 4H), 3.20 (s, 3H), 3.03 (m, 4H); | m/z 521.3 [M + H]⁺ |
| 32 | 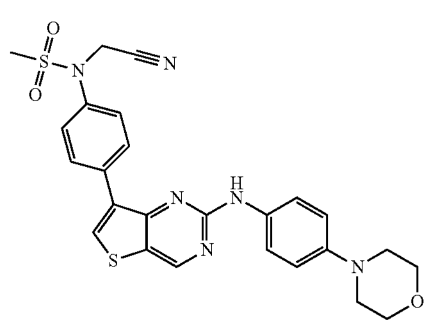 [SMILES: CS(=O)(=O)N(CC#N)c1ccc(-c2csc3cnc(Nc4ccc(N5CCOCC5)cc4)nc23)cc1] | 520.14 | $C_{25}H_{24}N_6O_3S_2$ | (DMSO-$d_6$, 300 MHz): δ 9.44 (br, s, 1H), 9.18 (s, 1H), 8.63 (s, 1H), 8.26 (m, 1H), 8.12 (m, 1H), 7.69 (d, J = 9.1 Hz, 2H), 7.63 (d, J = 7.9 Hz, 1H), 7.50 (m, 1H), 6.93 (d, J = 9.1 Hz, 2H), 4.95 (s, 2H), 3.74 (m, 4H), 3.17 (s, 3H), 3.06 (m, 4H); | m/z 521.3 [M + H]⁺ |

-continued

| No | Structure | Mol Weight | Formula | ¹H NMR data | LC-MS |
|---|---|---|---|---|---|
| 33 | 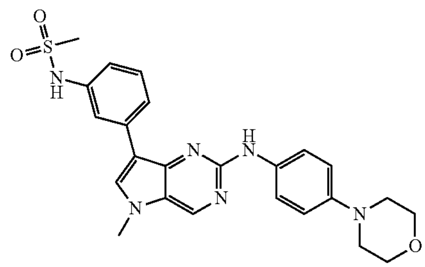 [SMILES: Cn1cc(-c2cccc(NS(C)(=O)=O)c2)c2nc(Nc3ccc(N4CCOCC4)cc3)ncc21] | 478.18 | $C_{24}H_{26}N_6O_3S$ | (CD$_3$CN, 300 MHz): δ 8.62 (s, 1H), 8.06 (app t, 1H), 7.93 (m, 1H), 7.80 (s, 1H), 7.70 (d, J = 9.0 Hz, 2H), 7.53 (bs, 1H), 7.41 (app t, 1H), 7.12 (m, 1H), 6.98 (d, J = 9.3 Hz, 2H), 3.85 (s, 3H), 3.79 (app t, 4H), 3.08 (app t, 4H), 2.96 (s, 3H). Missing 1H-water exchange (wet solvent); | m/z 479.3 [M + H]⁺ |
| 34 | 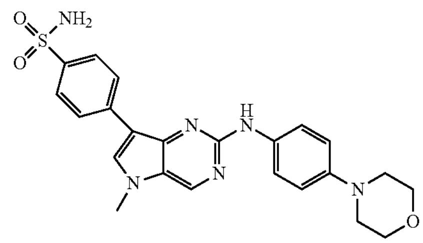 [SMILES: Cn1cc(-c2ccc(S(N)(=O)=O)cc2)c2nc(Nc3ccc(N4CCOCC4)cc3)ncc21] | 464.16 | $C_{23}H_{24}N_6O_3S$ | (DMSO-d$_6$, 300 MHz): δ 9.12 (s, 1H), 8.81 (s, 1H), 8.35 (d, J = 8.7 Hz, 2H), 8.29 (s, 1H), 7.85 (d, J = 8.7 Hz, 2H), 7.76 (d, J = 9.3 Hz, 2H), 7.27 (s, 2H), 6.93 (d, J = 9.0 Hz, 2H), 3.89 (s, 3H), 3.75 (app t, 4H), 3.04 (app t, 4H); | m/z 465.2 [M + H]⁺ |
| 35 | 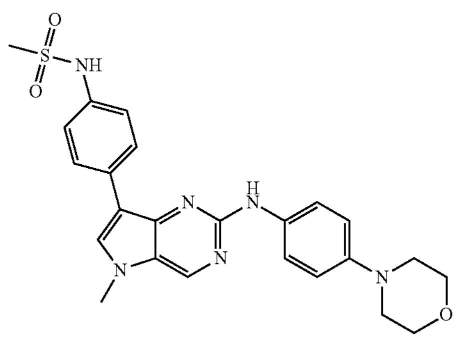 [SMILES: Cn1cc(-c2ccc(NS(C)(=O)=O)cc2)c2nc(Nc3ccc(N4CCOCC4)cc3)ncc21] | 478.18 | $C_{24}H_{26}N_6O_3S$ | (CD$_3$CN, 300 MHz): δ 8.61 (s, 1H), 8.13 (d, J = 5.4 Hz, 2H), 7.78 (s, 1H), 7.68 (d, J = 5.4 Hz, 2H), 7.54-7.60 (m, 2H), 7.30 (d, J = 5.4 Hz, 2H), 6.96 (d, J = 5.4 Hz, 2H), 3.84 (s, 3H), 3.77-3.81 (m, 4H), 3.06-3.09 (m, 4H), 2.96 (s, 3H) | m/z 479.3 [M + H]⁺. |
| 36 | 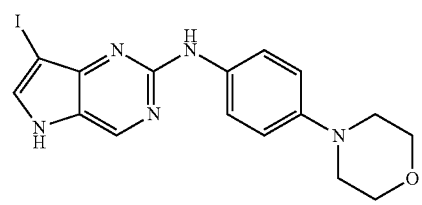 [SMILES: Ic1c[nH]c2cnc(Nc3ccc(N4CCOCC4)cc3)nc12] | 421.04 | $C_{16}H_{16}IN_5O$ | (CD$_3$OD, 300 MHz): δ 8.46 (s, 1H), 7.87 (s, 1H), 7.72 (d, J = 9.3, 2H), 7.65 (s, 1H), 6.97 (d, J = 9.3, 2H), 3.84 (m, 4H), 3.09 (m, 4H). NH not observed | m/z 422.2 [M + H]⁺ |
| 37 | 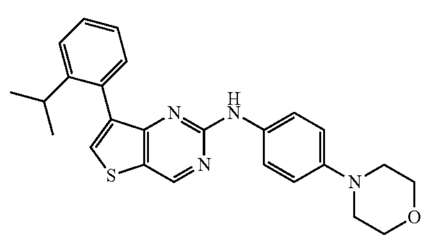 [SMILES: CC(C)c1ccccc1-c1csc2cnc(Nc3ccc(N4CCOCC4)cc3)nc12] | 430.18 | $C_{25}H_{26}N_4OS$ | (CDCl$_3$, 300 MHz): δ 8.93 (s, 1H), 7.73 (s, 1H), 7.46 (m, 4H), 7.29 (m, 2H), 7.04 (s, 1H), 6.83 (d, J = 8.9, 2H), 3.86 (m, 4H), 3.08 (m, 4H), 2.95 (m, 1H), 1.16 (d, J = 6.9, 6H) | m/z 430.1 [M]⁺ 431.1 [M + H]⁺ |
| 38 | 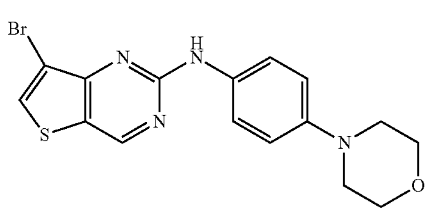 [SMILES: Brc1csc2cnc(Nc3ccc(N4CCOCC4)cc3)nc12] | 390.01 | $C_{16}H_{15}BrN_4OS$ | (CDCl$_3$, 300 MHz): δ 8.86 (s, 1H), 7.86 (s, 1H), 7.67 (d, J = 8.9, 2H), 7.22 (s, 1H), 6.96 (d, J = 9.1, 2H), 3.88 (m, 4H), 3.14 (m, 4H) | m/z 391.0, 393.0 [M + H]⁺ |

-continued

| No | Structure | Mol Weight | Formula | ¹H NMR data | LC-MS |
|---|---|---|---|---|---|
| 39 | 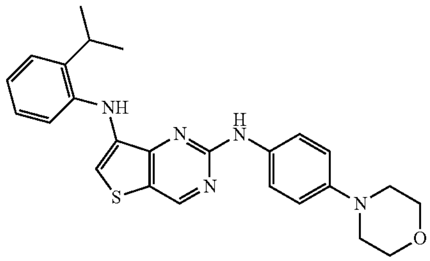 [SMILES: CC(C)c1ccccc1Nc1csc2cnc(Nc3ccc(N4CCOCC4)cc3)nc12] | 445.19 | $C_{25}H_{27}N_5OS$ | (CDCl$_3$, 300 MHz): δ 8.82 (s, 1H), 7.62 (m, 2H), 7.51 (dd, J = 1.1, 8.0, 1H), 7.33 (dd, J = 1.6, 7.8, 1H), 7.22 (m, 1H), 7.13 (s, 1H), 7.04 (m, 1H), 6.98 (s, 1H), 6.94 (m, 2H), 6.88 (m, 1H), 3.89 (m, 4H), 3.24 (m, 1H), 3.13 (m, 4H), 1.34 (d, J = 6.9, 6H) | m/z 445.1 [M]$^+$ 446.1 [M + H]$^+$ |
| 40 | 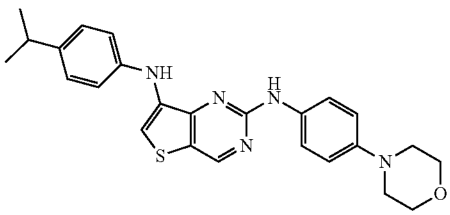 [SMILES: CC(C)c1ccc(Nc2csc3cnc(Nc4ccc(N5CCOCC5)cc4)nc23)cc1] | 445.19 | $C_{25}H_{27}N_5OS$ | (CDCl$_3$, 300 MHz): δ 8.81 (s, 1H), 7.57 (m, 2H), 7.18 (m, 4H), 7.09 (s, 1H), 7.07 (s, 1H), 6.96 (m, 2H), 6.74 (s, 1H), 3.88 (m, 4H), 3.15 (m, 4H), 2.90 (m, 1H), 1.26 (d, J = 6.9, 6H) | m/z 445.1 [M]$^+$ 446.1 [M + H]$^+$ |
| 41 | 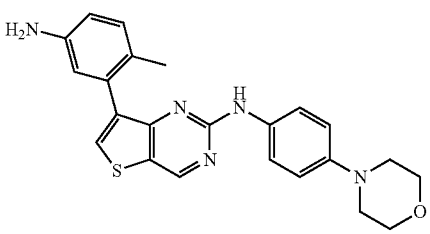 [SMILES: Cc1ccc(N)cc1-c1csc2cnc(Nc3ccc(N4CCOCC4)cc3)nc12] | 417.16 | $C_{23}H_{23}N_5OS$ | (CDCl$_3$, 300 MHz): δ 8.91 (s, 1H), 7.74 (s, 1H), 7.56 (m, 2H), 7.12 (m, 2H), 6.87 (m, 2H), 6.82 (d, J = 2.5, 1H), 6.70 (dd, J = 2.5, 8.0, 1H), 3.86 (m, 4H), 3.62 (s, 2H), 3.09 (m, 4H), 2.18 (s, 3H) | m/z 418.1 [M + H]$^+$ |
| 42 | 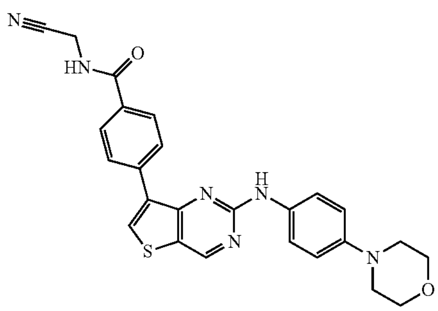 [SMILES: N#CCNC(=O)c1ccc(-c2csc3cnc(Nc4ccc(N5CCOCC5)cc4)nc23)cc1] | 470.15 | $C_{25}H_{22}N_6O_2S$ | (DMSO-d$_6$, 400 MHz): δ 9.50 (s, 1H), 9.29 (m, 1H), 9.18 (s, 1H), 8.70 (s, 1H), 8.31 (d, J = 8.5 Hz, 2H), 7.99 (d, J = 8.6 Hz, 2H), 7.70 (d, J = 9.1 Hz, 2H), 6.93 (d, J = 8.8 Hz, 2H), 4.35 (d, J = 5.7 Hz, 2H), 3.75 (t, J = 4.4 Hz, 4H), 3.05 (t, J = 4.4 Hz, 4H) | m/z 471.1 [M + H]$^+$ |
| 43 | 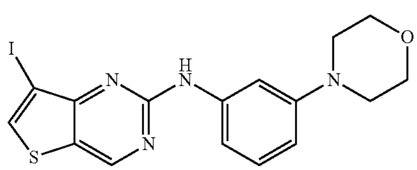 [SMILES: Ic1csc2cnc(Nc3cccc(N4CCOCC4)c3)nc12] | 438.00 | $C_{16}H_{15}IN_4OS$ | (CDCl$_3$, 400 MHz): δ 8.84 (s, 1H), 8.04 (s, 2H), 7.34 (s b, 1H), 7.42-7.22 (m, 1H), 6.94 (d, J = 6.4 Hz, 1H), 6.63 (d, J = 6.4 Hz, 1H), 4.41 (d, J = 4.8 Hz, 4H), 3.32 (t, J = 4.8 Hz, 4H) | m/z 438.9 [M + H]$^+$ |
| 44 | 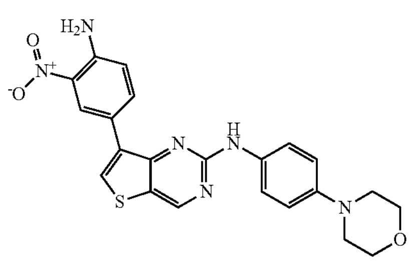 | 448.13 | $C_{22}H_{20}N_6O_3S$ | (DMSO-d$_6$, 300 MHz): δ 9.50 (s, 1H), 9.16 (s, 1H), 8.80 (d, J = 2.1 Hz, 1H), 8.47 (s, 1H), 8.07 (dd, J = 2.1, 8.9 Hz, 1H), 7.72 (d, J = 8.9 Hz, 2H), 7.57 (s, 2H), 7.15 (d, J = 8.9 Hz, 1H), 6.86 (d, J = 9.1 Hz, 2H), 3.75 (m, 4H), 3.02 (m, 4H) | m/z 449.0 [M + H]$^+$ |

| No | Structure | Mol Weight | Formula | ¹H NMR data | LC-MS |
|---|---|---|---|---|---|
| 45 | 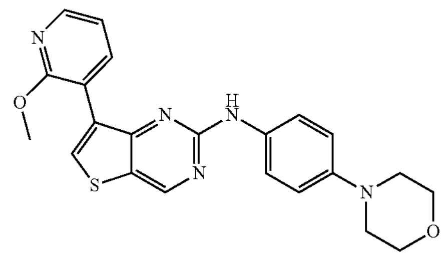 [SMILES: COc1ncccc1-c1csc2cnc(Nc3ccc(N4CCOCC4)cc3)nc12] | 419.14 | $C_{22}H_{21}N_5O_2S$ | (DMSO-d$_6$, 300 MHz): δ 9.46 (s, 1H), 9.16 (s, 1H), 8.55 (s, 1H), 8.46 (dd, J = 1.9, 7.4 Hz, 1H), 8.23 (dd, J = 1.9, 4.9 Hz, 1H), 7.66 (d, J = 9.1 Hz, 2H), 7.18 (dd, J = 4.9, 7.4 Hz, 1H), 6.86(d, J = 9.1 Hz, 2H), 3.93 (s, 3H), 3.74 (m, 4H), 3.03 (m, 4H) | m/z 420.0 [M + H]⁺ |
| 46 | 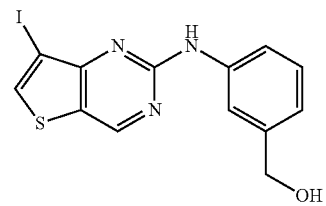 [SMILES: OCc1cccc(Nc2ncc3scc(I)c3n2)c1] | 382.96 | $C_{13}H_{10}IN_3OS$ | (DMSO-d$_6$, 300 MHz): δ 9.79 (br s, 1H), 9.13 (s, 1H), 8.55 (s, 1H), 8.00 (s b, 1H), 7.90-7.88 (m, 1H), 7.28-7.23 (m, 1H), 6.97-6.94 (m, 1H), 4.51 (s, 2H) 1H obscured under water peak | m/z 383.9 [M + H]⁺ |
| 47 | 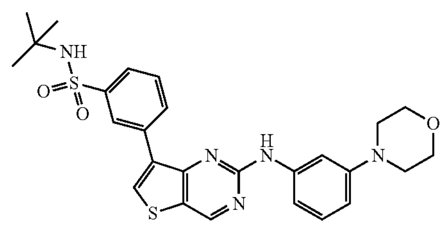 [SMILES: CC(C)(C)NS(=O)(=O)c1cccc(-c2csc3cnc(Nc4cccc(N5CCOCC5)c4)nc23)c1] | 523.17 | $C_{26}H_{29}N_5O_3S_2$ | (CDCl$_3$, 300 MHz): δ 9.52 (s, 1H), 9.23 (s, 1H), 8.59 (s, 1H), 8.37 (m, 1H), 8.33-8.30 (m, 1H), 7.88-7.85 (m, 1H), 7.69 (t, J = 7.6 Hz, 1H), 7.60 (s, 1H), 7.40-7.37 (m, 1H), 7.33 (m, 1H), 7.16 (t, J = 8.0 Hz, 1H), 6.55 (dd, J = 8.3, 1.9 Hz, 1H), 3.66 (t, J = 5.0 Hz, 4H), 2.96 (t, J = 4.8 Hz, 4H), 1.10 (s, 9H) | m/z 524.1 [M + H]⁺ |
| 48 | 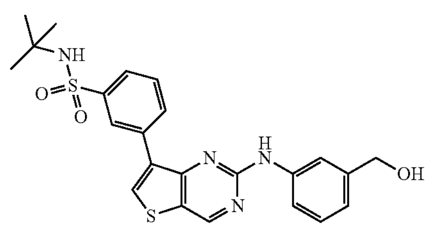 [SMILES: CC(C)(C)NS(=O)(=O)c1cccc(-c2csc3cnc(Nc4cccc(CO)c4)nc23)c1] | 468.13 | $C_{23}H_{24}N_4O_3S_2$ | (CDCl$_3$, 500 MHz): δ 8.93 (s, 1H), 8.63 (t, J = 2.0 Hz, 1H), 8.23-8.21 (m, 1H), 8.07 (s, 1H), 7.90-7.89 (m, 1H), 7.83 (m, 1H), 7.62-7.57 (m, 1H), 7.52-7.49 (m, 1H), 7.37 (t, J = 7.8 Hz, 1H), 7.33 (br s, 1H), 7.07 (m, 1H), 4.67 (br s, 2H), 4.58 (s, 1H), 1.22 (s, 9H). Missing 1H-water exchange (wet solvent) | m/z 469.0 [M + H]⁺ |
| 49 | 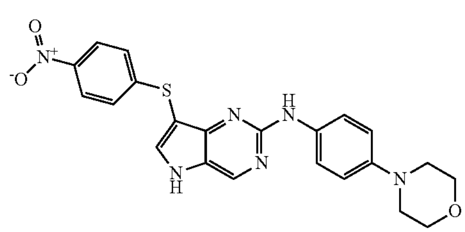 | 448.13 | $C_{22}H_{20}N_6O_3S$ | (CDCl$_3$, 300 MHz): δ 8.66 (s, 1H), 8.05 (d, J = 9.3 Hz, 2H), 7.71 (s, 1H), 7.44 (d, J = 9.0 Hz, 2H), 7.23 (d, J = 8.7 Hz, 2H), 7.11 (m, 1H), 6.99 (s, 1H), 6.81 (d, J = 9.3 Hz, 2H), 3.86 (m, 4H), 3.07 (m, 4H) | m/z 449.0 [M + H]⁺ |
| 50 | 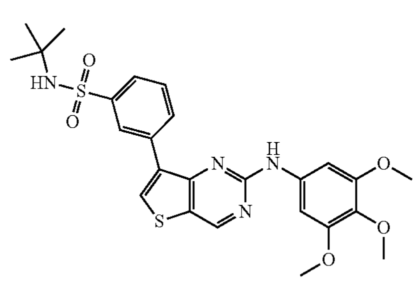 [SMILES: COc1cc(Nc2ncc3scc(-c4cccc(S(=O)(=O)NC(C)(C)C)c4)c3n2)cc(OC)c1OC] | 528.15 | $C_{25}H_{28}N_4O_5S_2$ | (DMSO-d$_6$, 300 MHz): δ 9.55 (s, 1H), 9.26 (s, 1H), 8.58 (s, 1H), 8.33 (d, J = 8.1 Hz, 1H), 8.24 (br. s, 1H), 7.87-7.82 (m, 1H), 7.69-7.63 (m, 1H), 7.59 (s, 1H), 7.18 (s, 2H), 3.60 (s, 3H), 3.59 (s ,6H), 1.10 (s, 9H) | m/z 529.1 [M + H]⁺ |

-continued

| No | Structure | Mol Weight | Formula | ¹H NMR data | LC-MS |
|---|---|---|---|---|---|
| 51 | 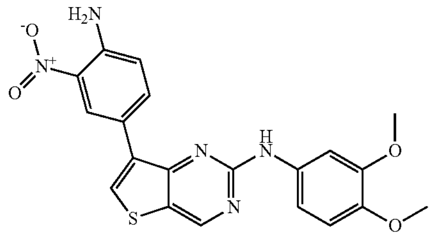 | 423.10 | $C_{20}H_{17}N_5O_4S$ | (DMSO-$d_6$, 300 MHz): δ 9.47 (s, 1H), 9.18 (s, 1H), 8.73 (d, J = 1.8 Hz, 1H), 8.47 (s, 1H), 8.08 (dd, J = 1.9, 8.8 Hz, 1H), 7.57 (s, 2H), 7.49 (dd, J = 2.2, 8.8 Hz, 1H), 7.37 (d, J = 2.3 Hz, 1H), 7.14 (d, J = 8.9 Hz, 1H), 6.84 (d, J = 8.9 Hz, 1H), 3.72 (s, 3H), 3.64 (s, 3H) | m/z 424.0 [M + H]⁺ |
| 52 | 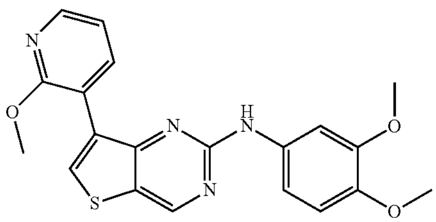 [SMILES: COc1ccc(Nc2ncc3scc(-c4cccnc4OC)c3n2)cc1OC] | 394.11 | $C_{20}H_{18}N_4O_3S$ | (DMSO-$d_6$, 300 MHz): δ 9.48 (s, 1H), 9.18 (s, 1H), 8.50 (s, 1H), 8.32 (dd, J = 1.8, 7.3 Hz, 1H), 8.22 (dd, J = 1.9, 4.9 Hz, 1H), 7.52 (d, J = 2.5 Hz, 1H), 7.25 (dd, J = 2.4, 8.8 Hz, 1H), 7.13 (dd, J = 4.9, 7.4 Hz, 1H), 6.83 (d, J = 8.9 Hz, 1H), 3.89 (s, 3H), 3.71 (s, 3H), 3.53 (s, 3H) | m/z 395.0 [M + H]⁺ |
| 53 | 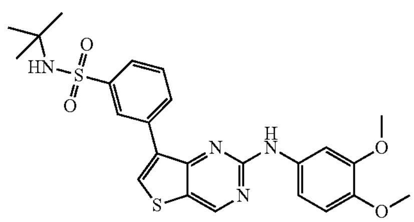 [SMILES: COc1ccc(Nc2ncc3scc(-c4cccc(S(=O)(=O)NC(C)(C)C)c4)c3n2)cc1OC] | 498.14 | $C_{24}H_{26}N_4O_4S_2$ | (DMSO-$d_6$, 300 MHz): δ 9.49 (s, 1H), 9.22 (s, 1H), 8.61 (s, 1H), 8.39 (s, 1H), 8.32 (d, J = 7.8 Hz, 1H), 7.87 (d, J = 8.5 Hz, 1H), 7.69 (t, J = 7.9 Hz, 1H), 7.59 (s, 1H), 7.46 (dd, J = 2.5, 8.7 Hz, 1H), 7.38 (d, J = 2.3 Hz, 1H), 6.94 (d, J = 8.9 Hz, 1H), 3.72 (s, 3H), 3.61 (s, 3H), 1.11 (s, 9H) | m/z 499.0 [M + H]⁺ |
| 54 | 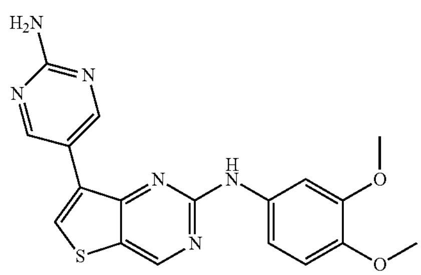 [SMILES: COc1ccc(Nc2ncc3scc(-c4cnc(N)nc4)c3n2)cc1OC] | 380.11 | $C_{18}H_{16}N_6O_2S$ | (DMSO-$d_6$, 300 MHz): δ 9.50 (s, 1H), 9.18 (s, 1H), 8.92 (s, 2H), 8.46 (s, 1H), 7.54 (d, J = 2.5 Hz, 1H), 7.19 (dd, J = 2.4, 8.8 Hz, 1H), 6.85 (d, J = 8.9 Hz, 1H), 6.83 (s, 2H), 3.72 (s, 3H), 3.69 (s, 3H) | m/z 381.0 [M + H]⁺ |
| 55 | 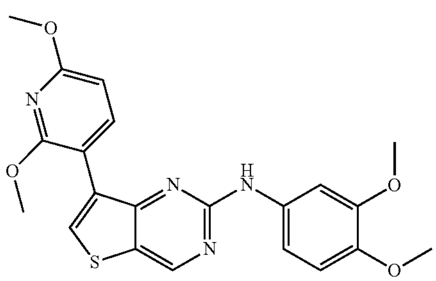 | 424.12 | $C_{21}H_{20}N_4O_4S$ | (DMSO-$d_6$, 300 MHz): δ 9.45 (s, 1H), 9.16 (s, 1H), 8.38 (s, 1H), 8.31 (d, J = 8.0 Hz, 1H), 7.53 (d, J = 2.5 Hz, 1H), 7.27 (dd, J = 2.5, 8.7 Hz, 1H), 6.85 (d, J = 8.7 Hz, 1H), 6.51 (d, J = 8.2 Hz, 1H), 3.94 (s, 3H), 3.91 (s, 3H), 3.71 (s, 3H), 3.56 (s, 3H) | m/z 425.0 [M + H]⁺ |
| 56 | 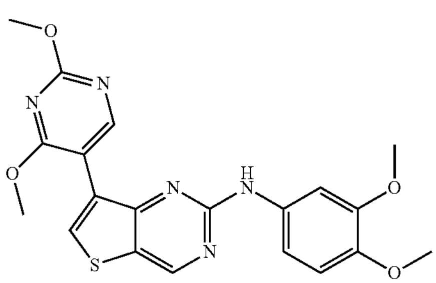 | 425.12 | $C_{20}H_{19}N_5O_4S$ | (DMSO-$d_6$, 300 MHz): δ 9.50 (s, 1H), 9.18 (s, 1H), 9.01 (s, 1H), 8.47 (s, 1H), 7.57 (d, J = 2.5 Hz, 1H), 7.17 (dd, J = 2.5, 8.7 Hz, 1H), 6.84 (d, J = 8.7 Hz, 1H), 3.98 (s, 3H), 3.96 (s, 3H), 3.71 (s, 3H), 3.61 (s, 3H) | m/z 426.0 [M + H]⁺ |

-continued

| No | Structure | Mol Weight | Formula | ¹H NMR data | LC-MS |
|---|---|---|---|---|---|
| 57 | 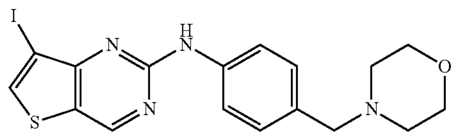 [SMILES: Ic1csc2cnc(Nc3ccc(CN4CCOCC4)cc3)nc12] | 452.02 | $C_{17}H_{17}IN_4OS$ | (DMSO/CDCl$_3$, 300 MHz): δ 8.85 (s, 1H), 8.04 (s, 1H), 7.81 (d, J = 8.1 Hz, 2H), 7.35 (br s, 1H), 7.34 (d, J = 8.1 Hz, 2H), 3.72 (t, J = 4.6 Hz, 4H), 3.49 (s, 2H), 2.47 (t, J = 4.6 Hz, 4H) | m/z 452.9 [M + H]$^+$ |
| 58 | 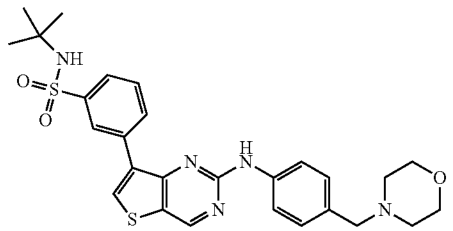 [SMILES: CC(C)(C)NS(=O)(=O)c1cccc(-c2csc3cnc(Nc4ccc(CN5CCOCC5)cc4)nc23)c1] | 537.19 | $C_{27}H_{31}N_5O_3S_2$ | (CDCl$_3$, 500 MHz): δ 8.92 (s, 1H), 8.65 (t, J = 1.7 Hz, 1H), 8.21 (m, 1H), 8.03 (s, 1H), 7.89 (m, 1H), 7.66 (d, J = 8.5 Hz, 2H), 7.55 (t, J = 7.9 Hz, 1H), 7.41 (br s, 1H), 7.33 (d, J = 8.5 Hz, 2H), 4.95 (s, 1H), 3.72 (t, J = 4.6 Hz, 4H), 3.50 (s, 2H), 2.47 (t, J = 4.6 Hz, 4H), 1.25 (s, 9H) | m/z 538.2 [M + H]$^+$ |
| 59 | 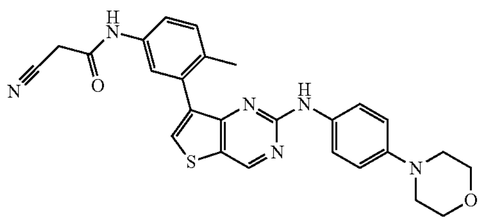 [SMILES: Cc1ccc(NC(=O)CC#N)cc1-c1csc2cnc(Nc3ccc(N4CCOCC4)cc3)nc12] | 484.17 | $C_{26}H_{24}N_6O_2S$ | (DMSO-d$_6$, 300 MHz): δ 10.33 (s, 1H), 9.42 (s, 1H), 9.16 (s, 1H), 8.25 (s, 1H), 7.62 (d, J = 9.3 Hz, 2H), 7.59 (m, 1H), 7.53 (dd, J = 8.1, 2.4 Hz, 1H), 7.31 (d, J = 8.4 Hz, 1H), 6.76 (d, J = 9.0 Hz, 2H), 3.88 (s, 2H), 3.72 (m, 4H), 2.99 (m, 4H), 2.19 (s, 3H) | m/z 485.1 [M + H]$^+$ |
| 60 | 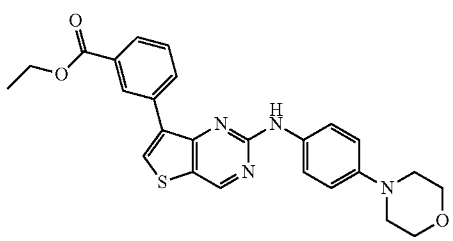 [SMILES: CCOC(=O)c1cccc(-c2csc3cnc(Nc4ccc(N5CCOCC5)cc4)nc23)c1] | 460.16 | $C_{25}H_{24}N_4O_3S$ | (DMSO-d$_6$, 300 MHz): δ 9.53 (s, 1H), 9.19 (s, 1H), 8.65 (br.s, 1H), 8.63 (s, 1H), 8.28 (br. d, 8.1 Hz, 1H), 8.00 (br.d, 8.4 Hz, 1H), 7.73 (d, J = 9.3 Hz, 2H), 7.67 (dd, J = 7.8, 7.8 Hz, 1H), 6.84 (d, J = 9.3 Hz, 2H), 4.34 (q, J = 7.2 Hz, 2H), 3.73 (m, 4H), 3.01 (m, 4H), 1.29 (t, J = 7.2 Hz, 3H) | m/z 461.1 [M + H]$^+$ |
| 61 | 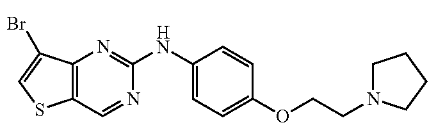 [SMILES: Brc1csc2cnc(Nc3ccc(OCCN4CCCC4)cc3)nc12] | 418.05 | $C_{18}H_{19}BrN_4OS$ | (DMSO-d$_6$, 300 MHz): δ 9.69 (s, 1H); 9.15 (s, 1H); 8.47 (s, 1H); 7.80 (d, J = 9 Hz, 2H); 6.88 (d, J = 9 Hz, 2H); 4.03 (t, J = 6 Hz, 2H); 2.76 (t, J = 6 Hz, 2H); 2.57 (m*, under DMSO signal, 4H); 1.67 (m, 4H) | m/z 419.0, 421.0 [M + H]$^+$ |
| 62 | 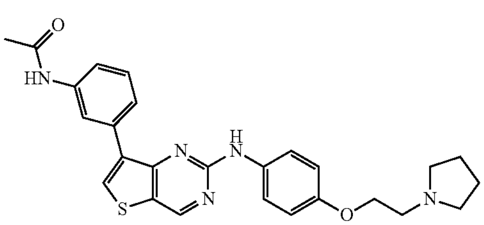 [SMILES: CC(=O)Nc1cccc(-c2csc3cnc(Nc4ccc(OCCN5CCCC5)cc4)nc23)c1] | 473.19 | $C_{26}H_{27}N_5O_2S$ | (DMSO-d$_6$, 300 MHz): δ 10.06 (s, 1H); 9.53 (s, 1H); 9.17 (s, 1H); 8.41 (s, 1H); 8.15 (s, 1H); 7.76 (d, J = 9 Hz, 2H); 7.67 (d, J = 8 Hz, 1H); 7.60 (d, J = 8 Hz, 1H); 7.42 (t, J = 8 Hz, 1H); 6.85 (d, J = 9 Hz, 2H); 4.07 (t, J = 6 Hz, 2H); 2.96 (m, 2H); 2.71 (m, 4H); 2.08 (s, 3H); 1.74 (m, 4H) | m/z 474.1 [M + H]$^+$ |
| 63 | 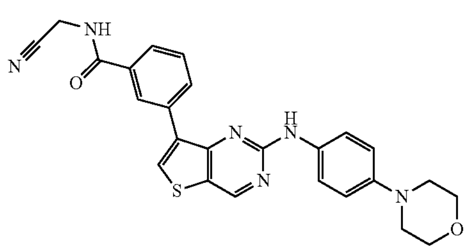 [SMILES: N#CCNC(=O)c1cccc(-c2csc3cnc(Nc4ccc(N5CCOCC5)cc4)nc23)c1] | 470.15 | $C_{25}H_{22}N_6O_2S$ | (DMSO-d$_6$, 300 MHz): δ 9.49 (s, 1H), 9.28 (br.t, J = 5.4 Hz, 1H), 9.19 (s, 1H), 8.59 (s, 1H), 8.50 (br.s, 1H), 8.29 (br.d, J = 7.8 Hz, 1H), 7.89 (br.d, J = 8.1 Hz, 1H), 7.71 (d, J = 9.0 Hz, 2H), 7.66 (dd, J = 8.1, 8.1 Hz, 1H), 6.87 (d, J = 9.0 Hz, 2H), 4.36 (d, J = 5.4 Hz, 2H), 3.74 (m, 4H), 3.03 (m, 4H) | m/z 471.1 [M + H]$^+$ |

| No | Structure | Mol Weight | Formula | ¹H NMR data | LC-MS |
|---|---|---|---|---|---|
| 64 | 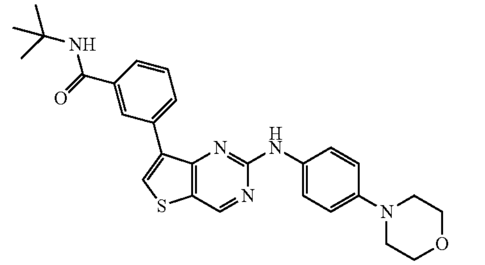 [SMILES: CC(C)(C)NC(=O)c1cccc(-c2csc3cnc(Nc4ccc(N5CCOCC5)cc4)nc23)c1] | 487.20 | $C_{27}H_{29}N_5O_2S$ | (CDCl$_3$, 300 MHz): δ 8.92 (s, 1H), 8.33 (m, 1H), 8.10 (m, 1H), 8.01 (s, 1H), 7.77 (m, 1H), 7.63 (d, J = 8.7 Hz, 2H), 7.53 (dd, J = 1.5, 7.5 Hz, 1H), 7.23 (br.s, 1H), 6.90 (d, J = 9.0 Hz, 2H), 6.02 (br.s, 1H), 3.86 (m, 4H), 3.11 (m, 4H), 1.43 (s, 9H) | m/z 488.1 [M + H]⁺ |
| 65 | 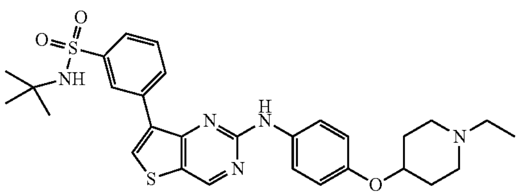 [SMILES: CCN1CCC(Oc2ccc(Nc3ncc4scc(-c5cccc(S(=O)(=O)NC(C)(C)C)c5)c4n3)cc2)CC1] | 565.22 | $C_{29}H_{35}N_5O_3S_2$ | (CDCl$_3$, 500 MHz): δ 8.92 (s, 1H), 8.65 (t, J = 2.0 Hz, 1H), 8.23-8.21 (m, 1H), 8.07 (s, 1H), 7.90-7.89 (m, 1H), 7.58 (d, J = 9.2 Hz, 2H), 7.57 (t, J = 5.1 Hz, 1H), 7.14 (brs, 1H), 6.97 (d, J = 9.2 Hz, 2H), 4.57 (br s, 1H), 4.35-4.28 (m, 1H), 2.82-2.75 (m, 2H), 2.45 (q, J = 4.5 Hz, 2H), 2.35-2.30 (m, 2H), 2.10-2.0 (m, 2H), 1.90-1.80 (m, 2H), 1.22 (s, 9H), 1.11 (t, J = 4.2 Hz, 3H) | m/z 566.1 [M + H]⁺ |
| 66 | 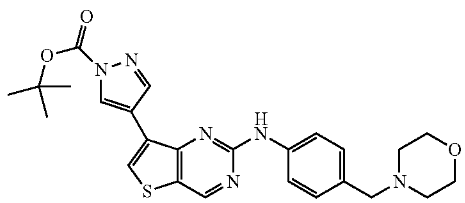 [SMILES: CC(C)(C)OC(=O)n1cc(-c2csc3cnc(Nc4ccc(CN5CCOCC5)cc4)nc23)cn1] | 492.19 | $C_{25}H_{28}N_6O_3S$ | (DMSO/CDCl$_3$, 300 MHz): δ 8.98 (d, J = 0.7 Hz, 1H), 8.93 (s, 1H), 8.26 (d, J = 0.7 Hz, 1H), 7.95 (s, 1H), 7.68 (d, J = 8.5 Hz, 2H), 7.37 (d, J = 8.5 Hz, 2H), 7.27 (br s, 1H), 3.73 (t, J = 4.7 Hz, 4H), 3.51 (s, 2H), 2.48 (m, 4H), 1.71 (s, 9H) | m/z 493.1 [M + H]⁺ |
| 67 | 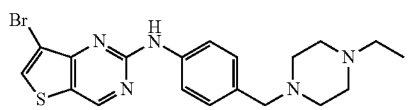 [SMILES: CCN1CCN(Cc2ccc(Nc3ncc4scc(Br)c4n3)cc2)CC1] | 431.08 | $C_{19}H_{22}BrN_5S$ | (CDCl$_3$, 500 MHz): δ 8.89 (s, 1H), 7.88 (s, 1H), 7.74 (d, J = 8.5 Hz, 2H), 7.35 (br s, 1H), 7.32 (d, J = 8.4 Hz, 2H), 3.50 (s, 2H), 2.60-2.45 (m, 8H), 2.42 (q, J = 7.1 Hz, 2H), 1.08 (t, J = 7.3 Hz, 3H) | m/z 432.0, 434.0 [M + H]⁺ |
| 68 | 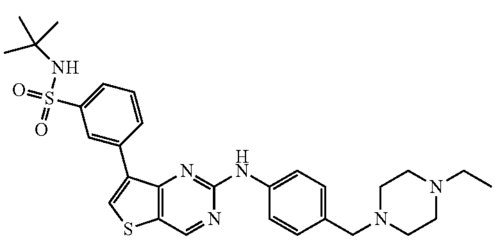 [SMILES: CCN1CCN(Cc2ccc(Nc3ncc4scc(-c5cccc(S(=O)(=O)NC(C)(C)C)c5)c4n3)cc2)CC1] | 564.23 | $C_{29}H_{36}N_6O_2S_2$ | (CDCl$_3$, 500 MHz): δ 8.96 (s, 1H), 8.55 (t, J = 1.8 Hz, 1H), 8.30-8.28 (m, 1H), 8.09 (s, 1H), 7.91-7.89 (m, 1H), 7.66 (d, J = 8.5 Hz, 2H), 7.60 (t, J = 7.8 Hz, 1H), 7.33 (d, J = 8.4 Hz, 2H), 7.28 (br s, 1H), 4.53 (s, 1H), 3.52 (s, 2H), 2.65-2.48 (m, 8H), 2.47-2.46 (m, 2H), 1.24 (s, 9H), 1.11 (t, J = 7.3 Hz, 3H) | m/z 565.1 [M + H]⁺ |
| 69 | 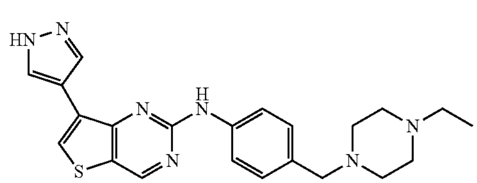 [SMILES: CCN1CCN(Cc2ccc(Nc3ncc4scc(-c5cn[nH]c5)c4n3)cc2)CC1] | 419.19 | $C_{22}H_{25}N_7S$ | (CDCl$_3$, 300 MHz): δ 8.88 (s, 1H), 8.03 (s, 2H), 7.82 (s, 1H), 7.44 (d, J = 8.2 Hz, 2H), 7.29 (d, J = 8.2 Hz, 2H), 7.06 (br s, 1H), 3.86 (s, 2H), 2.70-2.40 (m, 8H), 2.57 (q, J = 7.2 Hz, 2H), 1.22 (t, J = 7.3 Hz, 3H). Missing 1H-water exchange (wet solvent) | m/z 420.1 [M + H]⁺ |
| 70 | 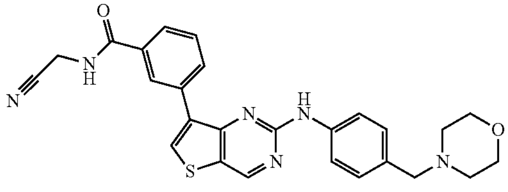 [SMILES: N#CCNC(=O)c1cccc(-c2csc3cnc(Nc4ccc(CN5CCOCC5)cc4)nc23)c1] | 484.17 | $C_{26}H_{24}N_6O_2S$ | (DMSO/CDCl$_3$, 300 MHz): δ 8.97 (s, 1H), 8.56 (br s, 1H), 8.30 (t, J = 5.5 Hz, 1H), 8.24-8.21 (m, 1H), 8.12 (s, 1H), 7.95-7.93 (m, 1H), 7.80 (br s, 1H), 7.72 (d, J = 8.7 Hz, 2H), 7.59 (dd, J = 7.8, 7.8 Hz, 1H), 7.27 (d, J = 8.8 Hz, 2H), 4.35 (d, J = 5.6 Hz, 2H), 3.70 (t, J = 4.6 Hz, 4H), 3.48 (s, 2H), 2.45 (t, J = 4.6 Hz, 4H) | m/z 485.1 [M + H]⁺ |

-continued

| No | Structure | Mol Weight | Formula | ¹H NMR data | LC-MS |
|---|---|---|---|---|---|
| 71 | 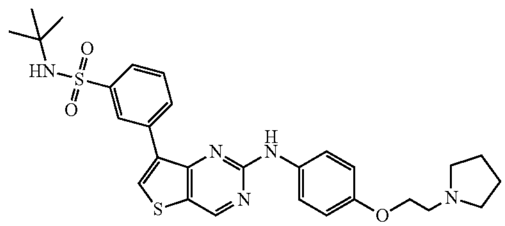 [SMILES: CC(C)(C)NS(=O)(=O)c1cccc(-c2csc3cnc(Nc4ccc(OCCN5CCCC5)cc4)nc23)c1] | 551.20 | $C_{28}H_{33}N_5O_3S_2$ | (CDCl$_3$, 300 MHz): δ 8.91 (s, 1H), 8.64 (dd, J = 1.7, 1.7 Hz, 1H), 8.22 (d, J = 7.8 Hz, 1H), 8.07 (s, 1H), 7.89 (d, J = 8.7 Hz, 1H), 7.64-7.52 (m, 3H), 7.16 (s, 1H), 6.98 (d, J = 8.9 Hz, 2H), 4.63 (s, 1H), 4.20 (t, J = 5.8 Hz, 2H), 3.00 (t, J = 5.7 Hz, 2H), 2.84-2.65 (m, 4H), 1.96-1.78 (m, 4H), 1.22 (s, 9H) | m/z 552.1 [M + H]⁺ |
| 72 | 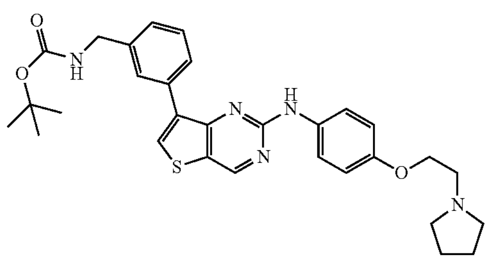 [SMILES: CC(C)(C)OC(=O)NCc1cccc(-c2csc3cnc(Nc4ccc(OCCN5CCCC5)cc4)nc23)c1] | 545.25 | $C_{30}H_{35}N_5O_3S$ | (CDCl$_3$, 300 MHz): δ 8.91 (s, 1H), 7.97 (s, 1H), 7.95-7.86 (m, 2H), 7.61 (d, J = 8.9 Hz, 2H), 7.45 (dd, J = 7.8, 7.8 Hz, 1H), 7.33 (d, J = 7.5 Hz, 1H), 7.13 (s, 1H), 6.92 (d, J = 8.9 Hz, 2H), 4.91 (s, 1H), 4.41 (d, J = 5.7 Hz, 2H), 4.18 (t, J = 5.7 Hz, 2H), 2.99 (t, J = 5.7 Hz, 2H), 2.85-2.65 (m, 4H), 1.95-1.79 (m, 4H), 1.46 (s, 9H) | m/z 546.2 [M + H]⁺ |
| 73 | 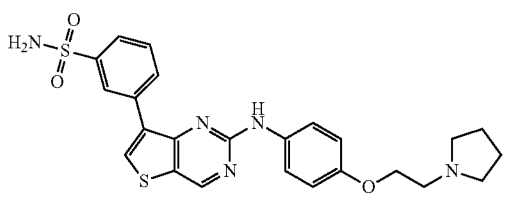 [SMILES: NS(=O)(=O)c1cccc(-c2csc3cnc(Nc4ccc(OCCN5CCCC5)cc4)nc23)c1] | 495.14 | $C_{24}H_{25}N_5O_3S_2$ | (CDCl$_3$/CD3OD, 300 MHz): δ 8.77 (s, 1H), 8.43 (s, 1H), 8.09-7.98 (m, 2H), 7.77 (d, J = 8.5 Hz, 1H), 7.51-7.40 (m, 3H), 6.80 (d, J = 9.1 Hz, 2H), 4.00 (t, J = 5.6 Hz, 2H), 2.92-2.78 (m, 2H), 2.70-2.51 (m, 4H), 1.80-1.64 (m, 4H). Missing 3 H-solvent exchange | m/z 496.0 [M + H]⁺ |
| 74 | 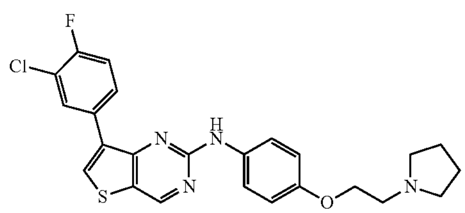 [SMILES: Fc1ccc(-c2csc3cnc(Nc4ccc(OCCN5CCCC5)cc4)nc23)cc1Cl] | 468.12 | $C_{24}H_{22}ClFN_4OS$ | (DMSO-d$_6$, 300 MHz): δ 9.57 (s, 1H), 9.19 (s, 1H), 8.66 (s, 1H), 8.50 (dd, J = 7.5, 2 Hz, 1H), 8.06 (m, 1H), 7.71 (d, J = 9 Hz, 2H), 7.56 (t, J = 9 Hz, 1H), 6.91 (d, J = 9 Hz, 2H), 4.04 (t, J = 6 Hz, 2H), 2.78 (t, J = 6 Hz, 2H), 2.57 (m* with DMSO, 4H), 1.69 (m, 4H). | m/z 469.0 [M + H]⁺ |
| 75 | 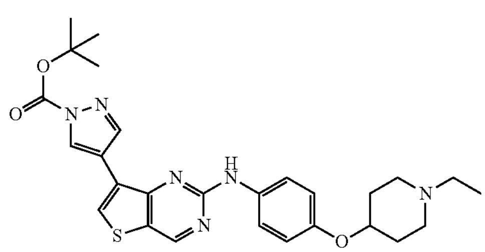 [SMILES: CCN1CCC(Oc2ccc(Nc3ncc4scc(-c5cnn(C(=O)OC(C)(C)C)c5)c4n3)cc2)CC1] | 520.23 | $C_{27}H_{32}N_6O_3S$ | (CDCl$_3$, 300 MHz): δ 9.02 (d, J = 0.7 Hz, 1H), 8.89 (s, 1H), 8.23 (d, J = 0.7 Hz, 1H), 7.93 (s, 1H), 7.60 (d, J = 8.9 Hz, 2H), 7.11 (br s, 1H), 7.00 (d, J = 8.9 Hz, 2H), 4.45-4.30 (m, 1H), 2.90-2.75 (m, 2H), 2.52 (q, J = 7.3 Hz, 2H), 2.50-2.40 (m, 2H), 2.20-2.15 (m, 2H), 2.00-1.80 (m, 2H), 1.7 (s, 9H), 1.22 (t, J = 7.2 Hz, 3H) | m/z 521.1 [M + H]⁺ |
| 76 | 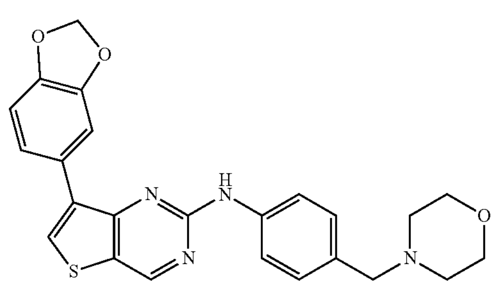 [SMILES: c1cc(Nc2ncc3scc(-c4ccc5c(c4)OCO5)c3n2)ccc1CN1CCOCC1] | 446.14 | $C_{24}H_{22}N_4O_3S$ | (CDCl$_3$, 300 MHz): δ 8.93 (s, 1H), 7.88 (s, 1H), 7.70 (d, J = 8.2 Hz, 2H), 7.55 (d, J = 1.5 Hz, 1H), 7.52 (dd, J = 8.2, 1.5 Hz, 1H), 7.29 (d, J = 8.9 Hz, 2H), 7.27 (br s, 1H), 6.93 (d, J = 7.8 Hz, 1H), 6.05 (s, 2H), 3.71 (t, J = 4.7 Hz, 4H), 3.48 (s, 2H), 2.46 (t, J = 4.7 Hz, 4H) | m/z 447.0 [M + H]⁺ |

-continued

| No | Structure | Mol Weight | Formula | ¹H NMR data | LC-MS |
|---|---|---|---|---|---|
| 77 | 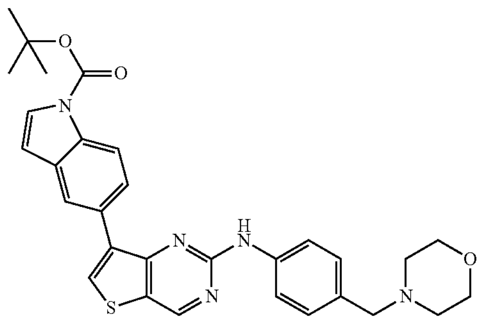 [SMILES: CC(C)(C)OC(=O)n1ccc2cc(-c3csc4cnc(Nc5ccc(CN6CCOCC6)cc5)nc34)ccc21] | 541.21 | $C_{30}H_{31}N_5O_3S$ | (CDCl$_3$, 300 MHz): δ 8.95 (s, 1H), 8.37 (d, J = 1.5 Hz, 1H), 8.25 (d, J = 8.7 Hz, 1H), 8.00 (s, 1H), 7.89 (dd, J = 8.7, 1.5 Hz, 1H), 7.74 (d, J = 8.2 Hz, 2H), 7.67 (d, J = 3.6 Hz, 1H), 7.28 (br s, 1H), 7.28 (d, J = 8.0 Hz, 2H), 6.66 (d, J = 3.6 Hz, 1H), 3.71 (t, J = 4.6 Hz, 4H), 3.48 (s, 2H), 2.46 (t, J = 4.6 Hz, 4H), 1.72 (s, 9H) | m/z 542.1 [M + H]⁺ |
| 78 | 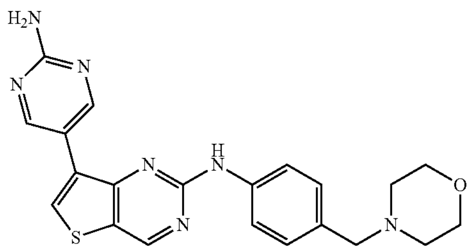 [SMILES: Nc1ncc(-c2csc3cnc(Nc4ccc(CN5CCOCC5)cc4)nc23)cn1] | 419.15 | $C_{21}H_{21}N_7OS$ | (DMSO-d$_6$, 300 MHz): δ 9.70 (s, 1H), 9.20 (s, 1H), 8.96 (s, 2H), 8.48 (s, 1H), 7.78 (d, J = 8.3 Hz, 2H), 7.19 (d, J = 8.5 Hz, 2H), 6.86 (s, 2H), 3.56 (t, J = 4.5 Hz, 4H), 3.39 (s, 2H), 2.34 (t, J = 4.3 Hz, 4H) | m/z 420.0 [M + H]⁺ |
| 79 | 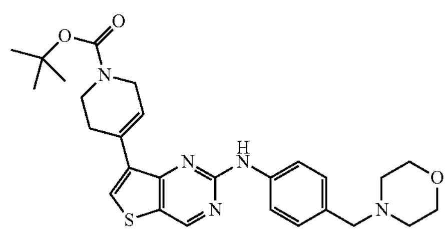 [SMILES: CC(C)(C)OC(=O)N1CC=C(c2csc3cnc(Nc4ccc(CN5CCOCC5)cc4)nc23)CC1] | 507.23 | $C_{27}H_{33}N_5O_3S$ | (CDCl$_3$, 300 MHz): δ 8.89 (s, 1H), 7.65 (s, 1H), 7.63 (d, J = 8.6 Hz, 2H), 7.30 (d, J = 8.2 Hz, 2H), 7.25 (m, 2H), 4.18-4.17 (m, 2H), 3.72 (t, J = 4.6 Hz, 4H), 3.70-3.69 (m, 2H), 3.48 (s, 2H), 2.64 (m, 2H), 2.46 (t, J = 4.6 Hz, 4H), 1.51 (s, 9H) | m/z 508.1 [M + H]⁺ |
| 80 | 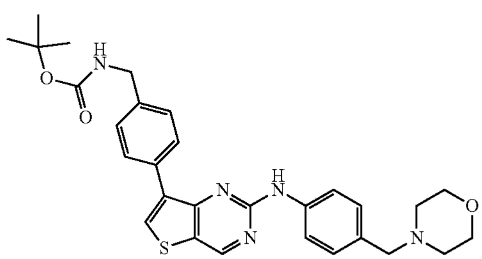 [SMILES: CC(C)(C)OC(=O)NCc1ccc(-c2csc3cnc(Nc4ccc(CN5CCOCC5)cc4)nc23)cc1] | 531.23 | $C_{29}H_{33}N_5O_3S$ | (CDCl$_3$, 300 MHz): δ 8.94 (s, 1H), 7.99 (d, J = 8.2 Hz, 2H), 7.97 (s, 1H), 7.70 (d, J = 8.4 Hz, 2H), 7.42 (d, J = 8.2, Hz, 2H), 7.29 (d, J = 8.3 Hz, 2H), 7.27 (br s, 1H), 4.93 (br s, 1H), 4.40 (d, J = 5.9 Hz, 2H), 3.72 (t, J = 4.6 Hz, 4H), 3.49 (s, H), 2.46 (t, J = 4.6 Hz, 4H), 1.50 (s, 9H) | m/z 532.1 [M + H]⁺ |
| 81 | 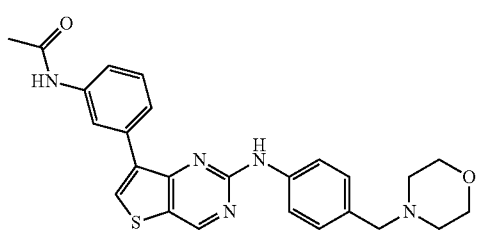 [SMILES: CC(=O)Nc1cccc(-c2csc3cnc(Nc4ccc(CN5CCOCC5)cc4)nc23)c1] | 459.17 | $C_{25}H_{25}N_5O_2S$ | (DMSO/CDCl$_3$, 300 MHz): δ 9.79 (br s, 1H), 9.17 (br s, 1H), 9.01 (s, 1H), 8.18 (m, 1H), 8.12 (s, 1H), 7.85 (d, J = 8.6, Hz, 2H), 7.73-7.72 (m, 1H), 7.70 (m, 1H), 7.40 (t, J = 7.9 Hz, 1H), 7.20 (d, J = 8.4 Hz, 2H), 3.65 (t, J = 4.6 Hz, 4H), 3.44 (s, 2H), 2.42 (t, J = 4.6 Hz, 4H), 2.17 (s, 3H) | m/z 460.0 [M + H]⁺ |
| 82 | 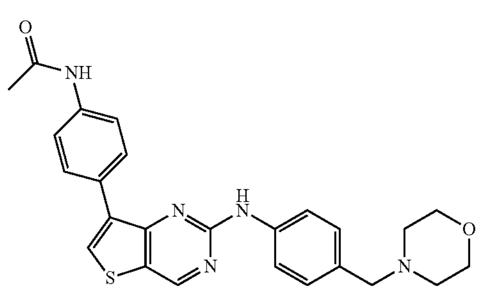 [SMILES: CC(=O)Nc1ccc(-c2csc3cnc(Nc4ccc(CN5CCOCC5)cc4)nc23)cc1] | 459.17 | $C_{25}H_{25}N_5O_2S$ | (DMSO/CDCl$_3$, 300 MHz): δ 9.52 (br s, 1H), 8.97 (s, 1H), 8.59 (br s, 1H), 7.99 (s, 1H), 7.99 (d, J = 8.8 Hz, 2H), 7.80 (d, J = 8.6 Hz, 2H), 7.73 (d, J = 8.7, Hz, 2H), 7.23 (d, J = 8.6 Hz, 2H), 3.68 (t, J = 4.6 Hz, 4H), 3.47 (s, 2H), 2.44 (t, J = 4.6 Hz, 4H), 2.19 (s, 3H) | m/z 460.1 [M + H]⁺ |

-continued

| No | Structure | Mol Weight | Formula | ¹H NMR data | LC-MS |
|---|---|---|---|---|---|
| 83 | 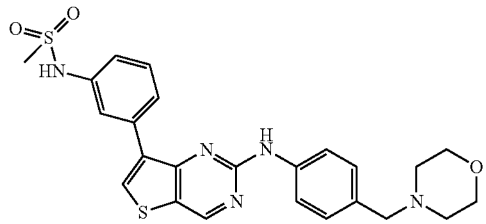 [SMILES: CS(=O)(=O)Nc1cccc(-c2csc3cnc(Nc4ccc(CN5CCOCC5)cc4)nc23)c1] | 495.14 | $C_{24}H_{25}N_5O_3S_2$ | (CDCl$_3$, 500 MHz): δ 8.94 (s, 1H), 8.03 (s, 1H), 8.00-7.99 (m, 1H), 7.79 (d, J = 7.5 Hz, 1H), 7.66 (d, J = 8.3 Hz, 2H), 7.51 (br s, 1H), 7.47 (t, J = 7.9 Hz, 1H), 7.34 (br s, 1H), 7.30 (d, J = 8.4 Hz, 2H), 7.31-7.27 (m, 1H), 3.71 (t, J = 4.5 Hz, 4H), 3.49 (s, 2H), 3.04 (s, 3H), 2.46 (t, J = 4.5 Hz, 4H) | m/z 496.0 [M + H]⁺ |
| 84 | 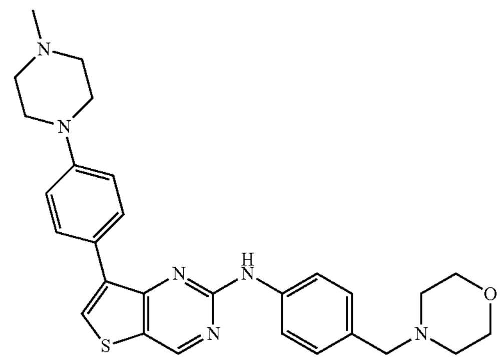 [SMILES: CN1CCN(c2ccc(-c3csc4cnc(Nc5ccc(CN6CCOCC6)cc5)nc34)cc2)CC1] | 500.24 | $C_{28}H_{32}N_6OS$ | (CDCl$_3$, 300 MHz): δ 8.92 (s, 1H), 7.94 (d, J = 8.9 Hz, 2H), 7.86 (s, 1H), 7.71 (d, J = 8.4 Hz, 2H), 7.29 (d, J = 8.5 Hz, 2H), 7.25 (br s, 1H), 7.05 (d, J = 8.9 Hz, 2H), 3.72 (t, J = 4.4 Hz, 4H), 3.49 (s, 2H), 3.32 (t, J = 5.0 Hz, 4H), 2.63 (t, J = 5.0 Hz, 4H), 2.46 (t, J = 4.5 Hz, 4H), 2.39 (s, 3H) | m/z 501.1 [M + H]⁺ |
| 85 | 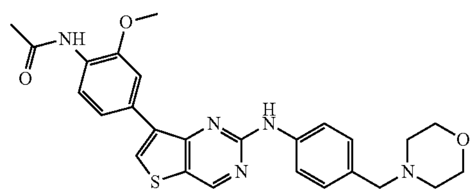 [SMILES: COc1cc(-c2csc3cnc(Nc4ccc(CN5CCOCC5)cc4)nc23)ccc1NC(C)=O] | 489.18 | $C_{26}H_{27}N_5O_3S$ | (CDCl$_3$, 500 MHz): δ 8.94 (s, 1H), 8.49 (d, J = 8.5 Hz, 1H), 7.94 (s, 1H), 7.85 (br s, 1H), 7.70 (d, J = 8.6 Hz, 2H), 7.67 (d, J = 1.8 Hz, 1H), 7.48 (dd, J = 8.4, 1.8 Hz, 1H), 7.31 (br s, 1H), 7.27 (d, J = 7.5 Hz, 2H), 3.89 (s, 3H), 3.71 (t, J = 4.6 Hz, 4H), 3.49 (s, 2H), 2.45 (t, J = 4.6 Hz, 4H), 2.26 (s, 3H) | m/z 490.1 [M + H]⁺ |
| 86 | 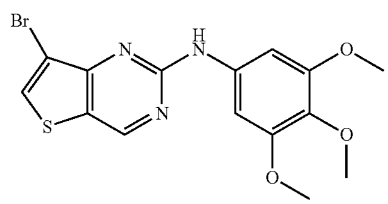 [SMILES: COc1cc(Nc2ncc3scc(Br)c3n2)cc(OC)c1OC] | 394.99 | $C_{15}H_{14}BrN_3O_3S$ | (DMSO-d$_6$, 300 MHz): δ 9.77 (s, 1H), 9.19 (s, 1H), 8.50 (s, 1H), 7.50 (s, 2H), 3.82 (s, 6H), 3.63 (s, 3H) | m/z 395.9, 397.9 [M + H]⁺ |
| 87 | 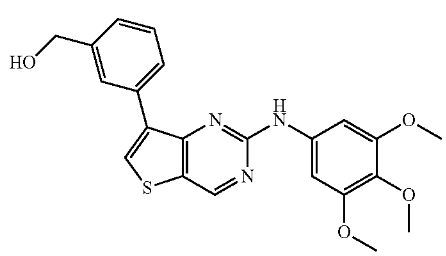 [SMILES: COc1cc(Nc2ncc3scc(-c4cccc(CO)c4)c3n2)cc(OC)c1OC] | 423.13 | $C_{22}H_{21}N_3O_4S$ | (DMSO-d$_6$, 300 MHz): δ 9.51 (s, 1H), 9.21 (s, 1H), 8.45 (s, 1H), 7.91 (d, J = 7.3, 1H), 7.82 (s, 1H), 7.39 (m, 2H), 7.19 (s, 2H), 5.23 (t, J = 5.6, 1H), 4.56 (d, J = 5.5 Hz, 2H), 3.61 (m, 9H) | m/z 424.0 [M + H]⁺ |
| 88 | 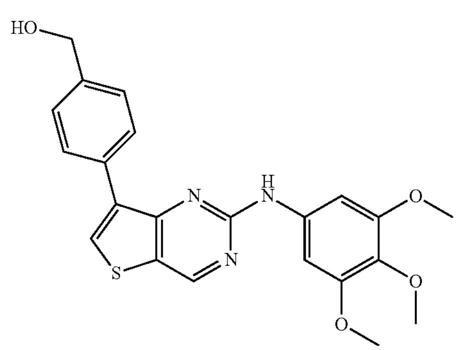 [SMILES: COc1cc(Nc2ncc3scc(-c4ccc(CO)cc4)c3n2)cc(OC)c1OC] | 423.13 | $C_{22}H_{21}N_3O_4S$ | (DMSO-d$_6$, 300 MHz): δ 9.51 (s, 1H), 9.21 (s, 1H), 8.44 (s, 1H), 7.94 (d, J = 8.2, 2H), 7.40 (d, J = 8.2, 2H), 7.21 (s, 2H), 5.27 (t, J = 5.7, 1H), 4.56 (d, J = 5.7 Hz, 2H), 3.63 (s, 6H), 3.61 (s, 3H) | m/z 424.0 [M + H]⁺ |

| No | Structure | Mol Weight | Formula | ¹H NMR data | LC-MS |
|---|---|---|---|---|---|
| 89 | 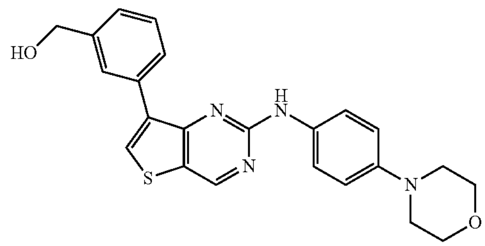 [SMILES: OCc1cccc(-c2csc3cnc(Nc4ccc(N5CCOCC5)cc4)nc23)c1] | 418.15 | $C_{23}H_{22}N_4O_2S$ | (DMSO-$d_6$, 300 MHz): δ 9.46 (s, 1H), 9.16 (s, 1H), 8.49 (s, 1H), 8.08 (s, 1H), 7.93 (d, J = 7.8, 1H), 7.74 (d, J = 8.9, 2H), 7.47 (t, J = 7.5, 1H), 7.38 (d, J = 7.5, 1H), 6.92 (d, J = 9.1, 2H), 5.27 (t, J = 5.6, 1H), 4.61 (d, J = 5.5, 2H), 3.75 (m, 4H), 3.04 (m, 4H) | m/z 419.0 [M + H]⁺ |
| 90 | 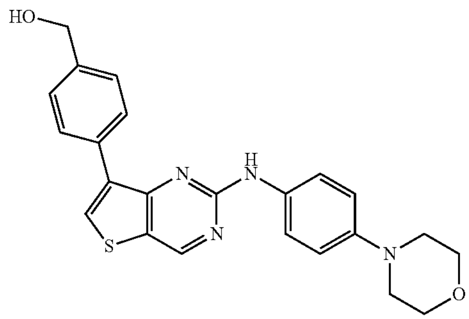 [SMILES: OCc1ccc(-c2csc3cnc(Nc4ccc(N5CCOCC5)cc4)nc23)cc1] | 418.15 | $C_{23}H_{22}N_4O_2S$ | (DMSO-$d_6$, 300 MHz): δ 9.45 (s, 1H), 9.15 (s, 1H), 8.50 (s, 1H), 8.09 (d, J = 8.2, 1H), 7.72 (d, J = 8.9, 2H), 7.45 (d, J = 8.0, 2H), 6.91 (d, J = 8.9, 2H), 5.25 (t, J = 5.7, 1H), 4.57 (d, J = 5.7, 2H), 3.75 (m, 4H), 3.05 (m, 4H). | m/z 419.0 [M + H]⁺ |
| 91 | 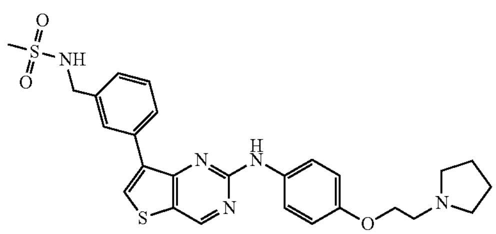 [SMILES: CS(=O)(=O)NCc1cccc(-c2csc3cnc(Nc4ccc(OCCN5CCCC5)cc4)nc23)c1] | 523.17 | $C_{26}H_{29}N_5O_3S_2$ | (CD$_3$OD, 300 MHz): δ 9.00 (s, 1H), 8.30 (s, 1H), 8.23 (s, 1H), 7.91 (d, J = 7.5, 1H), 7.75 (d, J = 8.9, 2H), 7.48 (dd, J = 7.5, 7.5, 1H), 7.43 (d, J = 7.5, 1H), 7.02 (d, J = 9.1, 2H), 4.34 (m, 4H), 3.62 (m, 2H), 3.47 (m, 4H), 2.90 (s, 3H), 2.13 (m, 4H). Missing 2H-solvent exchange | m/z 524.1 [M + H]⁺ |
| 92 | 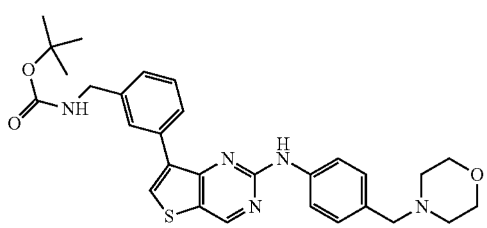 [SMILES: CC(C)(C)OC(=O)NCc1cccc(-c2csc3cnc(Nc4ccc(CN5CCOCC5)cc4)nc23)c1] | 531.23 | $C_{29}H_{33}N_5O_3S$ | (CDCl$_3$, 300 MHz): δ 8.94 (s, 1H), 7.98 (s, 1H), 7.91 (m, 1H), 7.90-7.89 (m, 1H), 7.70 (d, J = 8.5 Hz, 2H), 7.47 (t, J = 7.8 Hz, 1H), 7.36-7.34 (m, 1H), 7.28 (d, J = 8.3 Hz, 2H), 4.91 (br s, 1H), 4.42 (d, J = 5.9 Hz, 2H), 3.71 (t, J = 4.7 Hz, 4H), 3.48 (s, 2H), 2.46 (t, J = 4.6 Hz, 4H), 1.48 (s, 9H). Missing 1H-water exchange (wet solvent) | m/z 532.1 [M + H]⁺ |
| 93 | 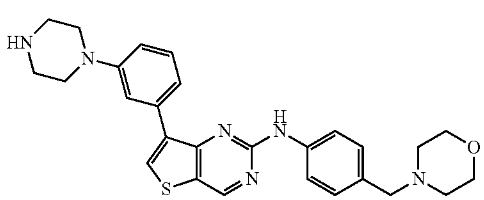 [SMILES: c1cc(-c2csc3cnc(Nc4ccc(CN5CCOCC5)cc4)nc23)cc(N2CCNCC2)c1] | 486.22 | $C_{27}H_{30}N_6OS$ | (CDCl$_3$, 300 MHz): δ 8.94 (s, 1H), 7.95 (s, 1H), 7.72 (d, J = 8.6 Hz, 2H), 7.54-7.53 (m, 1H), 7.42-7.39 (m, 2H), 7.27 (d, J = 8.6 Hz, 2H), 7.01-6.99 (m, 1H), 3.71 (t, J = 4.7 Hz, 4H), 3.47 (s, 2H), 3.22 (t, J = 4.9 Hz, 4H), 3.04 (t, J = 4.9 Hz, 4H), 2.45 (t, J = 4.6 Hz, 4H). Missing 1H-water exchange (wet solvent) | m/z 487.0 [M + H]⁺ |
| 94 | 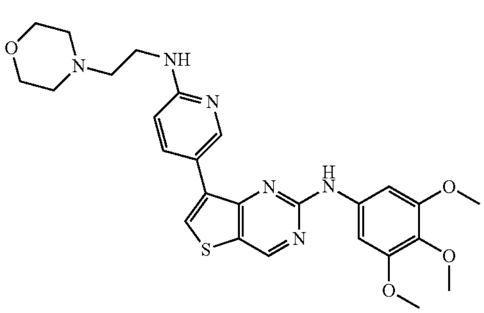 [SMILES: COc1cc(Nc2ncc3scc(-c4ccc(NCCN5CCOCC5)nc4)c3n2)cc(OC)c1OC] | 522.20 | $C_{26}H_{30}N_6O_4S$ | (DMSO-$d_6$, 300 MHz): δ 9.51 (s, 1H), 9.18 (s, 1H), 8.80 (d, J = 2.1, 1H), 8.31 (s, 1H), 7.93 (dd, J = 2.5, 8.7, 1H), 7.20 (s, 2H), 6.58 (m, 2H), 3.72 (s, 6H), 3.60 (m, 7H), 3.43 (m, 2H), 2.53 (m, 2H), 2.44 (m, 4H) | m/z 523.1 [M + H]⁺ |

-continued

| No | Structure | Mol Weight | Formula | ¹H NMR data | LC-MS |
|---|---|---|---|---|---|
| 95 | 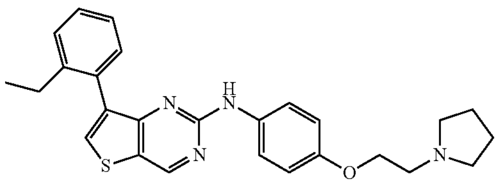 [SMILES: CCc1ccccc1-c1csc2cnc(Nc3ccc(OCCN4CCCC4)cc3)nc12] | 444.20 | $C_{26}H_{28}N_4OS$ | (CDCl$_3$, 300 MHz): δ 8.92 (s, 1H), 7.75 (s, 1H), 7.50 (d, J = 9.1, 2H), 7.35 (m, 4H), 7.05 (s, 1H), 6.83 (d, J = 8.9, 2H), 4.09 (t, J = 6.1, 2H), 2.89 (t, J = 6.1, 2H), 2.63 (m, 6H), 1.82 (m, 4H), 1.10 (t, J = 7.5, 3H) | m/z 445.1 [M + H]⁺ |
| 96 | 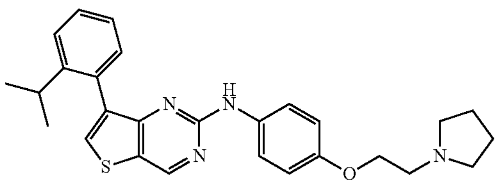 [SMILES: CC(C)c1ccccc1-c1csc2cnc(Nc3ccc(OCCN4CCCC4)cc3)nc12] | 458.21 | $C_{27}H_{30}N_4OS$ | (DMSO-d$_6$, 300 MHz): δ 9.41 (s, 1H), 9.16 (s, 1H), 8.17 (s, 1H), 7.61 (d, J = 8.9, 2H), 7.45 (m, 2H), 7.26 (m, 2H), 6.74 (d, J = 9.1, 2H), 3.98 (t, J = 5.9, 2H), 2.89 (m, 1H), 2.74 (t, J = 5.9, 2H), 2.50 (m, 4H), 1.60-1.73 (m, 4H), 1.09 (d, J = 6.9, 6H) | m/z 459.1 [M + H]⁺ |
| 97 | 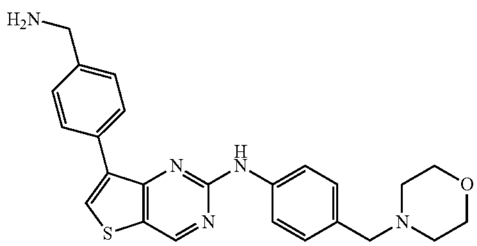 [SMILES: NCc1ccc(-c2csc3cnc(Nc4ccc(CN5CCOCC5)cc4)nc23)cc1] | 431.18 | $C_{24}H_{25}N_5OS$ | (DMSO/CDCl$_3$, 300 MHz) δ 8.99 (s, 1H), 8.68 (brs, 1H), 8.06 (s, 1H), 8.02 (d, J = 8.4 Hz, 2H), 7.95 (d, J = 8.7 Hz, 2H), 7.63 (d, J = 8.4, Hz, 2H), 7.45 (d, J = 8.7 Hz, 2H), 4.25 (s, 2H), 4.17-4.16 (m, 4H), 3.3-2.9 (m, 4H). Missing 2 H- under water peak | m/z 432.0 [M + H]⁺ |
| 98 | 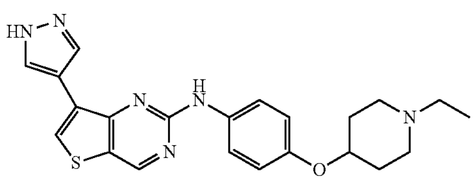 [SMILES: CCN1CCC(Oc2ccc(Nc3ncc4scc(-c5cn[nH]c5)c4n3)cc2)CC1] | 420.17 | $C_{22}H_{24}N_6OS$ | (CD3OD/CDCl$_3$, 300 MHz) δ 8.90 (s, 1H), 8.31 (br s, 2H), 8.00 (s, 1H), 7.78 (d, J = 8.7 Hz, 2H), 6.99 (d, J = 9.0 Hz, 2H), 4.72 (br s, 1H), 3.49-3.47 (m, 2H), 3.22-3.17 (m, 4H), 2.27-2.24 (m, 4H), 1.41 (t, J = 7.5 Hz, 3H). Missing 2 H- solvent exchange | m/z 421.1 [M + H]⁺ |
| 99 | 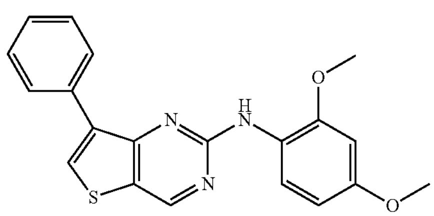 [SMILES: COc1ccc(Nc2ncc3scc(-c4ccccc4)c3n2)c(OC)c1] | 363.10 | $C_{20}H_{17}N_3O_2S$ | (CDCl$_3$, 300 MHz): δ 8.92 (s, 1H), 8.55 (d, J = 8.7, 1H), 8.03 (d, J = 7.3, 2H), 7.95 (s, 1H), 7.69 (m, 1H), 7.47 (m, 3H), 6.52 (m, 2H), 3.89 (s, 3H), 3.82 (s, 3H). | m/z 364.0 [M + H]⁺ |
| 100 | 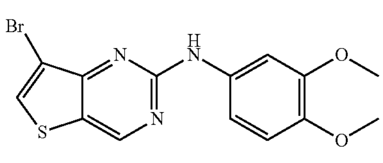 [SMILES: COc1ccc(Nc2ncc3scc(Br)c3n2)cc1OC] | 364.98 | $C_{14}H_{12}BrN_3O_2S$ | (CDCl$_3$, 300 MHz): δ 8.86 (s, 1H), 8.03 (s, 1H), 7.87 (s, 1H), 7.30 (s, 1H), 6.94 (dd, J = 2.5, 8.7, 1H), 6.86 (d, J = 8.7, 1H), 4.01 (s, 3H), 3.89 (s, 3H). | m/z 365.9, 367.9 [M + H]⁺ |
| 101 | 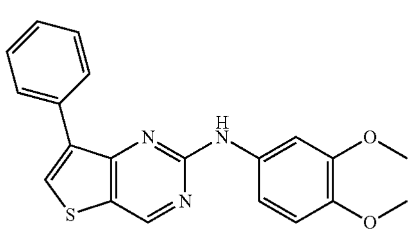 [SMILES: COc1ccc(Nc2ncc3scc(-c4ccccc4)c3n2)cc1OC] | 363.10 | $C_{20}H_{17}N_3O_2S$ | (CDCl$_3$, 300 MHz): δ 8.91 (s, 1H), 7.95 (m, 3H), 7.54 (d, J = 2.5, 1H), 7.44 (m, 4H), 7.05 (m, 1H), 6.84 (d, J = 8.7, 1H), 3.88 (s, 3H), 3.70 (s, 3H). | m/z 364.0 [M + H]⁺ |

The names of the compounds in the table are as follows:
1. 7-iodo-N-(4-morpholinophenyl)thieno[3,2-d]pyrimidin-2-amine
2. 7-(4-aminophenyl)-N-(4-morpholinophenyl)thieno[3,2-d]pyrimidin-2-amine
3. N-(4-(2-(4-morpholinophenylamino)thieno[3,2-d]pyrimidin-7-yl)phenyl)acrylamide
4. 7-(3-aminophenyl)-N-(4-morpholinophenyl)thieno[3,2-d]pyrimidin-2-amine
5. N-(3-(2-(4-morpholinophenylamino)thieno[3,2-d]pyrimidin-7-yl)phenyl)acrylamide
7. N-(4-morpholinophenyl)thieno[3,2-d]pyrimidin-2-amine
8. methyl 2-(4-morpholinophenylamino)thieno[3,2-d]pyrimidine-7-carboxylate
9. N-(4-morpholinophenyl)-5H-pyrrolo[3,2-d]pyrimidin-2-amine
10. 7-(4-amino-3-methoxyphenyl)-N-(4-morpholinophenyl)thieno[3,2-d]pyrimidin-2-amine
11. 4-(2-(4-morpholinophenylamino)thieno[3,2-d]pyrimidin-7-yl)benzenesulfonamide
12. N,N-dimethyl-3-(2-(4-morpholinophenylamino)thieno[3,2-d]pyrimidin-7-yl)benzenesulfonamide
13. 1-ethyl-3-(2-methoxy-4-(2-(4-morpholinophenylamino)thieno[3,2-d]pyrimidin-7-yl)phenyl)urea
14. N-(4-(2-(4-morpholinophenylamino)thieno[3,2-d]pyrimidin-7-yl)phenyl)methanesulfonamide
15. 2-methoxy-4-(2-(4-morpholinophenylamino)thieno[3,2-d]pyrimidin-7-yl)phenol
16. 2-cyano-N-(3-(2-(4-morpholinophenylamino)thieno[3,2-d]pyrimidin-7-yl)phenyl)acetamide
17. N-(cyanomethyl)-2-(4-morpholinophenylamino)thieno[3,2-d]pyrimidine-7-carboxamide
18. N-(3-(2-(4-morpholinophenylamino)thieno[3,2-d]pyrimidin-7-yl)phenyl)methanesulfonamide
19. 1-ethyl-3-(4-(2-(4-morpholinophenylamino)thieno[3,2-d]pyrimidin-7-yl)-2-(trifluoromethoxy)phenyl)urea
20. N-(3-nitrophenyl)-7-phenylthieno[3,2-d]pyrimidin-2-amine
21. 7-iodo-N-(3-nitrophenyl)thieno[3,2-d]pyrimidin-2-amine
22. N1-(7-(2-ethylphenyl)thieno[3,2-d]pyrimidin-2-yl)benzene-1,3-diamine
25. -tert-butyl-3-(2-(4-morpholinophenylamino)thieno[3,2-d]pyrimidin-7-yl)benzenesulfonamide
26. N1-(7-iodothieno[3,2-d]pyrimidin-2-yl)benzene-1,3-diamine
28. 7-(4-amino-3-(trifluoromethoxy)phenyl)-N-(4-morpholinophenyl)thieno[3,2-d]pyrimidin-2-amine
29. 7-(2-ethylphenyl)-N-(4-morpholinophenyl)thieno[3,2-d]pyrimidin-2-amine
30. N-(3-(2-(4-morpholinophenylamino)thieno[3,2-d]pyrimidin-7-yl)phenyl)acetamide
31. N-(cyanomethyl)-N-(3-(2-(4-morpholinophenylamino)thieno[3,2-d]pyrimidin-7-yl)phenyl)methanesulfonamide
32. N-(cyanomethyl)-N-(4-(2-(4-morpholinophenylamino)thieno[3,2-d]pyrimidin-7-yl)phenyl)methanesulfonamide
33. N-(3-(5-methyl-2-(4-morpholinophenylamino)-5H-pyrrolo[3,2-d]pyrimidin-7-yl)phenyl)methanesulfonamide
34. 4-(5-methyl-2-(4-morpholinophenylamino)-5H-pyrrolo[3,2-d]pyrimidin-7-yl)benzenesulfonamide
35. N-(4-(5-methyl-2-(4-morpholinophenylamino)-5H-pyrrolo[3,2-d]pyrimidin-7-yl)phenyl)methanesulfonamide
36. 7-iodo-N-(4-morpholinophenyl)-5H-pyrrolo[3,2-d]pyrimidin-2-amine
37. 7-(2-isopropylphenyl)-N-(4-morpholinophenyl)thieno[3,2-d]pyrimidin-2-amine
38. 7-bromo-N-(4-morpholinophenyl)thieno[3,2-d]pyrimidin-2-amine
39. N7-(2-isopropylphenyl)-N2-(4-morpholinophenyl)thieno[3,2-d]pyrimidine-2,7-diamine
40. N7-(4-isopropylphenyl)-N2-(4-morpholinophenyl)thieno[3,2-d]pyrimidine-2,7-diamine
41. 7-(5-amino-2-methylphenyl)-N-(4-morpholinophenyl)thieno[3,2-d]pyrimidin-2-amine
42. N-(cyanomethyl)-4-(2-(4-morpholinophenylamino)thieno[3,2-d]pyrimidin-7-yl)benzamide
43. 7-iodo-N-(3-morpholinophenyl)thieno[3,2-d]pyrimidin-2-amine
44. 7-(4-amino-3-nitrophenyl)-N-(4-morpholinophenyl)thieno[3,2-d]pyrimidin-2-amine
45. 7-(2-methoxypyridin-3-yl)-N-(4-morpholinophenyl)thieno[3,2-d]pyrimidin-2-amine
46. (3-(7-iodothieno[3,2-d]pyrimidin-2-ylamino)phenyl)methanol
47. N-tert-butyl-3-(2-(3-morpholinophenylamino)thieno[3,2-d]pyrimidin-7-yl)benzenesulfonamide
48. N-tert-butyl-3-(2-(3-(hydroxymethyl)phenylamino)thieno[3,2-d]pyrimidin-7-yl)benzenesulfonamide
49. N-(4-morpholinophenyl)-7-(4-nitrophenylthio)-5H-pyrrolo[3,2-d]pyrimidin-2-amine
50. N-tert-butyl-3-(2-(3,4,5-trimethoxyphenylamino)thieno[3,2-d]pyrimidin-7-yl)benzenesulfonamide
51. 7-(4-amino-3-nitrophenyl)-N-(3,4-dimethoxyphenyl)thieno[3,2-d]pyrimidin-2-amine
51. N-(3,4-dimethoxyphenyl)-7-(2-methoxypyridin-3-yl)thieno[3,2-d]pyrimidin-2-amine
52. N-tert-butyl-3-(2-(3,4-dimethoxyphenylamino)thieno[3,2-d]pyrimidin-7-yl)benzenesulfonamide
54. 7-(2-aminopyrimidin-5-yl)-N-(3,4-dimethoxyphenyl)thieno[3,2-d]pyrimidin-2-amine
55. N-(3,4-dimethoxyphenyl)-7-(2,6-dimethoxypyridin-3-yl)thieno[3,2-d]pyrimidin-2-amine
56. N-(3,4-dimethoxyphenyl)-7-(2,4-dimethoxypyrimidin-5-yl)thieno[3,2-d]pyrimidin-2-amine
57. 7-iodo-N-(4-(morpholinomethyl)phenyl)thieno[3,2-d]pyrimidin-2-amine
58. N-tert-butyl-3-(2-(4-(morpholinomethyl)phenylamino)thieno[3,2-d]pyrimidin-7-yl)benzenesulfonamide
59. 2-cyano-N-(4-methyl-3-(2-(4-morpholinophenylamino)thieno[3,2-d]pyrimidin-7-yl)phenyl)acetamide
60. ethyl 3-(2-(4-morpholinophenylamino)thieno[3,2-d]pyrimidin-7-yl)benzoate
61. 7-bromo-N-(4-(2-(pyrrolidin-1-yl)ethoxy)phenyl)thieno[3,2-d]pyrimidin-2-amine
62. N-(3-(2-(4-(2-(pyrrolidin-1-yl)ethoxy)phenylamino)thieno[3,2-d]pyrimidin-7-yl)phenyl)acetamide
63. N-(cyanomethyl)-3-(2-(4-morpholinophenylamino)thieno[3,2-d]pyrimidin-7-yl)benzamide
64. N-tert-butyl-3-(2-(4-morpholinophenylamino)thieno[3,2-d]pyrimidin-7-yl)benzamide
65. N-tert-butyl-3-(2-(4-(1-ethylpiperidin-4-yloxy)phenylamino)thieno[3,2-d]pyrimidin-7-yl)benzenesulfonamide
66. tert-butyl 4-(2-(4-(morpholinomethyl)phenylamino)thieno[3,2-d]pyrimidin-7-yl)-1H-pyrazole-1-carboxylate
67. 7-bromo-N-(4-((4-ethylpiperazin-1-yl)methyl)phenyl)thieno[3,2-d]pyrimidin-2-amine 68. N-tert-butyl-3-(2-(4-((4-ethylpiperazin-1-yl)methyl)phenylamino)thieno[3,2-d]pyrimidin-7-yl)benzenesulfonamide
69. N-(4-((4-ethylpiperazin-1-yl)methyl)phenyl)-7-(1H-pyrazol-4-yl)thieno[3,2-d]pyrimidin-2-amine
70. N-(cyanomethyl)-3-(2-(4-(morpholinomethyl)phenylamino)thieno[3,2-d]pyrimidin-7-yl)benzamide
71. N-tert-butyl-3-(2-(4-(2-(pyrrolidin-1-yl)ethoxy)phenylamino)thieno[3,2-d]pyrimidin-7-yl)benzenesulfonamide
72. tert-butyl pyrrolidin-1-yl)ethoxy)phenylamino)thieno[3,2-d]pyrimidin-7-yl)benzylcarbamate
73. 3-(2-(4-(2-(pyrrolidin-1-yl)ethoxy)phenylamino)thieno[3,2-d]pyrimidin-7-yl)benzenesulfonamide
74. 7-(3-chloro-4-fluorophenyl)-N-(4-(2-(pyrrolidin-1-yl)ethoxy)phenyl)thieno[3,2-d]pyrimidin-2-amine
75. tert-butyl 4-(2-(4-(1-ethylpiperidin-4-yloxy)phenylamino)thieno[3,2-d]pyrimidin-7-yl)-1H-pyrazole-1-carboxylate
76. 7-(benzo[d][1,3]dioxol-5-yl)-N-(4-(morpholinomethyl)phenyl)thieno[3,2-d]pyrimidin-2-amine
77. tert-butyl 5-(2-(4-(morpholinomethyl)phenylamino)thieno[3,2-d]pyrimidin-7-yl)-1H-indole-1-carboxylate
78. 7-(2-aminopyrimidin-5-yl)-N-(4-(morpholinomethyl)phenyl)thieno[3,2-d]pyrimidin-2-amine
79. tert-butyl 4-(2-(4-(morpholinomethyl)phenylamino)thieno[3,2-d]pyrimidin-7-yl)-5,6-dihydropyridine-1(2H)-carboxylate
80. tert-butyl 4-(2-(4-(morpholinomethyl)phenylamino)thieno[3,2-d]pyrimidin-7-yl)benzylcarbamate
81. N-(3-(2-(4-(morpholinomethyl)phenylamino)thieno[3,2-d]pyrimidin-7-yl)phenyl)acetamide
82. N-(4-(2-(4-(morpholinomethyl)phenylamino)thieno[3,2-d]pyrimidin-7-yl)phenyl)acetamide
83. N-(3-(2-(4-(morpholinomethyl)phenylamino)thieno[3,2-d]pyrimidin-7-yl)phenyl)methanesulfonamide
84. 7-(4-(4-methylpiperazin-1-yl)phenyl)-N-(4-(morpholinomethyl)phenyl)thieno[3,2-d]pyrimidin-2-amine
85. N-(2-methoxy-4-(2-(4-(morpholinomethyl)phenylamino)thieno[3,2-d]pyrimidin-7-yl)phenyl)acetamide
86. 7-bromo-N-(3,4,5-trimethoxyphenyl)thieno[3,2-d]pyrimidin-2-amine
87. (3-(2-(3,4,5-trimethoxyphenylamino)thieno[3,2-d]pyrimidin-7-yl)phenyl)methanol
88. (4-(2-(3,4,5-trimethoxyphenylamino)thieno[3,2-d]pyrimidin-7-yl)phenyl)methanol
89. (3-(2-(4-morpholinophenylamino)thieno[3,2-d]pyrimidin-7-yl)phenyl)methanol
90. (4-(2-(4-morpholinophenylamino)thieno[3,2-d]pyrimidin-7-yl)phenyl)methanol
91. N-(pyrrolidin-1-yl)ethoxy)phenylamino)thieno[3,2-d]pyrimidin-7-yl)benzyl)methanesulfonamide
92. tert-butyl 3-(2-(4-(morpholinomethyl)phenylamino)thieno[3,2-d]pyrimidin-7-yl)benzylcarbamate
93. N-(4-(morpholinomethyl)phenyl)-7-(3-(piperazin-1-yl)phenyl)thieno[3,2-d]pyrimidin-2-amine
94. 7-(6-(2-morpholinoethylamino)pyridin-3-yl)-N-(3,4,5-trimethoxyphenyl)thieno[3,2-d]pyrimidin-2-amine
95. 7-(2-ethylphenyl)-N-(4-(pyrrolidin-1-yl)ethoxy)phenyl)thieno[3,2-d]pyrimidin-2-amine
96. 7-(2-isopropylphenyl)-N-(4-(pyrrolidin-1-yl)ethoxy)phenyl(thieno [3,2-d]pyrimidin-2-amine
97. 7-(4-(aminomethyl)phenyl)-N-(4-(morpholinomethyl)phenyl)thieno[3,2-d]pyrimidin-2-amine
98. N-(4-(1-ethylpiperidin-4-yloxy)phenyl)-7-(1H-pyrazol-4-yl)thieno[3,2-d]pyrimidin-2-amine
99. N-(2,4-dimethoxyphenyl)-7-phenylthieno[3,2-d]pyrimidin-2-amine
100. 7-bromo-N-(3,4-dimethoxyphenyl)thieno[3,2-d]pyrimidin-2-amine
101. N-(3,4-dimethoxyphenyl)-7-phenylthieno[3,2-d]pyrimidin-2-amine The term "$C_{1-6}$alkyl" refers to straight chain or branched chain hydrocarbon groups having from 1 to 6 carbon atoms. Examples include ethyl, propyl, isopropyl, butyl, isobutyl, sec-butyl, tert-butyl, pentyl, neopentyl and hexyl.

The term "$C_{1-6}$alkylene" refers to the divalent equivalent of "$C_{1-6}$alkyl" defined above.

The term "$C_{2-6}$alkenyl" refers to straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl.

The term "$C_{2-6}$alkynyl" refers to straight chain or branched chain hydrocarbon groups having at least one triple bond and 2 to 4 carbon atoms. Examples include ethynyl, 1- or 2-propynyl, 1-, 2- or 3-butynyl and methyl-2-propynyl.

The term "$C_{3-6}$cycloalkyl" refers to non-aromatic cyclic hydrocarbon groups having from 3 to 6 carbon atoms. Examples include cyclopropyl, cyclobutyl, cyclopentyl and cyclohexyl.

The term "aryl" refers to single, polynuclear, conjugated or fused residues of aromatic hydrocarbons. Examples include phenyl, biphenyl, terphenyl, quaterphenyl, naphthyl, tetrahydronaphthyl, anthracenyl, dihydroanthracenyl, benzanthracenyl, dibenxanthracenyl and phenanthrenyl. 5- or 6-membered aryls such as phenyl are preferred.

The term "heterocyclyl" refers to saturated or unsaturated, monocyclic or polycyclic hydrocarbon groups containing at least one heteroatom atom selected from the group consisting of N, O, S and $SO_2$.

Suitable heterocyclyls include N-containing heterocyclic groups, such as, unsaturated 3 to 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, pyrrolinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulfur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulfur atoms and 1 to 3 nitrogen atoms, such as, thiazolyl or thiadiazolyl;

saturated 3 to 6-membered heteromonocyclic group containing 1 to 2 sulfur atoms and 1 to 3 nitrogen atoms, such as, thiomopholino or thiazolidinyl; and saturated 3 to 6-membered heteromonocyclic group containing 1 to 2 sulfur atoms, 1 to 3 nitrogen atoms and 1 to 2 oxygen atoms such as thiomorpholino-1-oxide and thiomorpholino-1,1-dioxide;

unsaturated condensed heterocyclic group containing 1 to 2 sulfur atoms and 1 to 3 nitrogen atoms, such as, benzothiazolyl or benzothiadiazolyl.

Preferred heterocyclyls are morpholino, thiomorpholino, thiomorpholino-1-oxide, thiomorpholino-1,1-dioxide, $NR^2$-piperazine, 4-hydroxy piperidine, 3-hydroxy pyrrolidine, 3-hydroxypyrrole or piperidine.

The term "halogen" refers to fluorine, chlorine, bromine and iodine, preferably fluorine.

The term "substituted or substituted" refers to a group that may or may not be further substituted with one or more groups selected from $C_{1-6}$ alkyl, $Si(C_{1-6}alkyl)_3$, $C_{3-6}$ cycloalkyl, $C_{2-6}$ alkenyl, $C_{2-6}$ alkynyl, aryl, heterocyclyl, halo, halo$C_{1-6}$alkyl, halo$C_{3-6}$cycloalkyl, halo$C_{2-6}$alkenyl, halo$C_{2-6}$alkynyl, haloaryl, haloheterocyclyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocycylylacyl, acylamino, acyloxy, aldehydo, $C_{1-6}$alkylsulfonyl, arylsulfonyl, $C_{1-6}$alkylsulfonylamino, arylsulphonylamino, $C_{1-6}$alkylsulfonyloxy, arylsulfonyloxy, $C_{1-6}$alkylsulfenyl, $C_{2-6}$alklysulfenyl, arylsulfenyl, carboalkoxy, carboaryloxy, mercapto, $C_{1-6}$alkylthio, arylthio, acylthio, cyano and the like. Preferred optional substituents are selected from the group consisting of $C_{1-4}$ alkyl, $Si(C_{1-6}alkyl)_3$, $C_{3-6}$ cycloalkyl, $C_{2-6}$ alkenyl, $C_{2-6}$ alkynyl, aryl, heterocyclyl, halo, hydroxy, $C_{1-4}$ alkoxy, aryloxy, carboxy, amino, arylacyl, heterocycylylacyl, acylamino, acyloxy, arylsulfonyl and cyano.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Where a compound possesses a chiral center the compound can be used as a purified enantiomer or diastereomer, or as a mixture of any ratio of stereoisomers. It is however preferred that the mixture comprises at least 70%, 80%, 90%, 95%, 97.5% or 99% of the preferred isomer.

This invention also encompasses prodrugs of the compounds of formula I. For example, compounds of formula I having free amino, amido, hydroxy or carboxylic acid groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of appropriate nitrogen and sulfur atoms in formula I.

This invention also encompasses methods of treating or preventing disorders that can be treated or prevented by the inhibition of protein kinases, such as JAK or aurora kinases comprising administering drugs or prodrugs of compounds of the invention.

Process of Making Compounds

Compounds of the general formula I are generally prepared from a dihalogenated heterocycle. The process may be performed in either the order described below or the reverse of such.

The first step of the process typically involves a nucleophilic aromatic substitution reaction of the dihalogenated heterocycle with a suitable amine. The nucleophilic aromatic substitution is typically carried out by addition of the amine to the dihalogenated heterocycle in a solvent such as ethanol, n-propanol, isopropanol, tert-butanol, dioxane, THF, DMF, toluene, NMP or xylene. The reaction is typically performed under conventional or microwave heating in the presence of an acid such as HCl or p-toluenesulfonic acid or in the presence of base such as a non-nucleophilic base such as triethylamine or diisopropylethylamine, or an inorganic base such as potassium carbonate or sodium carbonate. Alternately the reaction can be carried out without solvent.

Alternatively, the amine substituent may be introduced through a transition metal catalysed amination reaction. Typical catalysts/ligands for such transformations include $Pd(OAc)_2/P(t-Bu)_3$, $Pd_2(dba)_3/BINAP$ and $Pd(OAc)_2/BINAP$. These reactions are typically carried out in solvents such as toluene or dioxane, in the presence of bases such as caesium carbonate or sodium or potassium tert-butoxide at temperatures ranging from room temperature to reflux (e.g. Hartwig, J. F., *Angew. Chem. Int. Ed.* 1998, 37, 2046).

The amines employed in the first step of the synthesis of these compounds are obtained commercially or are prepared using methods well known to those skilled in the art.

The second step of the process typically begins with a cross-coupling reaction between the monohalogenated derivative obtained above and a suitably functionalised coupling partner. Typical coupling partners are organoboronic acids or esters (Suzuki coupling: see for example Miyaura, N. and Suzuki, *Chem Rev.* 1995, 95 2457), organostannanes (Stille coupling: see for example Stille, J. K., *Angew. Chem., Int. Ed. Engl.*, 1986, 25, 508), Grignard reagents (Kumada coupling: Kumada, M.; Tamao, K.; Sumitani, K. *Org. Synth.* 1988, Coll. Vol. 6, 407.) or organozinc species (Negishi coupling: Negishi, E.; *J. Organomet. Chem.* 2002, 653, 34). The Suzuki coupling is the preferred coupling method and is typically performed in a solvent such as DME, THF, DMF, ethanol, propanol, toluene, acetonitrile or 1,4-dioxane, with or without added water, in the presence of a base such as sodium or potassium carbonate, lithium hydroxide, caesium carbonate, sodium hydroxide, potassium fluoride or potassium phosphate. The reaction may be carried out at elevated temperatures and the palladium catalyst employed may be selected from $Pd(PPh_3)_4$, $Pd(OAc)_2$, $[PdCl_2(dppf)]$, $Pd_2(dba)_3/P(t-Bu)_3$.

The products formed from either reaction step may be further derivatised using techniques known to those skilled in the art. Alternatively, derivatisation of the mono-halo intermediate may be undertaken prior to reaction of the second halo substituent. Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionality are well-known to those skilled in the art and are described for example in Greene (Greene, T., Wuts, P. (1999) *Protective Groups in Organic Synthesis*. Wiley-Interscience; 3rd edition.).

The leaving group may be any suitable known type such as those disclosed in J. March, "Advanced Organic Chemistry: Reactions, Mechanisms and Structure" $4^{th}$ Edition, pp 352-357, John Wiley & Sons, New York, 1992 which is incorporated herein by reference. Preferably, the leaving group is halogen, more preferably chlorine.

JAK Inhibition

The compounds of formula I have activity against protein kinases, particularly the JAK kinases or aurora kinases and most particularly selective activity against JAK1, JAK2, JAK3 or TYK2 kinases or combinations thereof. A JAK2 inhibitor is any compound that selectively inhibits the activity of JAK2. A JAK3 inhibitor is any compound that selectively inhibits the activity of JAK3. A JAK1/JAK2 selective inhibitor is any compound that selectively inhibits both JAK1 and JAK2. One activity of both JAK2 and JAK3 is to phosphorylate a STAT protein. Therefore an example of an effect of a JAK2 or JAK3 inhibitor is to decrease the phosphorylation of one or more STAT proteins. The inhibitor may inhibit the phosphorylated form of JAK2 or JAK3 or the non-phosphorylated form of JAK2 or JAK3.

Selective and Irreversible Inhibition of JAK3

A PTK catalyses the transfer of a phosphate group from a molecule of ATP to a tyrosine residue located on a protein substrate. The inhibitors known in the art are usually competitive with either the ATP or the protein substrate of the kinase (Levitzki 2000). Since the concentration of ATP in a cell is normally very high (millimolar), compounds that are competitive with ATP may lack in vivo activity since it is unlikely that said compounds can reach the concentrations within the cell that are necessary to displace the ATP from its binding site.

An alternative approach which has been attempted in relation to EGFR is to design or select compounds which bind to EGFR TK in an irreversible manner. Such compounds are disclosed in Fry 1998; Discafani 1999; Smaill 1999; Smaill 2000; Tsou 2001; Smaill 2001; Wissner 2003. These compounds function as irreversible inhibitors by virtue of the fact that they can form covalent bonds to amino acid residues located at the active site of the enzyme which results in enhanced potency of the compounds in vitro and in the inhibition of growth of human tumors in in vivo models of cancer. A further benefit of such irreversible inhibitors when compared to reversible inhibitors, is that irreversible inhibitors can be used in prolonged suppression of the tyrosine kinase, limited only by the normal rate of receptor turnover.

Alignment of the four members of the JAK family of protein tyrosine kinases reveals that within the amino acids that comprise the ATP-binding pocket of these kinases there are very few amino acid differences that could be used to target potential inhibitors towards one family member or another. Interestingly, JAK3 alone amongst this sub-family of kinases possesses a Cysteine residue close to the front lip of the ATP-binding cavity (Cys 963). By targeting thistysteine with a functionality bearing an alkylating group such as a Michael acceptor, or other such group that can react reversibly or irreversibly with the thiol moiety of this Cysteine residue, highly selective JAK3 inhibition can be achieved.

Pharmaceutical Compositions

The present invention provides pharmaceutical compositions comprising at least one of the compounds of the formula I and a pharmaceutically acceptable carrier. The carrier must be "pharmaceutically acceptable" means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins).

The compounds of the invention may be administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly in the form of a solution or suspension; vaginally in the form of pessaries, tampons or creams; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The pharmaceutical compositions for the administration of the compounds of the invention may conveniently be presented in dosage unit form and may be prepared by any of the methods well known in the art of pharmacy. These methods generally include the step of bringing the compound of formula I into association with the carrier which constitutes one or more accessory ingredients. In general, the pharmaceutical compositions are prepared by uniformly and intimately bringing the compound of formula I into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the compound of formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavouring agents, colouring agents and preserving agents, e.g. to provide pharmaceutically stable and palatable preparations. Tablets contain the compound of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the compound of formula I is mixed with an inert solid diluent, for example, calcium carbonate, calcium phosphate or kaolin, or as soft gelatin capsules wherein the compound of formula I is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula I in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, including intranasal administration, the active compound may be administered by any of the methods and formulations employed in the art for administration to the respiratory tract.

Thus in general the active compound may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the subject administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of active compound may be controlled by provision of a metered valve.

Alternatively the active compound may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the active compound will generally have a small particle size, for example of the order of 5 microns or less. Such a particle size may be obtained by means known in the art, for example by micronisation.

When desired, formulations adapted to give sustained release of the active compound may be employed.

The active compound may be administered by oral inhalation as a free-flow powder via a "Diskhaler" (trade mark of Glaxo Group Ltd) or a meter dose aerosol inhaler.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions suitable for vaginal administration may be presented as pessaries, tampons, creams, gels, pastes, foams or sprays containing in addition to the active ingredient such carriers as are known in the art to be appropriate.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorhexidine and thickening agents such as hypromellose may also be included.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

Efficacy of this class of compounds may be applicable to drug eluting stents.

Potential applications of drug eluting stents with these compounds include pulmonary artery stenosis, pulmonary vein stenosis, as well as coronary artery stenosis. Drug eluting stents may also be used in saphenous vein grafts or arterial grafts or conduits. Drug eluting stents that release this class of compounds may also be applicable for treating stenoses of the aorta or peripheral arteries, such as the iliac artery, the femoral artery or the popliteal artery. The compound may be bound to the drug eluting stent by any of various methods known in the field. Examples of such methods include polymers, phosphoryl choline, and ceramics. The compound may also be impregnated into a bioabsorbable stent.

The active compounds may also be presented for use in the form of veterinary compositions, which may be prepared, for example, by methods that are conventional in the art. Examples of such veterinary compositions include those adapted for:

oral administration, external application, for example drenches (e.g. aqueous or non-aqueous solutions or suspensions); tablets or boluses; powders, granules or pellets for admixture with feed stuffs; pastes for application to the tongue;

parenteral administration for example by subcutaneous, intramuscular or intravenous injection, e.g. as a sterile solution or suspension; or (when appropriate) by intramammary injection where a suspension or solution is introduced in the udder via the teat;

topical applications, e.g. as a cream, ointment or spray applied to the skin; or rectally or intravaginally, e.g. as a pessary, cream or foam.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: endothelin receptor antagonists (eg ambrisentan, bosentan, sitaxsentan), PDE-V inhibitors (eg sildenafil, tadalafil, vardenafil), Calcium channel blockers (eg amlodipine, felodipine, varepamil, diltiazem, menthol), prostacyclin, treprostinil, iloprost, beraprost, nitric oxide, oxygen, heparin, warfarin, diuretics, digoxin, cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABA's such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

Methods of Treatment

The compounds of formula I may be used in the treatment of kinase associated diseases including JAK kinase associated diseases such immunological and inflammatory diseases including organ transplants; hyperproliferative diseases including cancer and myeloproliferative diseases; viral diseases; metabolic diseases; and vascular diseases.

Generally, the term "treatment" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The term "subject" refers to any animal having a disease which requires treatment with the compound of formula I.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

The term "kinase associated diseases" refers to a disorder or disorders that directly or indirectly result from or are aggravated by aberrant kinase activity, in particular JAK or aurora kinase activity and/or which are alleviated by inhibition of one or more of these kinase enzymes.

In a preferred embodiment the kinase associated disease state involves one or more of the JAK kinases, JAK1, JAK2, JAK3 or TYK2. In a particularly preferred embodiment, the disease involves JAK2 or JAK3 kinase. Such diseases include, but are not limited to, those listed in the Table below.

Activation of the JAK/STAT Pathway in Various Pathologies

| Disease Type | Cell Types Involved | Cytokines involved | JAK Kinase Involved | Characteristics |
|---|---|---|---|---|
| Atopy Allergic Asthma, Atopic Dermatitis (Eczema), Allergic Rhinitis, | Mast Cells, Eosinophils, T-Cells, B-Cells, | IL-4, IL-5, IL-6, IL-7, IL-13 | JAK1, JAK2, JAK3, Tyk2 | T-cell activation of B-cells followed by IgE mediated activation of resident Mast cells and Eosinophils |
| CMI Allergic Contact Dermatitis, hypersensitivity pneumonitis | T-cells, B-cells, macrophages, neutrophils | IL-2, IL-4, IL-5, IL-6, IL-10, IFN$_\gamma$, TNF, IL-7, IL-13, | JAK1, JAK2, JAK3, Tyk2 | B cell and/or T$_{DH}$ cell activation Macrophage/granulocyte activation |
| AutoImmune Diseases Multiple sclerosis, Glomerulonephritis Systemic Lupus Erythematosus (SLE), Rheumatoid Arthritis, Juvenile Arthritis, Sjögren's Syndrome, Scleroderma Polymyositis, Ankylosing Spondylitis, Psoriatic Arthritis | B-Cells, T cells, monocytes, Macrophages, Neutrophils, Mast Cells, Eosinophils, | IL-2, IL-4, IL-5, IL-6, IL-7, Il-10, IL-13, IFN$_\gamma$, TNF, GM-CSF; G-CSF, | JAK1, JAK2, JAK3, Tyk2 | Cytokine Production (e.g. TNFα/β, IL-1, CSF-1, GM-CSF), T-cell Activation, B cell activation, JAK/STAT activation |
| Atopy Allergic Asthma, Atopic Dermatitis (Eczema), Allergic Rhinitis, | Mast Cells, Eosinophils, T-Cells, B-Cells, | IL-4, IL-5, IL-6, IL-7, IL-13 | JAK1, JAK2, JAK3, Tyk2 | T-cell activation of B-cells followed by IgE mediated activation of resident Mast cells and Eosinophils |

| Disease Type | Cell Types Involved | Cytokines involved | JAK Kinase Involved | Characteristics |
| --- | --- | --- | --- | --- |
| Transplantation Allograft Rejection GvHD | T cells, B cells, macrophages | IL-2, IL-4, IL-5, IL-7, IL-13, TNF | JAK1, JAK2, JAK3 | Macrophage/T cell mediated necrosis, Tc cell mediated apoptosis, and B cell/Ig mediated opsonization/necrosis of foreign graft |
| Viral Diseases Epstein Barr Virus (EBV) | Lymphocytes | Viral Cytokines, IL-2, | JAK1, JAK2, JAK3 | JAK/STAT Mediation |
| Hepatitis B | Hepatocytes | | | |
| Hepatitis C | Hepatocytes | | | |
| HIV | Lymphocytes | | | |
| HTLV 1 | Lymphocytes | | | |
| Varicella-Zoster Virus (VZV) | Fibroblasts | | | |
| Human Papilloma Virus (HPV) | Epithelial cells | | | |
| Hyperproliferative diseases-cancer | | Various Autocrine cytokines, Intrinsic Activation | JAK1, JAK2, JAK3 | Cytokine production, JAK/STAT Activation |
| Leukemia | Leucocytes | | | |
| Lymphoma | Lymphocytes | | | |
| Multiple Myeloma | various | | | |
| prostate cancer | various | | | |
| breast cancer | various | | | |
| hodgkins lympohoma | various | | | |
| B-cell chronic lymphocytic leukemia | various | | | |
| lung cancer | various | | | |
| hepatoma | various | | | |
| metastatic myeloma | various | | | |
| Glioma | various | | | |
| Myeloproliferative Diseases Polycythemia vera, primary myelofibrosis, thrombocythemia, essential thrombocythemia, idiopathic myelofibrosis, chronic myelogenous leukemia | Hematopoietic | Interleukin-3 erythropoietin, thrombopoietin | JAK2 mutation | JAK/STAT activation |
| Vascular Disease Hypertension, Hypertrophy, Heart Failure, Ischemia, Pulmonary arterial hypertension | Endothelial cells, smooth muscle cells including pulmonary artery smooth muscle cells, cardiac myocytes, fibroblasts, endothelial cells | IL6, angiotensin II, LIF, TNFalpha, serotonin, caveolin1 | JAK1, JAK2, TYK2 | JAK/STAT activation |
| Metabolic disease Obesity, metabolic syndrome | Adipocytes, pituitary cells, neurons, monocytes | Leptin | JAK2 | JAK/STAT activation |

The term "immunological and inflammatory disease" refers to an immunological, inflammatory or autoimmune disease, including but not limited to rheumatoid arthritis, polyarthritis, rheumatoid spondylitis, osteoarthritis, gout, asthma, bronchitis, allergic rhinitis, chronic obstructive pulmonary disease, cystic fibrosis, inflammatory bowel disease, irritable bowel syndrome, mucous colitis, ulcerative colitis, diabrotic colitis, Crohn's disease, autoimmune thyroid disorders, gastritis, esophagitis, hepatitis, pancreatitis, nephritis, psoriasis, eczema, acne vulgaris, dermatitis, hives, multiple sclerosis, Alzheimer's disease, Lou Gehrig's disease, Paget's disease, sepsis, conjunctivitis, neranl catarrh, chronic arthrorheumatism, systemic inflammatory response syndrome (SIRS), polymyositis, dermatomyositis (DM), Polaritis nodoa (PN), mixed connective tissue disorder (MCTD), Sjoegren's syndrome, Crouzon syndrome, achondroplasia, systemic lupus erythematosus, scleroderma, vasculitis, thanatophoric dysplasia, insulin resistance, Type I diabetes and complications from diabetes and metabolic syndrome.

The term "hyperproliferative diseases" includes cancer and myeloproliferative disease states such as cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfrorna (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal glands: neuroblastoma; and Myleoproliferative diseases such as polycythemia vera, primary myelofibrosis, thrombocythemia, essential thrombocythemia (ET), agnoneic myeloid metaplasia (AMM), also referred to as idiopathic myelofibrosis (IMF), and chronic myelogenous leukemia (CML).

The term "vascular diseases" refers to diseases including but not limited to cardiovascular diseases, hypertension, hypertrophy, hypercholesterolemia, hyperlipidemia, thrombotic disorders, stroke, Raynaud's phenomenon, POEMS syndrome, angina, ischemia, migraine, peripheral arterial disease, heart failure, restenosis, atherosclerosis, left ventricular hypertrophy, myocardial infarction, ischemic diseases of heart, kidney, liver and brain, and pulmonary arterial hypertension.

Preferred diseases for JAK2 selective inhibitors include immunological and inflammatory diseases such as auto-immune diseases for example atopic dermatitis, asthma, rheumatoid arthritis, Crohn's disease, psoriasis, Crouzon syndrome, achondroplasia, systemic lupus erythematosus, scleroderma, mixed connective tissue disease, vasculitis, thanatophoric dysplasia and diabetes; hyperproliferative disorders such as cancer for example prostate cancer, colon cancer, breast cancer, gastric cancer, liver cancer such as hepatoma, lung cancer, head and neck cancer such as glioma, skin cancer such as metastatic melanoma, leukemia, lymphoma, multiple myeloma and myeoproliferative diseases such as polycythemia vera, myelofibrosis, thrombocythemia, essential thrombocythemia (ET), agnoneic myeloid metaplasia (AMM), also referred to as idiopathic myelofibrosis (IMF), and chronic myelogenous leukemia (CML); and vascular diseases such as hypertension, hypertrophy, stroke, Raynaud's phenomenon, POEMS syndrome, angina, ischemia, migraine, peripheral arterial disease, heart failure, restenosis, atherosclerosis and pulmonary arterial hypertension.

Preferred diseases for compounds which selectively inhibit both JAK1 and JAK2 are hyperproliferative diseases such as cancer for example prostate cancer, colon cancer, breast cancer, gastric cancer, liver cancer such as hepatoma, lung cancer, head and neck cancer such as glioma, skin cancer such as metastatic melanoma, leukemia, lymphoma and multiple myeloma.

Preferred diseases for selective inhibitors of JAK3 are immunological and inflammatory diseases such as systemic lupus erythematosus, mixed connective tissue disease, scleroderma, multiple sclerosis, autoimmune neuritis, rheumatoid arthritis, psoriasis, insulin resistance, Type I diabetes and complications from diabetes, metabolic syndrome, asthma, atopic dermatitis, autoimmune thyroid disorders, ulcerative colitis, Crohn's disease, Alzheimer's disease, and other indications where immunosuppression may be desirable such as organ transplants. Furthermore specific inhibitors of JAK3 may find application for therapeutic treatments for hyperproliferative diseases such as leukaemia and lymphoma where JAK3 is hyperactivated.

Dosages

The term "therapeutically effective amount" refers to the amount of the compound of formula I that will elicit the biological or medical response of a tissue, system, animal or human that is being sought by the researcher, veterinarian, medical doctor or other clinician.

In the treatment or prevention of conditions which require kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The dosage may be selected, for example to any dose within any of these ranges, for therapeutic efficacy and/or symptomatic adjustment of the dosage to the patient to be treated. The compounds will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order to exemplify the nature of the present invention such that it may be more clearly understood, the following non-limiting examples are provided.

EXAMPLES

Compound Synthesis

The compounds of the invention may be prepared by methods well known to those skilled in the art, and as described in the synthetic and experimental procedures shown below for selected compounds.

Definitions:
PyBOP benzotriazole-1-yloxytripyrrolidinophosphonium hexafluorophosphate
DMF N,N-dimethylformamide
DMAP 4-Dimethylaminopyridine
DCM dichloromethane
NMP 1-methyl-2-pyrrolidinone
n-PrOH n-propanol
ACN acetonitrile
EDC.HCl 1-ethyl-3-(dimethylaminopropyl)carbodiimide hydrochloride
HOBT N-hydroxybenzotriazole
TEA triethylamine
DIPEA diisopropylethylamine
p-TsOH p-toluene sulfonic acid
HATU O-(7-azabenzotriazol-1-yl)-N,N,N',N'-tetramethyluronium hexafluorophosphate
$Na_2SO_4$ sodium sulfate
THF tetrahydrofuran
t-BuOK Potassium tert butoxide
Pd(dppf)$Cl_2$ 1,1'-Bis(diphenylphosphino)ferrocene]dichloropalladium(II)
EtOAc Ethyl acetate Generalised Reaction Schemes

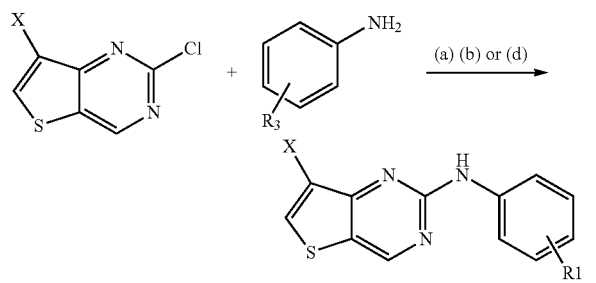

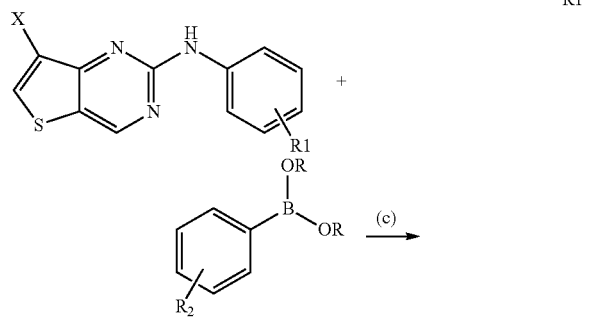

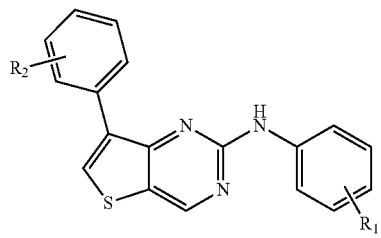

X = I, Br
R = H, $(CH_3)_2CC(CH_3)_2$
(a) p-TsOH•$H_2O$, 1,4-dioxane, microwave at 170° C. for 50 minutes;
(b) DIPEA (2.5 eq), NMP, microwave at 240° C. for 25 min;
(c) Pd[$PPh_3$]$_4$ (0.05 eq), toluene, n-PrOH, 2M $Na_2CO_3$ (aq), 90° C.,
(d) t-BuOK, THF, reflux 65 hr.

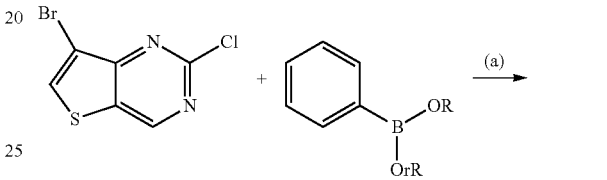

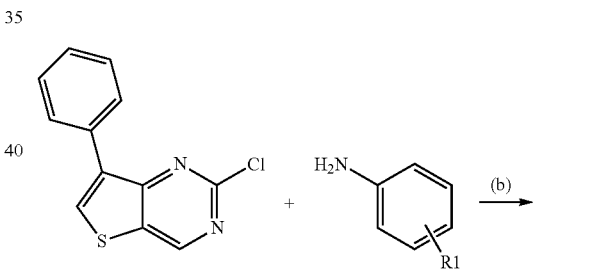

(a) Pd[$PPh_3$]$_4$ $Na_2CO_3$, toluene/isopropanol, reflux. (b) t-BuOK, THF reflux.

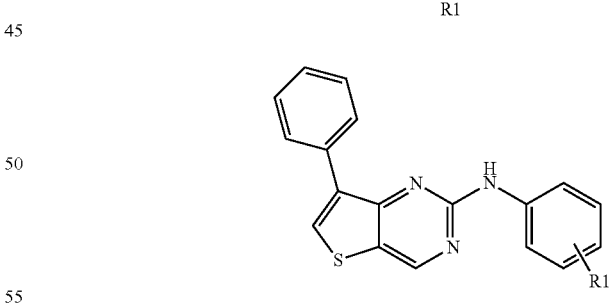

-continued

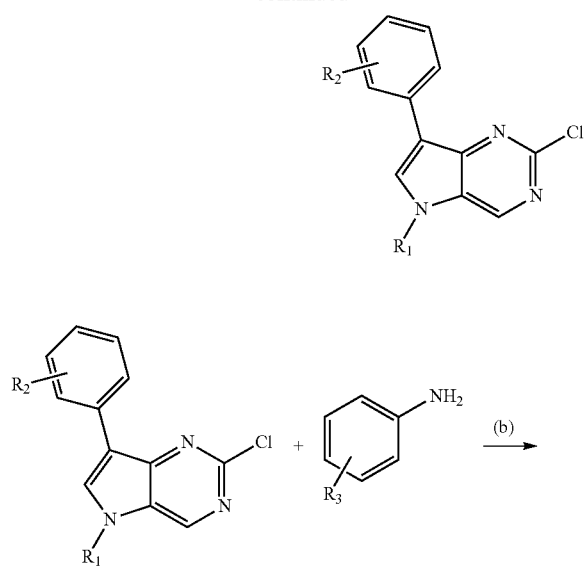

R = H, (CH₃)₂CC(CH₃)₂
(a) Pd(PPh₃)₄ (0.1 eq), DMF, 100° C., 2M Na₂CO₃ (aq) N₂ atm;
(b) NMP, DIPEA (2.5 eq), microwave at 240° C. for 5 h.

Formation of Thienopyrimidine Core

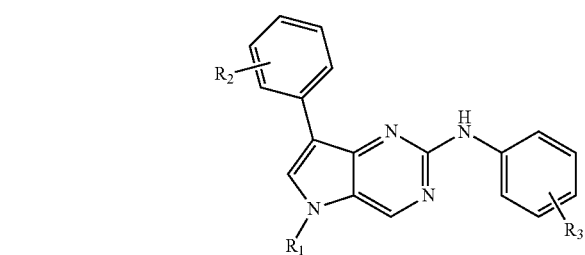

Methyl-3-amino-2-thiophenecarboxylate (20 g, 127 mmol) and urea (44 g, 732 mmol) were heated for 2 h at 200° C. The solids obtained were dissolved in 5% aq. NaOH (500 mL) and the yellow solution filtered. The basic solution was acidified to pH 5.5 by dropwise addition of 2M HCl and the precipitate collected by filtration to afford the product as a cream/white solid (19.7 g, 92%). $^1$H NMR (DMSO-d₆, 300 MHz):11.28 (br. s, 2H), 8.03 (d, J=5.1 Hz, 1H), 6.90 (d, J=5.1 Hz, 1H); LRMS (ESI): m/z calcd for [M−H]⁻ 166.99 found 167.1.

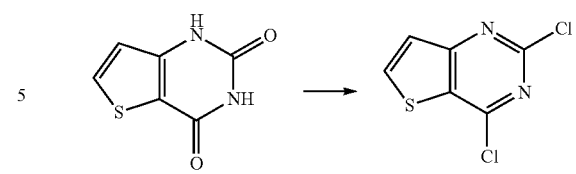

To a suspension of the uracil (5 g, 29 mmol) in POCl₃ (40 mL) was added diisopropylethylamine (13 mL, 74 mmol) and the reaction heated at reflux for 2 h. The excess POCl₃ and diisopropylethylamine were then removed by distillation under reduced pressure and the brown solid obtained dissolved in chloroform and partitioned against water. The aqueous phase was made basic by the addition of 5M NaOH, and extracted twice further with chloroform. The combined organic fractions were washed with water and brine, dried (Na₂SO₄) filtered and concentrated to afford the product as a pale brown solid (6.05 g, quantitative yield). $^1$H NMR (CDCl₃, 300 MHz): 8.16 (d, J=5.4 Hz, 1H), 7.56 (d, J=5.7 Hz, 1H); LRMS (ESI): m/z calcd for [M+H]⁺ 204.94, 206.94 found 205.1, 207.0.

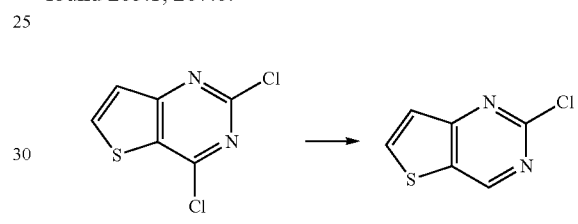

To a solution of the dichloride (11.9 g, 58 mmol) in EtOAc (250 mL) and EtOH (250 mL) was added 10% Pd/C (1.5 g) and NaHCO₃ (11 g, 130 mmol). The reaction was evacuated to a hydrogen atmosphere and stirred at room temperature 16 h. Further 10% Pd/C (560 mg) and NaHCO₃ (5.6 g, 66 mmol) were added and hydrogenation continued a further 19 h. The solids were removed by filtration through celite, concentration of the filtrate then afforded the product as an off-white solid (9.51 g, 96%). $^1$H NMR (CDCl₃, 300 MHz): 9.14 (s, 1H), 8.11 (d, J=5.7 Hz, 1H), 7.52 (d, J=5.4 Hz, 1H).

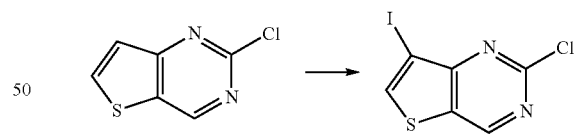

The thiophene (7.9 g, 47 mmol), periodic acid (5.3 g, 23 mmol) and ICl (11.4 g, 70 mmol) were mixed in acetic acid (60 mL) and heated at 80° C. for 2 h. The reaction was then partitioned between water and EtOAc and the aqueous layer extracted twice further with EtOAc. The combined organic fractions were washed with sat. aq. NaHCO₃ and brine, dried (MgSO₄) filtered and concentrated to afford 2-chloro-7-iodothieno[3,2-d]pyrimidine. Flash chromatography using CHCl₃ as eluent afforded 2-chloro7-iodo-thieno[3,2-d]pyrimidine as a yellow solid (5.15 g, 37%). $^1$HNMR (CDCl₃, 300 MHz): 9.11 (s, 1H), 8.23 (s, 1H); $^{13}$C NMR (CDCl₃, 75 MHz): 154.1, 153.9, 140.4, 140.3, 128.9, 80.1; LRMS (EI): m/z calcd for [M]⁺ 295.87, 297.87 found 295.90, 297.90.

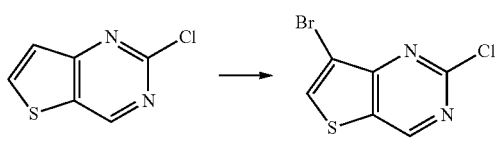 [SMILES: Clc1ncc2sccc2n1 ; Clc1ncc2scc(Br)c2n1]

To a solution of the thiophene (5 g, 29 mmol) in acetonitrile (50 mL) was added bromine (2.25 mL, 44 mmol) and periodic acid (3.3 g, 14 mmol). The reaction was heated under reflux for 2 hrs, then poured into ethyl acetate and partitioned against water and enough aqueous thiosulfate to discharge the bromine colour. The aqueous layer was extracted twice further with ethyl acetate and the combined organic fractions were washed with sat. aq. $NaHCO_3$ and brine, dried ($Na_2SO_4$) filtered and concentrated to afford, 7-bromo-2-chlorothieno [3,2-d]pyrimidine, as a cream/brown solid (5.46 g, 75%). $^1H$ NMR ($CDCl_3$, 300 MHz): δ 9.15 (s, 1H), 8.09 (s, 1H); LRMS (ESI): m/z calcd for $[M+H]^+$ 248.89, 250.89 found 248.9, 250.

Example 1

Synthesis of Compound 21

A mixture of 2-chloro-7-iodothieno[3,2-d]pyrimidine (500 mg, 1.69 mmol), 3-nitroaniline (280 mg, 2.03 mmol), p-TsOH.$H_2O$ (323 mg, 1.69 mmol) in 1,4-dioxane (10 mL) was heated in a microwave at 170° C. for 50 min, after which time a yellow precipitate formed. Water (20 mL) was added and the solid was collected by centrifugation and decanting off the liquid. The solid was washed with water (2×10 mL) then with ether (3×10 mL), and then dried by azeotroping twice with toluene. This provided compound 21 as a yellow solid (452 mg, 67%).

Example 2

Synthesis of Compound 20

To a mixture of compound 21 (90 mg, 0.226 mmol), phenylboronic acid (33 mg, 0.27 mmol) and $Pd[PPh_3]_4$ (13 mg, 0.0112 mmol) was added toluene (1.65 mL), n-propanol (0.54 mL) followed by 2 M aqueous $Na_2CO_3$ (0.34 mL, 0.68 mmol). The resulting suspension was then heated at 90° C. for 2 h. Thin layer chromatography analysis suggested no reaction had occurred. N,N-Dimethylformamide (1 mL) was then added and the resulting homogenous solution was heated at 90° C. for a further 4 h. After cooling to room temperature, saturated aqueous $NaHCO_3$ was added and the mixture was extracted three times with dichloromethane. The combined extracts were washed twice with water, brine then dried ($Na_2SO_4$). The solvent was removed under reduced pressure and the residue was purified by silica gel chromatography with 100% dichloromethane as eluent to afford compound 20 a bright yellow solid (35 mg, 45%).

Example 3

Synthesis of Compound 1

A mixture of 2-chloro-7-iodothieno[3,2-d]pyrimidine (593 mg, 2.0 mmol), 4-morpholinoaniline (500 mg, 2.8 mmol) and N,N-diisopropylethylamine (0.87 mL, 5.0 mmol) in NMP (13 mL) was heated in a microwave at 240° C. for 25 minutes. Water was added and the mixture was extracted three times with ethyl acetate. The combined extracts were washed with 2% aqueous citric acid, water, brine and dried ($Na_2SO_4$). The solvent was removed under reduced pressure and the residue was purified by silica gel chromatography with 15-30% ethyl acetate/dichloromethane as eluent to provide compound 1 as a bright yellow solid (618 mg, 70%).

Example 4

Synthesis of Compound 2

To a mixture of compound 1 (198 mg, 0.45 mmol), 4-aminophenyl boronic ester (118 mg, 0.54 mmol) and $Pd[PPh_3]_4$ (26 mg, 0.022 mmol) was added toluene (3.3 mL) and n-propanol (1.1 mL) followed by 2 M aqueous $Na_2CO_3$(0.675 mL, 1.35 mmol). The mixture was then heated at 90° C. for 18 h. After cooling to room temperature, water was added and the mixture was extracted three times with chloroform. The combined extracts were washed twice with brine then dried ($Na_2SO_4$). The solvent was removed under reduced pressure and the residue was purified by silica gel chromatography with 30-50% ethyl acetate/dichloromethane as eluent to afford compound 2 as a bright yellow solid (125 mg, 69%).

Example 5

Synthesis of Compound 3

To a suspension of compound 2 (95 mg, 0.235 mmol) in dichloromethane (2 mL) at room temperature was added triethylamine (100 μL, 0.717 mmol) followed by acrylic acid (32 μL, 0.467 mmol). 1-(3-Dimethylaminopropyl)-3-ethylcarbodiimide hydrochloride (EDC.HCl) (68 mg, 0.35 mmol) was added followed by 4-dimethylaminopyridine (3 mg) and the mixture was stirred for 16 h. More EDC.HCl (22 mg, 0.115 mmol) was added followed by N,N-dimethylformamide (0.5 mL) and stirring was continued for a further 24 h. The mixture was partitioned between water (50 mL) and dichloromethane (100 mL), with much precipitate forming in the aqueous layer. The organic layer was decanted off, the aqueous phase was filtered and the resulting solid was washed with water (2×5 mL), then with ethyl acetate (15 mL) to give compound 3 as a yellow solid (34 mg, 32%). The organic phase was concentrated to give additional low purity product (134 mg).

Example 6

Synthesis of Compound 26

To a solution of compound 21 (398 mg, 1.0 mmol) in methanol (10 mL) and NMP (10 mL) was added concentrated HCl (1.6 mL) followed by $SnCl_2.2H_2O$ (1.13 g, 5.0 mmol). The resulting yellow suspension was then heated at 65° C. for 1.25 h, after which time a red homogeneous solution resulted. The mixture was cooled to room temperature, water and ethyl acetate were added and the aqueous layer was adjusted to pH 10 with 28% aqueous ammonia. The layers were separated and the aqueous phase was extracted twice more with ethyl acetate. The combined extracts were washed twice with water, brine then dried ($Na_2SO_4$). The solvent was removed under reduced pressure to give compound 26 as an orange/brown solid (382 mg, 104%), containing a trace amount of NMP.

Example 7

Synthesis of Compound 22

To a mixture of compound 26 (60 mg, assumed 0.126 mmol), 2-ethylbenzeneboronic acid (23 mg, 0.153 mmol)

and Pd[PPh$_3$]$_4$ (7.3 mg, 0.0063 mmol) was added toluene (0.9 mL) and n-propanol (0.3 mL) followed by 2 M aqueous Na$_2$CO$_3$ (0.19 mL, 0.38 mmol). The mixture was then heated at 90° C. for 30 h. After cooling to room temperature, saturated aqueous NaHCO$_3$ was added and the mixture was extracted three times with ethyl acetate. The combined extracts were washed with water, brine then dried (Na$_2$SO$_4$). The solvent was removed under reduced pressure and the residue was purified by silica gel chromatography with 40% ethyl acetate/petroleum ether as eluent to afford compound 22 as a yellow foam (38 mg, 86%).

Example 8

Synthesis of Compound 4

To a mixture of compound 1 (400 mg, 0.91 mmol), 3-aminophenylboronic acid (150 mg, 1.1 mmol) and Pd[PPh$_3$]$_4$ (53 mg, 0.046 mmol) was added toluene (6.7 mL) and n-propanol (2.3 mL) followed by 2 M aqueous Na$_2$CO$_3$ (1.37 mL, 2.74 mmol). The mixture was then heated at 90° C. for 20 h. After cooling to room temperature, saturated aqueous NaHCO$_3$ was added and the mixture was extracted five times with chloroform. The combined extracts were washed with brine then dried (Na$_2$SO$_4$). The solvent was removed under reduced pressure and the residue was purified by silica gel chromatography with 30-60% ethyl acetate/dichloromethane as eluent to afford compound 4 as a bright yellow solid (168 mg, 46%).

Example 9

Synthesis of Compound 5

To a solution of compound 4 (77 mg, 0.19 mmol), acrylic acid (16 µL, 0.233 mmol) and HATU (72 mg, 0.19 mmol) in N,N-dimethylformamide (2 mL) at 0° C. was added N,N'-diisopropylethylamine (67 µL, 0.38 mmol). The mixture was stirred at 0° C. for 2.5 h, then allowed to warm to room temperature and stirring was continued for a further 16 h. Saturated aqueous NaHCO$_3$ (20 mL) was added and the mixture was extracted three times with dichloromethane. The combined extracts were washed with water, brine and dried (Na$_2$SO$_4$). The solvent was then removed under reduced pressure and the residue was purified by silica gel chromatography with 50% ethyl acetate/dichloromethane as eluent to afford compound 5 as a yellow solid (36 mg, 41%).

Example 10

Synthesis of Compound 11

To a solution of compound 1 (100 mg, 0.228 mmol) and 4-(4,4,5,5-tetramethyl-1,3,2-dioxaborolan-2-yl)benzenesulfonamide (97 mg, 0.343 mmol) in DMF (3 mL) and 2M aq. Na$_2$CO$_3$ (350 µL) was added Pd[PPh$_3$]$_4$ (26 mg, 0.22 mmol). The reaction vessel was sealed and heated at 100° C. for 15 h, then cooled, diluted with water (~20 mL) and the solids collected by filtration. The crude product was dissolved in hot methanol/DMF, filtered, then crystallized from methanol/DMF and water to provide compound 11 as a grey/green solid (77.5 mg, 78%).

Compounds 29 and 30 were prepared following the procedures reported above.

Example 11

Synthesis of Compound 8

To a solution of compound 1 (150 mg, 0.34 mmol) in methanol (10 mL) and triethylamine (143 µL, 1.03 mmol) was added Pd(dppf)Cl$_2$ (30 mg, 0.03 mmol). The reaction was evacuated to a carbon monoxide atmosphere and heated under reflux for 16 h. The reaction was cooled and the solvent removed in vaccuo to afford the crude material. Purification by flash chromatography using 30-70% EtOAc/DCM as eluent afforded compound 1 (61 mg, 40%) as well as compound 8 which was obtained as a yellow solid (51 mg, 68% based on recovered compound 1).

Example 12

Synthesis of Compound 17

To a solution of compound 8 (40 mg, 0.1 mmol) in THF (3 mL) and methonal (1 mL) was added water (1 mL) and lithium hydroxide (8 mg, 0.3 mmol). The reaction was stirred at rt 17 h, then ~5 mL of 5% aq. citric acid added and the methanol and THF removed. The precipitate that formed was collected by filtration and washed with water to afford the acid as a yellow solid (37.5 mg, 98%). To a suspension of the acid (37 mg, 0.1 mmol) in DCM (2 mL) and DMF (1 mL) was added triethylamine (72 µL, 0.52 mmol) and HATU (59 mg, 0.16 mmol). The reaction was sonicated for one minute then aminoacetonitrile hydrochloride (19.3 mg, 0.2 mmol) WAS added and the reaction allowed to stir at room temperature 16 h. The reaction was diluted with EtOAc and saturated aq. NaHCO$_3$, the layers partitioned and the aqueous layer extracted twice further with EtOAc. The combined aqueous fractions were washed with water and brine, dried (Na$_2$SO$_4$) filtered and evaporated to afford compound 17 as a yellow solid (35 mg, 86%).

Example 13

Synthesis of Compound 7

To a solution of 2-chlorothieno[3,2-d]pyrimidine (150 mg, 0.87 mmol) and 4-morpholinoaniline (188 mg, 1.05 mmol) in NMP (5 mL) was added diisopropylethylamine (337 µL, 1.93 mmol). The reaction was heated at 250° C. in a microwave reactor for 20 min, then diluted with EtOAc and 5% aq. citric acid. The aqueous layer was extracted twice further with EtOAc and the combined organic fractions washed with sat. aq. NaHCO$_3$, dried (Na$_2$SO$_4$) filtered and concentrated to afford the crude product. Purification by silica gel chromatography using 30-70% EtOAc/DCM as eluent then afforded the product as an orange gum. Trituration with EtOAc three times and collection of the fine solid afforded compound 7 as a dark yellow solid (26 mg, 10%).

Example 14

Synthesis of Compound 16

To a solution of 2-cyanoacetic acid (14 mg, 0.17 mmol) and triethylamine (46 µL, 0.33 mmol) in DCM (3 mL) was added HATU (46 mg, 0.12 mmol) and the mixture sonicated for one minute. The solution of activated acid was then added to compound 4 (45 mg, 0.11 mmol), washing with DCM (2×1 mL) and the reaction was stirred for 16 hrs at room temperature. The reaction mixture was diluted with EtOAc and sat.

aq. NaHCO₃ and the aqueous layer extracted twice further with EtOAc. The combine organic fractions were washed with water and brine dried (Na₂SO₄), filtered and concentrated. The glassy solid obtained was sonicated with 1:1 DCM:diethyl ether and the powder obtained washed twice further with diethyl ether to afford compound 16 as a yellow/green solid (33.1 mg, 63%).

Example 15

Synthesis of Compound 25

To a solution of compound 1 (123 mg, 0.28 mmol) and 3-(4,4,5,5-tetramethyl-1,3,2-dioxaborolan-2-yl)-N-(tert-butyl)benzenesulfonamide (143 mg, 0.42 mmol) in toluene (3 mL) were added n-propanol (1 mL), 2M aq. NaHCO₃ (420 μL) and Pd[PPh₃]₄ (32 mg, 0.03 mmol). The reaction was heated at 90° C. for 9 h, then partitioned between EtOAc and water. The aqueous layer was extracted twice further with EtOAc and the combined organic fractions washed with brine, dried (Na₂SO₄) filtered and concentrated. Silica gel chromatography using 50-100% EtOAc/Petroleum Spirit as eluent then provided compound 25 as a pale yellow solid (100 mg, 68%).

Preparation of 2-chloro-7-iodo-5H-pyrrolo[3,2-d]pyrimidine

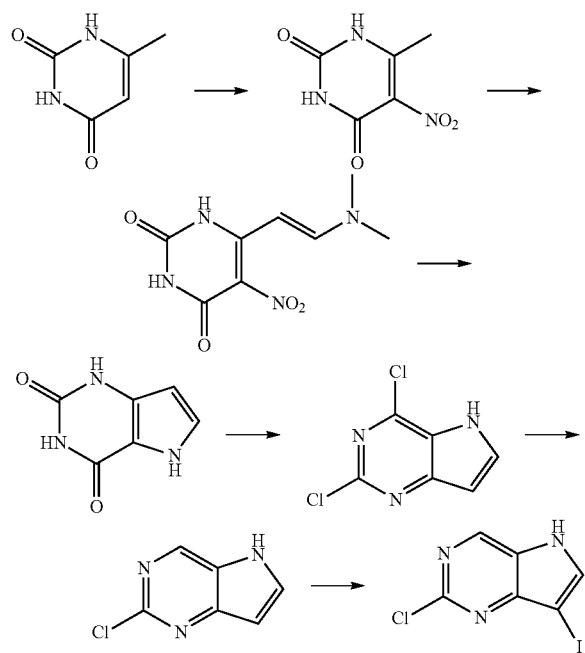

The procedure was adapted from that reported in *J. Med. Chem.* 1976, 19, 1072. 6-Methylpyrimidine-2,4(1H,3H)-dione (7.0 g, 55.56 mmol) was added to concentrated sulfuric acid (26 mL) cooled in ice at such a rate that the internal temperature did not exceed 40°. To this mixture fuming nitric acid (5.2 mL) was added dropwise whilst maintaining the temperature below 15°. The cooling bath was removed and the mixture was stirred at room temperature for 30 min then dumped into 100 ml of crushed ice. After stirring for 10 min the solid was collected and washed with cold water then dried in vacuo over phosphorus pentoxide. A yellow-green solid of 6-methyl-5-nitropyrimidine-2,4(1H,3H)-dione was obtained (7.92 g, 83%).

The procedure was adapted from that reported *J. Org. Chem.* 1978, 43, 2536. Dimethylfomamide-dimethyl acetal (4 mL, 30.05 mmol) was added to a warmed (80°) suspension of 6-methyl-5-nitropyrimidine-2,4(1H,3H)-dione (3 g, 17.54 mmol) in dimethylformamide (10 ml). The resultant mixture was heated to 140° for 30 min then allowed to cool to room temperature. The solid was collected by filtration and washed with ethyl acetate then dried in vacuo to afford 6-[(e)-2-(dimethylamino)vinyl]-5-nitropyrimidine-2,4(1H,3H)-dione (2.62 g, 66%).

A suspension of 6-[(e)-2-(dimethylamino)vinyl]-5-nitropyrimidine-2,4(1H,3H)-dione (1.43 g, 6.36 mmol) in acetic acid (23 mL) was heated to 80° then zinc dust (2 g, 30.77 mmol) was added slowly over 1 h. The resulting suspension was heated for a further 1 h then allowed to cool to room temperature. The solid was collected by filtration then washed with acetic acid. The solid was transferred to a beaker and washed with water (25 mL), collected then dissolved in sodium hydroxide (5%, 10 mL). This solution was warmed to 70° and stirred for 30 min. Acetic acid was added until pH 5-6 then the precipitate collected and washed with cold water then ethanol. The resultant solid was dried in vacuo to furnish 1H-pyrrolo[3,2-d]pyrimidine-2,4(3H,5H)-dione (0.62 g, 65%).

A suspension of 1H-pyrrolo[3,2-d]pyrimidine-2,4(3H,5H)-dione (0.38 g, 2.52 mmol) in phosphorus oxychloride (30 mL) was heated to 120° for 6 h during which the mixture became clear and homogeneous. The mixture was allowed to cool to room temperature and the excess phosphorus oxychloride was removed in vacuo. The residue was cooled in ice, cold ammonium hydroxide (30 mL, pH=8) was added and the mixture stirred for 30 min. The precipitate was collected and washed with cold water. The solid was dried in vacuo to afford 2,4-dichloro-5H-pyrrolo[3,2-d]pyrimidine (0.33 g, 70%).

To a solution of 2,4-dichloro-5H-pyrrolo[3,2-d]pyrimidine (6.6 g, 35.3 mmol) in ethanol (200 mL) was added sodium hydrogen carbonate (2.96 g) and Palladium on carbon (10%, 0.66 g). The mixture was stirred under an atmosphere of hydrogen at room temperature for 3 h. The mixture was filtered then filtrate absorbed onto silica gel. Flash chromatography, eluting with chloroform/methanol 4/1, afforded 2-chloro-5H-pyrrolo[3,2-d]pyrimidine (3.3 g, 61%). Also recovered from the column was 5H-pyrrolo[3,2-d]pyrimidine (1.5 g)

To a suspension of 2-chloro-5H-pyrrolo[3,2-d]pyrimidine (3.55 g, 23.2 mmol) in water (200 ml) was added sodium bicarbonate (19.2 g) A solution of potassium iodide (16.41 g, 98.9 mmol) and iodine (5.78 g, 22.8 mmol) in water (25 ml) was added dropwise then allowed to stir at room temperature for 1 h. The mixture was diluted with brine and extracted with ethyl acetate. The extracts were dried filtered and evaporated. The residue was purified by flash chromatography, eluting with chloroform/methanol 25/1 to 20/1, to afford 2-chloro-7-iodo-5H-pyrrolo[3,2-d]pyrimidine (5.33 g, 83%). ¹H NMR (DMSO, 300 MHz): 12.50 (s, 1H), 8.82 (s, 1H), 8.20 (s, 1H); ¹³C NMR (DMSO, 75 MHz): 143.2, 143.0, 139.7, 139.5, 126.5, 56.2; LRMS (EI): m/z calcd for [M]⁺ 278.91, 280.91 found 278.95, 280.95.

Example 16

Synthesis of Compound 33

Step 1. Preparation of 2-chloro-7-iodo-5-methyl-5H-pyrrolo[3,2-d]pyrimidine To a suspension of 2-chloro-7-iodo-5H-pyrrolo[3,2-d]pyrimidine (1 g, 3.57 mmol, 1.0 eq.) and NaOH (0.430 mg, 10.73 mmol, 3.0 eq.) in DCM (28 ml) was added iodomethane (0.66 g, 4.6 mmol, 1.3 eq.) and tetrabutylammonium bromide (0.116 g, 0.36 mmol, 0.1 eq.). The reaction mixture was stirred at room temperature overnight. Water was poured in and the aqueous layer extracted with ethyl acetate (2 times). The combined organic layers were then dried over $Na_2SO_4$. After filtration and evaporation the yellow residue was triturated with a mixture of ethyl acetate/petroleum spirit (1:2) to give the product as a white solid (0.73 g, 70%). $^1$H NMR (DMSO, 300 MHz): 8.99 (s, 1H), 8.17 (s, 1H), 3.94 (s, 3H); LRMS (EI): m/z calcd for $[M+H]^+$ 293.93 found 294.1.

Step 2. Preparation of N-[3-(2-chloro-5-methyl-5H-pyrrolo[3,2-d]pyrimidin-7-yl)phenyl]methane-sulfonamide To a solution of 2-chloro-7-iodo-5-methyl-5H-pyrrolo[3,2-d]pyrimidine (0.140 g, 0.48 mmol, 1.0 eq.) in DMF (6 ml) was added 3-methanesulfonylaminophenylboronic acid (0.124 g, 0.576 mmol, 1.2 eq.) followed by aqueous $Na_2CO_3$ (2M, 0.7 ml, 1.44 mmol, 3.0 eq.). A flow of nitrogen was bubbled through the mixture during 15 to 20 min before adding $Pd[PPh_3]_4$ (0.055 g, 0.048 mmol, 0.1 eq.). The mixture was then heated up to 100° C. overnight. After cooling down the reaction mixture to room temperature a large amount of water (around 60 ml) was added and the mixture extracted with ethyl acetate (3 times). After evaporation the residue was purified by column chromatography using petroleum spirit/ethyl acetate (1:4) as eluent. The product was obtained as a pale yellow solid (110 mg, 68%). LRMS (EI): m/z calcd for $[M+H]^+$ 337.05 found 337.2.

Step 3. Preparation of Compound 33

The compound N-[3-(2-chloro-5-methyl-5H-pyrrolo[3,2-d]pyrimidin-7-yl)phenyl]-methanesulfonamide (100 mg, 0.30 mmol, 1.0 eq.) was dissolved in NMP (1.2 ml). To the solution 4-morpholinoaniline (74 mg, 0.48 mmol, 1.4 eq.) was added followed by N,N-diisopropylethylamine (0.132 ml, 0.75 mmol, 2.5 eq.). The mixture was heated in a microwave reactor at 240° C. for 35 min. An aliquot was then taken and analysed by LCMS. LCMS analysis showed little reaction so the mixture was then heated further at 240° C. over 5 h. To the black resulting mixture was then added a large amount of water. The aqueous suspension was then extracted several times with ethyl acetate. The organic layers were evaporated to give a black residue. Flash chromatography (9:1 ethyl acetate/petroleum spirit) afforded a white solid which was triturated with diethyl ether to afford compound 33 (3.4 mg, 2%).

Compound 34 was prepared using the procedures reported above.

Example 17

Synthesis of Compound 12

To a solution of Compound 1 (100 mg, 0.228 mmol) and 3-(4,4,5,5-tetramethyl-1,3,2-dioxaborolan-2-yl)-N,N-dimethylbenzenesulfonamide (106 mg, 0.34 mmol) in DMF (3 mL) were added 2M aq. $NaHCO_3$ (350 µL) and $Pd[PPh_3]_4$ (26 mg, 0.02 mmol). The reaction was heated at 100° C. for 15 h, allowed to cool, and then diluted with water (20 mL). The resultant precipitate was collected by filtration and air-dried. The crude product was re-dissolved in hot methanol/DMF, filtered hot, and then sufficient water was added to cause the solution to become cloudy. After cooling to room temperature and then further in an ice-bath, the solid was collected by filtration, washed with water and air-dried, followed by further drying under reduced pressure. This provided Compound 12 as a yellow/brown solid (65 mg, 57%).

Example 18

Synthesis of Compound 14

To a solution of Compound 1 (100 mg, 0.228 mmol) and N-4-methanesulfonamide phenylboronic acid (74 mg, 0.34 mmol) in DMF (3 mL) were added 2M aq. $NaHCO_3$ (350 µL) and $Pd[PPh_3]_4$ (26 mg, 0.02 mmol). The reaction was heated at 100° C. for 15 h, allowed to cool, and then diluted with water (20 mL). The resultant precipitate was collected by filtration and air-dried. The crude product was re-dissolved in hot methanol/DMF, filtered hot, and then sufficient water was added to cause the solution to become cloudy. After cooling to room temperature and then further in an ice-bath, the solid was collected by filtration, washed with water and air-dried, followed by further drying under reduced pressure. This provided Compound 14 as a yellow/green solid (66 mg, 60%).

Example 19

Synthesis of Compound 15

To a solution of Compound 1 (100 mg, 0.228 mmol) and 2-Methoxy-4-(4,4,5,5-tetramethyl-1,3,2-dioxaborolan-2-yl) phenol (86 mg, 0.34 mmol) in DMF (3 mL) were added 2M aq. $NaHCO_3$ (350 µL) and $Pd[PPh_3]_4$ (26 mg, 0.02 mmol). The reaction was heated at 100° C. for 15 h, allowed to cool, and then diluted with water (20 mL). The resultant precipitate was collected by filtration and air-dried. The crude product was re-dissolved in hot methanol/DMF, filtered hot, and then sufficient water was added to cause the solution to become cloudy. After cooling to room temperature and then further in an ice-bath, the solid was collected by filtration, washed with water and air-dried, followed by further drying under reduced pressure. This provided Compound 15 as a brown solid (54 mg, 55%).

Example 20

Synthesis of Compound 19

To a solution of Compound 1 (100 mg, 0.228 mmol) and 1-ethyl-3-(4-(4,4,5,5-tetramethyl-1,3,2-dioxaborolan-2-yl)-2-(trifluoromethoxy)phenyl)urea (128 mg, 0.34 mmol) in DMF (3 mL) were added 2M aq. $NaHCO_3$ (350 µL) and $Pd[PPh_3]_4$ (26 mg, 0.02 mmol). The reaction was heated at 100° C. for 15 h, allowed to cool, and then diluted with water (20 mL). The resultant precipitate was collected by filtration and air-dried. The crude product was re-dissolved in hot methanol/DMF, filtered hot, and then sufficient water was added to cause the solution to become cloudy. After cooling to room temperature and then further in an ice-bath, the solid was collected by filtration, washed with water and air-dried, followed by further drying under reduced pressure. This provided Compound 19 as a yellow solid (45 mg, 41%).

Example 21

Synthesis of Compound 28

To a suspension of compound 19 (40 mg, 0.072 mmol) in 1,4-dioxane (1 mL) in a microwave tube was added 2M aq. NaOH (200 µL). The mixture was processed in a microwave reactor (power=300 W, temp=180° C.) for 30 minutes. The reaction mixture was poured onto water and extracted with DCM (4×). The combined organic phase was dried ($MgSO_4$) and concentrated in vacuo. The crude product was purified by column chromatography on silica to provide compound 28 as a light brown solid (18 mg, 51%).

Example 22

Synthesis of Compound 31

To a solution of compound 18 (0.11 mmol) in DMF (2 mL) was added $Cs_2CO_3$ (80 mg, 0.25 mmol) followed by bromoacetonitrile (15 µL, 0.22 mmol) at room temperature. The mixture was stirred for 15 hours, then poured onto water, saturated with sodium chloride and extracted with THF (3×). The combined extracts was dried ($MgSO_4$) and concentrated in vacuo. The crude product was partially dissolved in ether and then diluted with two volumes of petroleum ether. The solid was collected by filtration and dried. This provided compound 31 as a brown solid (15 mg, 26%)

Compound 32 was prepared using the procedures reported above.

Example 23

Synthesis of Compound 9

A solution of 2-chloro-5H-pyrrolo[3,2-d]pyrimidine (100 mg, 0.65 mmol), p-morpholino-aniline and p-TsOH.$H_2O$ (150 mg, 0.78 mmol) in dioxane was heated under reflux for 3 days. The dioxane was removed in vacuo and ethyl acetate added. The solution was washed with saturated sodium bicarbonate then with 2% aqueous citric acid. The resultant solid was purified by flash chromatography (4:1 ethyl acetate/petroleum spirit) to afford compound 9 (10 mg, 5%).

Example 24

Synthesis of Compound 61

To a solution of 7-bromo-2-chlorothieno[3,2-d]pyrimidine (1.18 g, 4.7 mmol) and 4-(2-pyrrolidin-1-ylethoxy)aniline (1.27 g, 6.15 mmol) in THF (15 mL) was added potassium t-butoxide (637 mg, 5.68 mmol). The reaction was heated at reflux 65 hrs, then cooled and poured into ethyl acetate/water. The aqueous layer was extracted twice further with ethyl acetate and the combined organic layers were washed with brine, dried ($Na_2SO_4$) filtered and concentrated to afford a brown/orange gum. Silica gel chromatography using 5% methanol, 0.5% aqueous ammonia in ethyl acetate as an eluent afforded compound 61 as a yellow/orange oil which solidified on standing (459 mg, 23%).

Example 25

Synthesis of Compound 71

To a solution of compound 61 (100 mg, 0.24 mmol) and N-tert-butyl-3-(4,4,5,5-tetramethyl-1,3,2-dioxaborolan-2-yl)benzenesulfonamide (200 mg, 0.61 mmol) in toluene (3 mL), n-propanol (0.5 mL) and aqueous sodium carbonate (2M, 1 mL, 0.2 mmol) was added $Pd[PPh_3]_4$ (55 mg, 0.05 mmol). The reaction was heated at 95° C. for 18 hrs then partitioned between ethyl acetate and water. The aqueous layer was further extracted with ethyl acetate, then washed with water and brine, dried ($Na_2SO_4$) filtered and concentrated to afford the crude product. Purification by flash chromatography using 0-100% 89:10:1 dichloromethane:methanol:aqueous ammonia provided compound 71 as a glassy orange solid (32.4 mg, 25%).

Example 26

Synthesis of Compound 39

To a solution of compound 1 (100 mg, 0.23 mmol) and 2-isopropylaniline (48 uL, 0.34 mmol) in toluene (3 mL) was added sodium t-butoxide (44 mg, 0.45 mmol), tris[dibenzylideneacetone]dipalladium(0) (5.2 mg, 0.005 mmol) and 4,5-bis(diphenylphosphino)-9,9-dimethylxanthene (7.1 mg, 0.013 mmol). The reaction was heated under reflux for 3 hrs, then cooled and partitioned between ethyl acetate and water. The aqueous layer was extracted with ethyl acetate and the combined organics were washed with brine, dried ($Na_2SO_4$) filtered and concentrated to afford the crude product. Purification by silica gel chromatography using 0-50% ethyl acetate/petroleum spirits as eluent afforded compound 39 as a yellow solid (24.4 mg, 24%).

Example 27

Synthesis of Compound 49

An aliquot (0.35 ml) of a solution of 4-nitrosulfenyl chloride in toluene (50 mg/ml, 0.18 mmol) was added to a solution of compound 7 (50 mg, 0.17 mmol) in acetonitrile (3 ml). The mixture was allowed to stir for 4.5 hrs at room temperature and the resultant precipitate was collected. The filtrate was evaporated and added to the precipitate. The combined material (56 mg) was purified by flash chromatography (12 mg) followed by preparative HPLC to afford compound 49 (2.5 mg, 3%).

Example 28

Synthesis of Compound 101

Step 1: Preparation of 2-chloro-7-phenylthieno[3,2-d]pyrimidine

A mixture of 7-bromo-2-chlorothieno[3,2-d]pyrimidine (1.0 g, 4.0 mmol), phenyl boronic acid (0.6 g, 4.9 mmol), $Pd[PPh_3]_4$ (0.47 g, 0.4 mmol) and aqueous sodium carbonate (2M, 4.5 mL, 9.0 mmol) in toluene (25 mL)/isopropanol (8 mL) was heated under reflux overnight. The mixture was allowed to cool to room temperature, was diluted with ethyl acetate then washed with 10% aqueous sodium bicarbonate, dried ($Na_2SO_4$) filtered and concentrated. The resultant solid was sonicated in diethyl ether (2×70 mL) and the combined ether washes were evaporated to afford the crude product (1.4 g), still containing starting material and $OPPh_3$.

Step 2: Preparation of Compound 101

A mixture of crude 2-chloro-7-phenylthieno[3,2-d]pyrimidine from above (0.30 g, ~1.2 mmol), 3,4-dimethoxyaniline (0.18 g, 1.2 mmol) and potassium t-butoxide (0.26 g, 2.3 mmol) in THF (10 ml) was heated under reflux for 35 hrs. The mixture was allowed to cool to room temperature, HCl (4M, 0.5 mL) was added then the THF removed in vacuo. Ethyl acetate and water were added followed by more HCl (10 mL). The organic phase was removed, dried ($Na_2SO_4$) filtered and concentrated. The resultant material (0.30 mg) was purified by flash chromatography (0.13 g) followed by C18 chromatography to afford compound 101 (24 mg, 5%) and compound 100 (34 mg).

Compound Analysis $^1$H NMR data was acquired on a Bruker 300 MHz NMR Spectrometer. LC MS data was acquired on a Waters LC MS system operating under Masslynx software control and consisting of 2695Xe HPLC, 2996 PDA detector and ZQ single quadrupole mass spectrometer over a m/z range of 100-650 with cone voltage of 30 V, with nitrogen desolvation gas (500 L/h) and cone gas (100 L/h), source temperature set to 120° C. and desolvation temperature set to 140° C. The HPLC conditions were one of the following:

(a) Column: XTerra MS $C_{18}$, 3.5 micron, 2.1×50 mm
Flow rate: 0.25 mL/min
Solvent Gradient:

| Time | % MilliQ water | % ACN | Curve |
|---|---|---|---|
| 0 | 90 | 10 | 1 |
| 5 | 0 | 100 | 6 |
| 6 | 0 | 100 | 6 |
| 7 | 90 | 10 | 6 |
| 10 | 90 | 10 | 6 |

(b) Column: XTerra MS $C_{18}$, 3.5 micron, 2.1×50 mm
Flow rate: 0.25 mL/min
Solvent Gradient:

| Time | % MilliQ water | % ACN | 0.5% formic acid$_{(aq)}$ | Curve |
|---|---|---|---|---|
| 0 | 90 | 0 | 10 | 1 |
| 0.5 | 90 | 0 | 10 | 6 |
| 5.5 | 0 | 90 | 10 | 6 |
| 7.5 | 0 | 90 | 10 | 6 |
| 8.5 | 90 | 0 | 10 | 6 |
| 11.5 | 90 | 0 | 10 | 6 |

Example 29

Enzyme Screening

Compound Dilution

For screening purposes, compounds (in 100% DMSO) were warmed at 37 degrees for at least 20 minutes before use. A 20 μm stock was initially made in assay buffer, where the final concentration of DMSO was 0.3%. The stocks were then diluted in 384 well Optiplates (Packard) where the final concentration of the compound was 5 μM.

JAK Tyrosine Kinase Domain Production

JAK kinase domains were produced using the following procedures:

JAK1

The kinase domain of human JAK1 was amplified from U937 mRNA using the polymerase chain reaction with the following primers:

```
XHOI-J1
                                       (SEQ. ID. NO: 1)
5'-CCG CTC GAG ACT GAA GTG GAC CCC ACA CAT-3'

J1-KPNI
                                       (SEQ. ID. NO: 2)
5'-CGG GGT ACC TTA TTT TAA AAG TGC TTC AAA-3'
```

The JAK1 PCR products were cloned into the pDest20 destination vector (Gibco). The JAK1 plasmid was then transformed into competent DH10Bac cells (Gibco), and the recombinant baculovirus was prepared via Sf9 insect cell transfection.

JAK2

The kinase domain of human JAK2 was amplified from U937mRNA using the polymerase chain reaction with the following primers:

```
SALI-jk2
                                       (SEQ. ID. NO: 3)
5'-ACG CGT CGA CGG TGC CTT TGA AGA CCG GGA T-3' jk2-NOTI
                                       (SEQ. ID. NO: 4)
5'-ATA GTT TAG CGG CCG CTC AGA ATG AAG GTC ATT
T-3'
```

The JAK2 PCR products were cloned into the pDest20 destination vector (Gibco). The JAK2 plasmid was then transformed into competent DH10Bac cells (Gibco), and the recombinant baculovirus was prepared via Sf9 insect cell transfection.

JAK3

The kinase domain of human JAK3 was amplified from U937 mRNA using the polymerase chain reaction with the following primers:

```
XHOI-J3
                                       (SEQ. ID. NO: 5)
5'-CCG CTC GAG TAT GCC TGC CAA GAC CCC ACG-3'

J3-KPNI
                                       (SEQ. ID. NO: 6)
5'-CGG GGT ACC CTA TGA AAA GGA CAG GGA GTG-3'
```

The JAK3 PCR products were cloned into the pDest20 destination expression vector (Gibco). The JAK3 plasmid was then transformed into competent DH10Bac cells (Gibco), and the recombinant baculovirus was prepared via Sf9 insect cell transfection.

Large Scale Production of Kinase Domains

Baculovirus preparations from each of the JAK family members were infected into one litre of Sf9 (*Spodoptera frugiperda*) cells (Invitrogen) grown in SF900II serum free medium (Invitrogen) to a cell density of approximately 2×10$^6$ cells/ml. Cells were infected with virus at a cell culture to virus stock ratio of 20:1. Cells were harvested and lysed 48 hours post infection. The GST-tagged JAK kinase domains were purified by affinity chromatography on a GSH agarose column (Scientifix).

Assay Protocols

Kinase assays were performed in 384 well Optiplates (Packard) using an Alphascreen Protein Tyrosine KinaseP100 detection kit. The compounds were pre-incubated with affinity purified PTK domain in the presence of phosphotyrosine assay buffer (10 mM HEPES, pH 7.5, 100 mM $MgCl_2$, 25 mM NaCl, 200 mM sodium vanadate and 0.1% Tween 20) for 20 minutes. The compounds were then incubated with substrate in the presence of either 80 or 625um ATP for 60 or 90 minutes. The substrate used was either substrate-1 with the sequence biotin-EGPWLEEEEEAYGWMDF-NH$_2$ (SEQ ID NO: 7) (final concentration 111 μM) or substrate-2 substrate with the sequence biotin-EQEDEPEGDYFEWLEPE (SEQ ID NO: 8) (final concentration 133 μM). Alphascreen phosphotyrosine acceptor beads followed by streptavidin donor beads at a concentration of 1/100 in stop buffer were added to each well under subdued light and incubated for 2-3 hours. The Alphascreen plates were read on a Packard Fusion Alpha instrument.

Results The enzyme assay results and structural data for selected compounds is given below in Table 1, where +++ is <100 nM, ++ is <500 nM and + is <1 μM Example 30

Cellular Screening

Compound Dilution

For screening purposes, compounds were diluted in 96 well plates at a concentration of 20 μM. Plates were warmed at 37° C. for 30 minutes before the assay was performed.
Establishment of the TEL:JAK2 Cell Line The coding region encompassing nucleotides 1-487 of TEL was amplified by PCR using the oligonucleotides 5TEL (5'-GGA GGA TCC TGA TCT CTC TCG CTG TGA GAC-3') (SEQ ID NO: 9) and 3TEL (5'-AGGC GTC GAC TTC TTC TTC ATG GTT CTG-3') (SEQ ID NO: 10) and U937 mRNA as a template. A BamHI restriction site was incorporated into the 5TEL primer, and a Sal I restriction site was incorporated into the 3TEL primer. The regions encompassing the kinase domain of JAK2 (nucleotides 2994-3914; JAK2F 5'-ACGC GTC GAC GGT GCC TTT GAA GAC CGG GAT-3' (SEQ ID NO: 11); JAK2R 5'-ATA GTT TAG CGG CCG CTC AGA ATG AAG GTC ATT T-3') (SEQ ID NO: 12) and JAK3 (nucleotides 2520-3469; JAK3F 5'-GAA GTC GAC TAT GCC TGC CAA GAC CCC ACG ATC TT-3') (SEQ ID NO: 13) were generated by PCR using Taq DNA polymerase (Gibco/BRL) and U937 mRNA as a template. A Sal I restriction site was incorporated into the forward primer of JAK2 and JAK3, a Not I site was incorporated into the JAK2 reverse primer and a Xba I site was added to the reverse primer of JAK3.

A TEL/Jak2 fusion was generated by digestion of the TELPCR product with BamH I/Sal I restriction enzymes, digestion of the JAK2 PCR product with Sal I/Not I restriction enzymes, followed by ligation and subcloning of the ligation product into the mammalian expression Vector pTRE 2 (Clontech), which was prepared by digestion with BamH I-Not I restriction enzymes, to give the the TEL/Jak fusion plasmid pTELJAK2.

The TEL/Jak3 fusion was prepared by ligation of the JAK3 Sal I/Not I cleaved kinase domain PCR product with the BamH I/Sal I restriction digested TEL product, followed by ligation of the ligation product into the BamH I/Not I digested pTRE2, to give the TEL/Jak3 fusion plasmid pTELJAK3.

The growth factor dependant myelomonocytic cell line BaF3 bearing the pTET-off plasmid (Clontech) was transfected with either pTELJAK2 or pTELJAK3, and the transfected cells were selected for growth-factor independent cell growth. The BaF3 wild-type cells were cultured in DMEM containing 10% FCS, 10% WEHI 3B conditioned medium. The BaF3 TELJAK cells (BafT_J2 or BafT_J2) were cultured in DMEM 10% Tet-System Approved FBS (without WEHI 3B conditioned medium).

Cellular Assays were Performed as Follows:

Cell suspensions were prepared by harvesting cells from culture. (the cells used in this test were in late log phase growth with high viability.) Cells were diluted in the appropriate growth medium, as described above, to 1.1× final concentration (from 50,000 cell/mL to 200,000 cell/mL, depending on cell line).

Compounds to be tested were added (10 μL, 10× final concentration) to a flat bottomed 96-well plate. The cellular suspension (90 μL per well) was then added, and the plate incubated for 40 hr at 37° C., 5% CO$_2$. Alamar Blue 10 μL per well was added and the plates returned to the incubator for a further 4-6 hours. The plates were then read at 544 nm.

Results

Result are given in Table 1 where +++ is <1 μM, ++ is <5 μM and + is <20 μM

TABLE 1

| | JAK1 IC$_{50}$_nM | JAK2 IC$_{50}$_nM | JAK3 IC$_{50}$_nM | BafT_J2 IC$_{50}$_nM | BAF3wt IC$_{50}$_nM | BafT_J3 IC$_{50}$_nM | CTLL2 IC$_{50}$_nM |
|---|---|---|---|---|---|---|---|
| 2 | NT | +++ | +++ | +++ | +++ | +++ | +++ |
| 3 | NT | +++ | +++ | ++ | ++ | +++ | +++ |
| 4 | NT | +++ | +++ | +++ | +++ | +++ | +++ |
| 5 | NT | +++ | +++ | ++ | +++ | +++ | +++ |
| 10 | NT | +++ | +++ | +++ | +++ | +++ | +++ |
| 11 | +++ | +++ | +++ | +++ | ++ | ++ | +++ |
| 13 | ++ | +++ | +++ | +++ | +++ | ++ | ++ |
| 14 | +++ | +++ | +++ | +++ | +++ | +++ | +++ |
| 15 | +++ | +++ | +++ | +++ | >20000 | >20000 | >20000 |
| 16 | +++ | +++ | +++ | +++ | +++ | +++ | +++ |
| 18 | +++ | +++ | +++ | +++ | +++ | +++ | +++ |
| 22 | NT | +++ | +++ | +++ | ++ | ++ | +++ |
| 29 | NT | +++ | +++ | +++ | +++ | +++ | +++ |
| 30 | NT | +++ | +++ | +++ | +++ | +++ | ++ |
| 31 | +++ | +++ | +++ | +++ | +++ | +++ | +++ |
| 32 | NT | +++ | +++ | +++ | ++ | +++ | +++ |
| 34 | +++ | +++ | ++ | +++ | + | >20000 | >20000 |
| 35 | NT | +++ | + | ++ | ++ | + | ++ |
| 37 | NT | +++ | +++ | +++ | +++ | +++ | +++ |
| 44 | NT | +++ | +++ | +++ | ++ | ++ | ++ |
| 45 | NT | +++ | +++ | +++ | +++ | +++ | +++ |
| 47 | +++ | +++ | ++ | ++ | ++ | ++ | ++ |
| 48 | +++ | +++ | ++ | +++ | +++ | +++ | +++ |
| 50 | +++ | +++ | ++ | +++ | +++ | +++ | +++ |
| 52 | NT | +++ | +++ | +++ | +++ | +++ | +++ |

TABLE 1-continued

| | JAK1 IC$_{50}$_nM | JAK2 IC$_{50}$_nM | JAK3 IC$_{50}$_nM | BafT_J2 IC$_{50}$_nM | BAF3wt IC$_{50}$_nM | BafT_J3 IC$_{50}$_nM | CTLL2 IC$_{50}$_nM |
|---|---|---|---|---|---|---|---|
| 53 | +++ | +++ | ++ | +++ | +++ | +++ | ++ |
| 55 | NT | +++ | +++ | ++ | ++ | ++ | ++ |
| 56 | NT | +++ | +++ | ++ | ++ | ++ | ++ |
| 58 | NT | +++ | ++ | +++ | +++ | +++ | +++ |
| 62 | NT | +++ | +++ | +++ | +++ | +++ | +++ |
| 63 | NT | +++ | +++ | +++ | +++ | +++ | +++ |
| 65 | NT | +++ | +++ | +++ | ++ | +++ | ++ |
| 68 | NT | +++ | ++ | +++ | +++ | +++ | ++ |
| 70 | NT | +++ | +++ | +++ | +++ | +++ | ++ |
| 71 | NT | +++ | +++ | +++ | ++ | +++ | ++ |
| 72 | NT | +++ | +++ | +++ | ++ | +++ | +++ |
| 73 | NT | +++ | +++ | +++ | +++ | +++ | ++ |
| 74 | NT | +++ | ++ | +++ | ++ | ++ | ++ |
| 76 | NT | +++ | ++ | +++ | +++ | +++ | +++ |
| 79 | NT | +++ | +++ | +++ | ++ | ++ | +++ |
| 81 | NT | +++ | ++ | +++ | +++ | +++ | +++ |
| 83 | NT | +++ | +++ | +++ | +++ | +++ | +++ |
| 84 | NT | +++ | ++ | +++ | +++ | +++ | +++ |
| 85 | NT | +++ | +++ | +++ | +++ | +++ | +++ |
| 87 | NT | +++ | +++ | +++ | +++ | +++ | +++ |
| 88 | NT | +++ | +++ | +++ | +++ | +++ | +++ |
| 89 | NT | +++ | +++ | +++ | +++ | +++ | +++ |
| 90 | NT | +++ | +++ | +++ | +++ | +++ | +++ |
| 91 | NT | +++ | +++ | +++ | +++ | +++ | +++ |
| 92 | NT | +++ | ++ | ++ | +++ | ++ | +++ |
| 93 | NT | +++ | +++ | +++ | +++ | +++ | +++ |
| 94 | NT | +++ | ++ | +++ | +++ | +++ | +++ |
| 95 | NT | +++ | +++ | +++ | +++ | +++ | +++ |
| 96 | NT | +++ | +++ | +++ | +++ | +++ | +++ |
| 97 | NT | +++ | +++ | +++ | +++ | +++ | +++ |
| 98 | NT | +++ | +++ | +++ | +++ | +++ | +++ |

(NT = Not Tested)

Example 31

Testing of Compounds in Disease Models

The effect of the compounds on tumor initiation, progression and metastasis can be evaluated in relevant in vivo animal efficacy models. Models could be human tumor xenografts models in immuno-deficient mice, from human tumor cell lines or preferably from primary or metastatic human tumors. Other models might be human tumor xenografts grown in orthotopic sites, models of disseminated disease and transgenic or labeled tumors models. Models could also include surgical resection of primary tumor and evaluation of metastatic disease.

Models could be selected to ensure that the molecular drug targeted is expressed. Examples of tumors displaying deregulation of the JAK/STAT pathway include prostate carcinoma, breast cancer, colon carcinoma, including leukemia, lymphoma, myeloma, ovarian tumors, melanoma, lung carcinoma, glioma, renal-cell tumors.

Efficacy can be measured in these models by various outcomes depending on tumor type (solid, leukemia or metastatic) and might include measure of tumor onset, tumor growth rate, tumor burden, tumor growth delay, tumor cell kill, incidence of metastasis, imaging of tumor and invasiveness/metastasis by various approaches including labeled cells or reagents, survival, angiogenesis, histopathology.

The in vivo animal efficacy models might also be used for determination of the additivity or synergy of the effect of the compounds in combination with other drugs, Rheumatoid arthritis (RA) is a chronic, destructive inflammatory polyarticular joint disease characterised by passive synovial proliferation and subintimal infiltration of inflammatory cells. Although the aetiology remains to be elucidated, it is generally acknowledged that RA is an autoimmune disease and arthritis is a consequence of loss of tolerance against a cartilage specific autoantigen. In this context, animal models have been established that evolves around induction of RA by an autoantigen such as 1. type II collagen-induced arthris (CIA) and 2. a combination of an antigen from gram-ve bacteria (LPS) with a panel of 4 monoclonal antibodies (mAb). A third model of arthritis is the Adjuvant-induced arthritis (AIA) which is performed mainly in rats. The underlying mechanism of AIA is still controversial. However, a 65 kD myobacterial heat shock protein was shown to share a nonapeptide sequence in the core protein molecule of proteoglycan, and suggests that AIA is also a disease inducible by autologous antigen.

In AIA, eight-week old Lewis rats were given Complete Freund's Adjuvant (CFA) prepared by suspending as an emulsion of heat-killed *Mycobacterium butyricum* in liquid paraffin at 12 mg/ml. CFA-induced arthritis can be stimulated by injection of 50 µl of CFA emulsion intradermally either in to the footpad or to the base of the tail. From day 7 (onset of arthritis), rats are examined daily for clinical arthritic score on a 0-4 scale: 0, normal; 1, minimal swelling; 2, medium swelling; 3, severe swelling; and 4, severe and non-weight bearing. For each limb, the mid-forpaw, the wrist, the joints of the fingers, the midfoot, the ankle and the joints of the digits are scored giving a maximum clinical score of 48 per rat. The animals are sacrificed on day 17 and the hindpaws are amputated and fixed in 7.4% formalin. After decalcification and embedment in paraffin, the limbs are sectioned in a mid-sagittal plane, stained by eosin and hematoxylin and examined microscopically for pannus formation (cartilage and bone erosion and destruction), vascularity (blood vessel formation by CD31 staining) and mononuclear cell infiltration (T,B and macrophages).

In CIA, DBA/1 mice that bear H-2$^q$MHC haplotype are used as they are more susceptible to CIA. In general, heterologous collagen is used as they are more immunogenic/arthritogenic tha homologous type II collagen. The mice are primed with an emulsion consisting of bovine type II collagen and Complete-Freund's Adjuvant at a 1:1 ratio (final concentration=2 mg/ml). The emulsion (0.1 ml) is injected into the tail of each mouse approximately 1-2 cm from the base. A whitish bolus beneath the dermis should be visible. A type II collagen booster (200 μg per mouse) is given intraperitoneally in PBS on day 21. High CIA-susceptible mice (DBA/1) generally develop arthritis 4-5 weeks after initial priming. Fully developed arthritis including red and swollen paws, can be observed 3-5 days after the onset and active inflammatory arthritis persists more than 3-4 weeks. Although inflammation will eventually subside, joint damage as seen as ankylosis is permanent. Assessment of CIA symptoms is essentially similar to the AIA model in which clinical signs is assigned clinical score (0-4) based on the severity of the disease. Histological measurements can also be performed on formalin-fixed joints to assess erosin, cellular infiltrates and hyperplasia.

In combined LPS-mAB induced Arthritis, a severe and consistent arthritis can be induced in mice by a combination of LPS and mAB cocktail that recognize individual epitopes clustered within an 83 amino acid peptide fragment located within CB11 region of type II collagen. This model was developed based on the hypothesis that bacterial toxin(s) absorbed through the GI tract play a synergistic and pathologic role with sub-arthritogenic levels of autoantibodies to type II collagen in triggering RA. The advantages of this model are: 1. synchronized arthritis (100%) is induced rapidly within 7 days 2. a variety of mouse strains can be used as administration of anti-type II collagen mAB cocktail bypasses the requirement for the host's generation of autoantibodies to type II collagen thus arthritis can be induced in mice that do not possess CIA-susceptible MHC haplotypes and 3. ease of administration of mAB and LPS by either i.v. and i.p. routes.

Inflammatory Bowel Diseases (IBD) which includes Crohn's disease (CD) and ulcerative colitis (UC) represents a group of chronic disorders characterized by inflammation of the gastrointestinal tract. CD can affect any part of the digestive track whereas UC affects only the colon and rectum. UC causes inflammation and ulcers, usually in the sigmoid colon and rectum. Cellular infiltrates are complex and pro-inflammatory cytokines are evident in CD and UC.

An experimental model of UC is established in Balb/C mice by administration of dextran sulphate sodium (3% DSS) isolated from *Leuconostoc* spp. into the drinking water. The experiment has a relatively short time-course (8 days) and parameters for assessment of colitis include loss of body weight, stool consistency, rectal bleeding, shortening of colonic length, crypt damage and cytokine analysis of colonic rings.

In CD, Balb/C mice are sensitized at day 0 with 2×50 μl of 5 mg/ml of dinitrofluobenzene (DNFB) epicutaneously to shaved abdomen and feet on two consecutive days. DNFB is typically solubilised in acetone:olive oil (4:1). On day 5, the mice are challenged intracolonically with 50 μl dintrobezene sulphonic acid (DNS) at 6 mg/ml in 10% ethanol. The mice are sacrificed on day 8. Parameters to be measured include suppression of total blood cell number and cell types, mucosal mast cell protease 1 (MMCP-1) in serum, TNFα level in colon homogenate, stool consistency, vascular permeability and number of colonic patches. Number of neutrophils and mast cells which are indicative of colonic damage and cellular influx will also be assessed by histological and microscopical examinations.

Asthma is restricted to human species, but animal models are often used to investigate particular aspects of this human disease. Bronchial biopsies and bronchoalveolar lavage (BAL) fluid recovered from patients with asthma have been shown to contain an increased number of activated T cells, B cells, eosinophils and mast cells. Many patients with asthma are sensitized and have specific immunoglogulin E (IgE) antibodies to one or more inhalant allergens. Atopy is, considered to be a major cause of asthma. In atopic individuals, inhalation of allergens preferentially induces a T-helper 2 cell (Th2) response. In the majority of current models, mice are sensitized by itraperitoneal (ip) injection of ovalbumin (OVA), often together with a Th2 skewed adjuvant, such as alum. In the classical mouse model for asthma, C57/BL6 mice are actively sensitized on day 0 by ip injection of 10 μg of OVA absorbed onto 1 mg of alum. From day 14-21 the mice are exposed daily to aerosolized OVA over a 30 minute period. On day 22, airway inflammation is apparent. BAL fluid recovered from these animals demonstrate an increase in peri-bronchiolar space consisting of mixed cellular infiltrates of mononuclear cells and eosinophils. OVA-specific IgE antibodies can be demonstrated in the serum of sensitized animals. The mononuclear cell population consists mainly of cells of Th2 phenotype secreting cytokines IL-4 and IL-5. IL-4 promotes isotype switching of B cells towards IgE synthesis and IL-5 influences the production, maturation and activation of eosinophils.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:
1. A compound of formula Ib

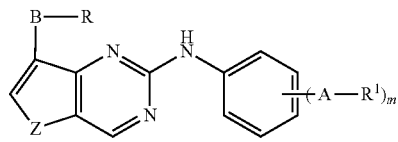

Formula Ib wherein
Z is $NR^2$ or S;
A and B are independently absent or substituted or unsubstituted $C_{1-6}$ alkylene wherein one or more carbon atoms can be optionally replaced with O, CO, $NR^2$, $NR^2CO$, $CONR^2$, $NR^2SO_2$, $SO_2NR^2$, S and/or $S(O)_n$, wherein n is 1 or 2;
$R^1$ is independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, OH, halogen, CN, $NO_2$, $NR^2R^3$, $SO_2R^3$, $SO_2NR^2R^3$, $CF_3$, $OCF_3$, $NR^2SO_2R^3$, $CO_2R^3$, $COSR^3$, $CSR^3$, $COR^3$, $NR^2$, $CSR^3$, $NR^2CSR^3$, $CONR^2R^3$, $NR^2COR^3$, $NR^2CONR^2R^3$, $SO_3R^3$, substituted or unsubstituted $C_{3-8}$ cycloalkyl, substituted or unsubstituted aryl and substituted or unsubstituted heterocyclyl having up to 3 heteroatoms selected from N, O, S and $SO_2$;
R is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, OH, halogen, CN, $NO_2$, $CO_2R^3$, $CONR^2R^3$, $NR^2COR^3$, $SO_3R^3$, $C_{3-8}$ cycloalkyl, aryl and heterocyclyl having up to 3 heteroatoms selected from N, O, S and $SO_2$, each of which may be substituted with up to 3 substituents independently selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, OH, $OCF_3$, halogen, CN, $NO_2$, $NR^2R^3$, $SO_2R^3$, $SO_2NR^2R^3$, $NR^2SO_2R^3$, $CO_2R^3$, $COR^3$, $NR^2COR^3$, $R^2NHCO_2R^3$, $CONR^2R^3$, $NR^2CONR^2R^3$ and substituted or unsubstituted heterocyclyl having up to 3 heteroatoms selected from N, O, S and $SO_2$;
$R^2$ and $R^3$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, CN, substituted or unsubstituted $C_{3-8}$ cycloalkyl, substituted or unsubstituted aryl and substituted or unsubstituted heterocyclyl having up to 3 heteroatoms selected from N, O, S and $SO_2$; and
m is 1 to 3; and
salts and/or stereoisomers thereof.

2. The compound according to claim 1, wherein A is absent, substituted or unsubstituted $C_{1-6}$ alkylene or substituted or unsubstituted divalent $C_{1-6}$ alkoxy and B is absent or S.

3. The compound according to claim 1, wherein R is independently selected from halogen, $CO_2R^3$, $CONR^2R^3$, $C_{3-8}$ cycloalkyl, 5 or 6 membered aryl and 5 to 8 membered heterocyclyls having up to 3 heteroatoms selected from N, O, S and $SO_2$, each of which may be substituted with up to 3 substituents independently selected from substituted or unsubstituted $C_{1-6}$ alkyl, substituted or unsubstituted 5 to 8 membered heterocyclyls having up to 3 heteroatoms selected from N, O, S and $SO_2$, $R^2OH$, $R^2NHCO_2R^3$, $OCF_3$, substituted or unsubstituted $C_{1-6}$ alkoxy, OH, $NR^2R^3$, $SO_2NR^2R^3$, $NR^2SO_2R^3$, $NR^2COR^3$, $CONR^2R^3$, $NR^2CONR^2R^3$, $COR^3$, $CO_2R^3$ and/or $SO_2R^3$ wherein $R^2$ and $R^3$ are as defined in claim 1.

4. The compound according to claim 1, wherein R is independently selected from phenyl unsubstituted or substituted with at least one of $NR^2R^3$, $NR^2COR^3$, substituted or unsubstituted $C_{1-6}$ alkoxy, substituted or unsubstituted 5 to 8 membered heterocyclyls having up to 3 heteroatoms selected from N, O, S and $SO_2$, $SO_2NR^2R^3$, $NR^2CONR^2R^3$, $NR^2SO_2R^3$, $R^2OH$, $R^2NHCO_2R^3$, $OCF_3$, $CONR^2R^3$ or substituted or unsubstituted $C_{1-6}$ alkyl; saturated or unsaturated 5 to 9 membered heterocyclyl having 1 to 2 N atoms unsubstituted or substituted with at least one of $C_{1-6}$ alkoxy, $CO_2R^3$ or $NR^2R^3$; and saturated or unsaturated 5 to 9 membered heterocyclyls having 1 to 2 O atoms substituted or unsubstituted with at least one of $C_{1-6}$ alkoxy, $CO_2R^3$ or $NR^2R^3$.

5. The compound according to claim 1, wherein $R^1$ is independently selected from H, halogen, substituted or unsubstituted $C_{1-6}$ alkenyl, substituted or unsubstituted $C_{2-6}$ alkyl, substituted or unsubstituted $C_{1-6}$ alkoxy, OH, halogen, $NO_2$, $NR^2R^3$, $NR^2COR^3$, $CO_2R^3$, $SO_2R^3$, $NR^2SO_2R^3$, substituted or unsubstituted $C_{3-8}$ cycloalkyl, substituted or unsubstituted 5 or 6 membered aryl and substituted or unsubstituted 5 to 8 membered saturated or unsaturated heterocyclyl having up to 3 heteroatoms selected from N, O, S and $SO_2$.

6. The compound according to claim 5, wherein the substituted or unsubstituted 5 to 8 membered saturated or unsaturated heterocyclyl having up to 3 heteroatoms is selected from N, O, S and $SO_2$ is morpholino, thiomorpholino, thiomorpholino-1-oxide, thiomorpholino-1,1-dioxide, $NR^2$-piperazine, 4-hydroxy piperidine, 3-hydroxy pyrrolidine, 3-hydroxypyrrole, piperidine or pyrrolidine.

7. The compound according to claim 1, wherein one of B-R and A-$R^1$ is a Michael acceptor selected from

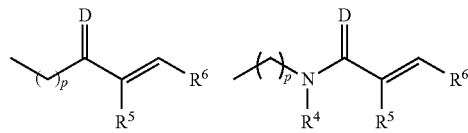

-continued

[chemical structures]

wherein
D is O or N;
R⁴ is selected from H and substituted and unsubstituted $C_{1-4}$alkyl; and
R⁵ and R⁶ are independently selected from H, substituted or unsubstituted $C_{1-4}$alkyl, $C_{1-4}$alkylNR⁸R⁹, $C_{1-4}$alkylOR⁸, substituted or unsubstituted aryl or may be joined to form a substituted or unsubstituted 5 to 8 membered ring optionally containing one or more heteroatoms selected from O, S, SO₂ and NR⁴;
R⁷ is selected from OH, OC$_{1-4}$alkyl, NR⁸R⁹;
p is 0 to 4; and
where R⁸ and R⁹ are independently selected from H, substituted or unsubstituted $C_{1-4}$alkyl or may be joined to form a substituted 3-8 membered ring optionally containing one or more heteroatoms selected from O, S, SO₂ and NR⁴; and
R¹⁰ is selected from H and substituted or unsubstituted $C_{1-4}$alkyl.

8. The compound according to claim 1 which is selected from the group consisting of:
1. 7-iodo-N-(4-morpholinophenyl)thieno[3,2-d]pyrimidin-2-amine
2. 7-(4-aminophenyl)-N-(4-morpholinophenyl)thieno[3,2-d]pyrimidin-2-amine
3. N-(4-(2-(4-morpholinophenylamino)thieno[3,2-d]pyrimidin-7-yl)phenyl)acrylamide
4. 7-(3-aminophenyl)-N-(4-morpholinophenyl)thieno[3,2-d]pyrimidin-2-amine
5. N-(3-(2-(4-morpholinophenylamino)thieno[3,2-d]pyrimidin-7-yl)phenyl)acrylamide
8. methyl 2-(4-morpholinophenylamino)thieno[3,2-d]pyrimidine-7-carboxylate
10. 7-(4-amino-3-methoxyphenyl)-N-(4-morpholinophenyl)thieno[3,2-d]pyrimidin-2-amine
11. 4-(2-(4-morpholinophenylamino)thieno[3,2-d]pyrimidin-7-yl)benzenesulfonamide
12. N,N-dimethyl-3-(2-(4-morpholinophenylamino)thieno[3,2-d]pyrimidin-7-yl)benzenesulfonamide
13. 1-ethyl-3-(2-methoxy-4-(2-(4-morpholinophenylamino)thieno[3,2-d]pyrimidin-7-yl)phenyl)urea
14. N-(4-(2-(4-morpholinophenylamino)thieno[3,2-d]pyrimidin-7-yl) phenyl)methanesulfonamide
15. 2-methoxy-4-(2-(4-morpholinophenylamino)thieno[3,2-d]pyrimidin-7-yl)phenol
16. 2-cyano-N-(3-(2-(4-morpholinophenylamino)thieno[3,2-d]pyrimidin-7-yl)phenyl)acetamide
17. N-(cyanomethyl)-2-(4-morpholinophenylamino)thieno[3,2-d]pyrimidine-7-carboxamide
18. N-(3-(2-(4-morpholinophenylamino)thieno[3,2-d]pyrimidin-7-yl)phenyl)methanesulfonamide
19. 1-ethyl-3-(4-(2-(4-morpholinophenylamino)thieno[3,2-d]pyrimidin-7-yl)-2-(trifluoromethoxy)phenyl)urea
20. N-(3-nitrophenyl)-7-phenylthieno[3,2-d]pyrimidin-2-amine
21. 7-iodo-N-(3-nitrophenyl)thieno[3,2-d]pyrimidin-2-amine
22. N1-(7-(2-ethylphenyl)thieno[3,2-d]pyrimidin-2-yl)benzene-1,3-diamine
25. -tert-butyl-3-(2-(4-morpholinophenylamino)thieno[3,2-d]pyrimidin-7-yl)benzenesulfonamide
26. N1-(7-iodothieno[3,2-d]pyrimidin-2-yl)benzene-1,3-diamine
28. 7-(4-amino-3-(trifluoromethoxy)phenyl)-N-(4-morpholinophenyl)thieno[3,2-d]pyrimidin-2-amine
29. 7-(2-ethylphenyl)-N-(4-morpholinophenyl)thieno[3,2-d]pyrimidin-2-amine
30. N-(3-(2-(4-morpholinophenylamino)thieno[3,2-d]pyrimidin-7-yl)phenyl)acetamide
31. N-(cyanomethyl)-N-(3-(2-(4-morpholinophenylamino)thieno[3,2-d]pyrimidin-7-yl)phenyl)methanesulfonamide
32. N-(cyanomethyl)-N-(4-(2-(4-morpholinophenylamino)thieno[3,2-d]pyrimidin-7-yl)phenyl)methanesulfonamide
33. N-(3-(5-methyl-2-(4-morpholinophenylamino)-5H-pyrrolo[3,2-d]pyrimidin-7-yl)phenyl)methanesulfonamide
34. 4-(5-methyl-2-(4-morpholinophenylamino)-5H-pyrrolo[3,2-d]pyrimidin-7-yl)benzenesulfonamide
35. N-(4-(5-methyl-2-(4-morpholinophenylamino)-5H-pyrrolo[3,2-d]pyrimidin-7-yl)phenyl)methanesulfonamide
36. 7-iodo-N-(4-morpholinophenyl)-5H-pyrrolo[3,2-d]pyrimidin-2-amine
37. 7-(2-isopropylphenyl)-N-(4-morpholinophenyl)thieno[3,2-d]pyrimidin-2-amine
38. 7-bromo-N-(4-morpholinophenyl)thieno[3,2-d]pyrimidin-2-amine
39. N7-(2-isopropylphenyl)-N2-(4-morpholinophenyl)thieno[3,2-d]pyrimidine-2,7-diamine
40. N7-(4-isopropylphenyl)-N2-(4-morpholinophenyl)thieno[3,2-d]pyrimidine-2,7-diamine
41. 7-(5-amino-2-methylphenyl)-N-(4-morpholinophenyl)thieno[3,2-d]pyrimidin-2-amine
42. N-(cyanomethyl)-4-(2-(4-morpholinophenylamino)thieno[3,2-d]pyrimidin-7-yl)benzamide
43. 7-iodo-N-(3-morpholinophenyl)thieno[3,2-d]pyrimidin-2-amine
44. 7-(4-amino-3-nitrophenyl)-N-(4-morpholinophenyl)thieno[3,2-d]pyrimidin-2-amine
45. 7-(2-methoxypyridin-3-yl)-N-(4-morpholinophenyl)thieno[3,2-d]pyrimidin-2-amine
46. (3-(7-iodothieno[3,2-d]pyrimidin-2-ylamino)phenyl)methanol
47. N-tert-butyl-3-(2-(3-morpholinophenylamino)thieno[3,2-d]pyrimidin-7-yl)benzenesulfonamide
48. N-tert-butyl-3-(2-(3-(hydroxymethyl)phenylamino)thieno[3,2-d]pyrimidin-7-yl)benzenesulfonamide
49. N-(4-morpholinophenyl)-7-(4-nitrophenylthio)-5H-pyrrolo[3,2-d]pyrimidin-2-amine
50. N-tert-butyl-3-(2-(3,4,5-trimethoxyphenylamino)thieno[3,2-d]pyrimidin-7-yl)benzenesulfonamide
51. 7-(4-amino-3-nitrophenyl)-N-(3,4-dimethoxyphenyl)thieno[3,2-d]pyrimidin-2-amine
51. N-(3,4-dimethoxyphenyl)-7-(2-methoxypyridin-3-yl)thieno[3,2-d]pyrimidin-2-amine
52. N-tert-butyl-3-(2-(3,4-dimethoxyphenylamino)thieno[3,2-d]pyrimidin-7-yl)benzenesulfonamide
54. 7-(2-aminopyrimidin-5-yl)-N-(3,4-dimethoxyphenyl)thieno[3,2-d]pyrimidin-2-amine 55. N-(3,4-dimethoxyphenyl)-7-(2,6-dimethoxypyridin-3-yl)thieno[3,2-d]pyrimidin-2-amine
56. N-(3,4-dimethoxyphenyl)-7-(2,4-dimethoxypyrimidin-5-yl)thieno[3,2-d]pyrimidin-2-amine
57. 7-iodo-N-(4-(morpholinomethyl)phenyl)thieno[3,2-d]pyrimidin-2-amine
58. N-tert-butyl-3-(2-(4-(morpholinomethyl)phenylamino)thieno[3,2-d]pyrimidin-7-yl)benzenesulfonamide
59. 2-cyano-N-(4-methyl-3-(2-(4-morpholinophenylamino)thieno[3,2-d]pyrimidin-7-yl)phenyl)acetamide
60. ethyl 3-(2-(4-morpholinophenylamino)thieno[3,2-d]pyrimidin-7-yl)benzoate
61. 7-bromo-N-(4-(2-(pyrrolidin-1-yl)ethoxy)phenyl)thieno[3,2-d]pyrimidin-2-amine
62. N-(3-(2-(4-(2-(pyrrolidin-1-yl)ethoxy)phenylamino)thieno[3,2-d]pyrimidin-7-yl )phenyl)acetamide
63. N-(cyanomethyl)-3-(2-(4-morpholinophenylamino)thieno[3,2-d]pyrimidin-7-yl)benzamide
64. N-tert-butyl-3-(2-(4-morpholinophenylamino)thieno[3,2-d]pyrimidin-7-yl)benzamide
65. N-tert-butyl-3-(2-(4-(1-ethylpiperidin-4-yloxy)phenylamino)thieno[3,2-d]pyrimidin-7-yl)benzenesulfonamide
66. tert-butyl 4-(2-(4-(morpholinomethyl)phenylamino)thieno[3,2-d]pyrimidin-7-yl)-1H-pyrazole-1-carboxylate
67. 7-bromo-N-(4-((4-ethylpiperazin-1-yl)methyl)phenyl)thieno[3,2-d]pyrimidin-2-amine
68. N-tert-butyl-3-(2-(4-((4-ethylpiperazin-1-yl)methyl)phenylamino)thieno[3,2-d]pyrimidin-7-yl)benzenesulfonamide
69. N-(4-((4-ethylpiperazin-1-yl)methyl)phenyl)-7-(1H-pyrazol-4-yl)thieno[3,2-d]pyrimidin-2-amine
70. N-(cyanomethyl)-3-(2-(4-(morpholinomethyl)phenylamino)thieno[3,2-d]pyrimidin-7-yl)benzamide
71. N-tert-butyl-3-(2-(4-(2-(pyrrolidin-1-yl)ethoxy)phenylamino)thieno[3,2-d]pyrimidin-7-yl)benzenesulfonamide
72. tert-butyl pyrrolidin-1-yl)ethoxy)phenylamino)thieno[3,2-d]pyrimidin-7-yl)benzylcarbamate
73. 3-(2-(4-(2-(pyrrolidin-1-yl)ethoxy)phenylamino)thieno[3,2-d]pyrimidin-7-yl)benzenesulfonamide
74. 7-(3-chloro-4-fluorophenyl)-N-(4-(2-(pyrrolidin-1-yl)ethoxy)phenyl)thieno[3,2-d]pyrimidin-2-amine
75. tert-butyl 4-(2-(4-(1-ethylpiperidin-4-yloxy)phenylamino)thieno[3,2-d]pyrimidin-7-yl)-1H-pyrazole-1-carboxylate
76. 7-(benzo[d][1,3]dioxol-5-yl)-N-(4-(morpholinomethyl)phenyl)thieno[3,2-d]pyrimidin-2-amine
77. tert-butyl 5-(2-(4-(morpholinomethyl)phenylamino)thieno[3,2-d]pyrimidin-7-yl)-1H-indole-1-carboxylate
78. 7-(2-aminopyrimidin-5-yl)-N-(4-(morpholinomethyl)phenyl)thieno[3,2-d]pyrimidin-2-amine
79. tert-butyl 4-(2-(4-(morpholinomethyl)phenylamino)thieno[3,2-d]pyrimidin-7-yl)-5,6-dihydropyridine-1(2H)-carboxylate
80. tert-butyl 4-(2-(4-(morpholinomethyl)phenylamino)thieno[3,2-d]pyrimidin-7-yl)benzylcarbamate
81. N-(3-(2-(4-(morpholinomethyl)phenylamino)thieno[3,2-d]myrimidin-7-yl)phenyl)acetamide
82. N-(4-(2-(4-(morpholinomethyl)phenylamino)thieno[3,2-d]pyrimidin-7-yl)phenyl)acetamide
83. N-(3-(2-(4-(morpholinomethyl)phenylamino)thieno[3,2-d]pyrimidin-7-yl)phenyl)methanesulfonamide
84. 7-(4-(4-methylpiperazin-1-yl)phenyl)-N-(4-(morpholinomethyl)phenyl)thieno[3,2-d]pyrimidin-2-amine
85. N-(2-methoxy-4-(2-(4-(morpholinomethyl)phenylamino)thieno[3,2-d]pyrimidin-7-yl)phenyl)acetamide
86. 7-bromo-N-(3,4,5-trimethoxyphenyl)thieno[3,2-d]pyrimidin-2-amine
87. (3-(2-(3,4,5-trimethoxyphenylamino)thieno[3,2-d]pyrimidin-7-yl)phenyl)methanol
88. (4-(2-(3,4,5-trimethoxyphenylamino)thieno[3,2-d]pyrimidin-7-yl)phenyl)methanol
89. (3-(2-(4-morpholinophenylamino)thieno[3,2-d]pyrimidin-7-yl)phenyl)methanol
90. (4-(2-(4-morpholinophenylamino)thieno[3,2-d]pyrimidin-7-yl)phenyl)methanol
91. N-(pyrrolidin-1-yl)ethoxy)phenylamino)thieno[3,2-d]pyrimidin-7-yl)benzyl)methanesulfonamide
92. tert-butyl 3-(2-(4-(morpholinomethyl)phenylamino)thieno[3,2-d]pyrimidin-7-yl)benzylcarbamate
93. N-(4-(morpholinomethyl)phenyl)-7-(3-(piperazin-1-yl)phenyl)thieno[3,2-d]pyrimidin-2-amine
94. 7-(6-(2-morpholinoethylamino)pyridin-3-yl)-N-(3,4,5-trimethoxyphenyl)thieno[3,2-d]pyrimidin-2-amine
95. 7-(2-ethylphenyl)-N-(4-(pyrrolidin-1-yl)ethoxy)phenyl)thieno[3,2-d]pyrimidin-2-amine
96. 7-(2-isopropylphenyl)-N-(4-(pyrrolidin-1-yl)ethoxy)phenyl(thieno[3,2-d]pyrimidin-2-amine
97. 7-(4-(aminomethyl)phenyl)-N-(4-(morpholinomethyl)phenyl)thieno[3,2-d]pyrimidin-2-amine
98. N-(4-(1-ethylpiperidin-4-yloxy)phenyl)-7-(1H-pyrazol-4-yl)thieno[3,2-d]pyrimidin-2-amine
99. N-(2,4-dimethoxyphenyl)-7-phenylthieno[3,2-d]pyrimidin-2-amine
100. 7-bromo-N-(3,4-dimethoxyphenyl)thieno[3,2-d]pyrimidin-2-amine and
101. N-(3,4-dimethoxyphenyl)-7-phenylthieno[3,2-d]pyrimidin-2-amine and salts and/or stereoisomers thereof.

9. The compound according to claim 1, wherein the compound is a kinase inhibitor.

10. A process for the preparation of the compound of formula Ib according to claim 1 which comprises the step of coupling a compound of formula IIb

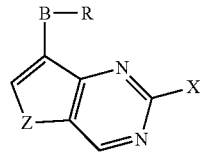

Formula IIb wherein,
Z, B and R are as defined in claim 1; and
X is a leaving group;
with a compound of formula IIIb

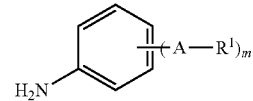

Formula IIIb wherein
A, $R^1$ and m are as defined in claim 1.

11. A pharmaceutical composition comprising the compound of formula I according to claim 1 and a pharmaceutically acceptable carrier.

* * * * *